(12) United States Patent
Lagarias et al.

(10) Patent No.: US 7,033,806 B2
(45) Date of Patent: Apr. 25, 2006

(54) HY2 FAMILY OF BILIN REDUCTASES

(75) Inventors: John Clark Lagarias, Davis, CA (US); Takayuki Kochi, Ikoma (JP); Nicole Frankenberg, Davis, CA (US); Gregory A. Gambetta, Davis, CA (US); Beronda L. Montgomery, Bloomington, IN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/870,406

(22) Filed: May 29, 2001

(65) Prior Publication Data

US 2003/0104379 A1   Jun. 5, 2003

Related U.S. Application Data

(60) Provisional application No. 60/271,758, filed on Feb. 26, 2001, provisional application No. 60/210,286, filed on Jun. 8, 2000.

(51) Int. Cl.
  C12N 9/02 (2006.01)
  C12N 1/20 (2006.01)
  C12Q 1/68 (2006.01)
  C12P 21/04 (2006.01)
  C07H 21/04 (2006.01)

(52) U.S. Cl. ............... 435/189; 435/4; 435/6; 435/69.1; 435/71.1; 435/252.3; 435/320.1; 435/440; 536/23.6

(58) Field of Classification Search ........... 435/189, 435/252.3, 320.1, 71.1, 440, 6, 4, 69.1; 536/23.2, 536/23.6

See application file for complete search history.

(56) References Cited

U.S. PATENT DOCUMENTS 5,538,885 A * 7/1996 Hollis et al. ............... 435/355
6,294,714 B1   9/2001 Matsunaga et al.

OTHER PUBLICATIONS

Lin et al. Sequence Search Result.*
Gil et al. (2000) "Photocontrol of subcellular partitioning of phytochrome-B:GFP fusion protein in tobacco seedlings." *Plant J.* 22(2): 135-145.
Halliday et al. (1999) " POC1 : An Arabidopsis mutant perturbed in phytochrome signaling because of aT DNA insertion in the promoter of PIF3, a gene encoding a phytochrome-interacting bHLH protein." *Proc. Natl. Acad. Sci., USA*, 96: 5832-5837.
Hisada et al. (2000) "light-Induced Nuclear Translocation of Endogenous Pea Phytochrome A Visualized by Immunocytochemical Procedures." *Plant Cell* 12: 1063-1078.
Kim et al. (2000) "Light-induced nuclear import of phytochrome-A:GFP fusion proteins is differentially regulated in transgenic tobacco and Arabidopsis." *Plant J.* 22(2): 125-133.

(Continued)

*Primary Examiner*—Manjunath Rao
*Assistant Examiner*—Yong Pak
(74) *Attorney, Agent, or Firm*—Quine I.P. Law Group, P.C.; Tom Hunter

(57) ABSTRACT

This invention identifies a novel family of bilin reductases. Designated herein HY bilin reductases, the enzymes of this invention are useful in a wide variety of contexts including but not limited to the conversion of biliverdins to phytobilins and the assembly of holophytochromes or phytofluors.

3 Claims, 16 Drawing Sheets

OTHER PUBLICATIONS

Kircher et al. (1999) "Light Quality-Dependant Nuclear Import of the Plant Photoreceptors Phytochrome A and B" *Plant Cell* 11: 1445-1456.

Martinez-Garcia et al. (2000) "Cirect Targeting of Light Signals to a Promoter Element-Bound Transcription Factor." *Science* 288: 859-863.

Nagatani (1997) "Spatial Distribution of Pytochromes." *J. Plant Res.* 110: 123-130.

Nagy and Schafer (1999) "Control of nuclear import and phytochromes." *Trends in Plant Science* 4(4): 125-126.

Nagy and Schafer (2000) "Phytochromes, pif3 and light signalling go nuclear." *Curr. Opin. Plant Biol.*, 3: 450-454.

Nagy and Schafer (2000) "Nuclear and cytosolic events of light-induced, phytochrome-regulated signaling in higher plants." *EMBO J.* 19(2): 157-163.

Nagy et al. (2000) "Nucleo-cytoplasmic partitioning of the plant photoreceptors phytochromes" *Seminars in Cell & Development Biology* 11: 505-510.

Ni et al. (1998) "PIF3, a Phytochrome-Interacting Factor Necessary for Normal Photinduced Signal Transduction, Is a Novel Basic Helix-Loop-Helix Protein." *Cell* 95: 657-667.

Ni et al. (1999) "Binding of phytochrome B to its nuclear signalling partner PIF3 is reversibly induced by light" *Nature* 400: 781-784.

Sakamoto and Nagatani (1996) "Nuclear localization activity of phytochrome B." *Plant J.* 10(5): 859-868.

Shimizu-Sato et al. (2002) "A light-switchable gene promoter system" *Nature Biotechnology*, 20(10): 1041-1044.

Yamaguchi et al. (1999) "Light-dependant Translocation of a Phytochrome B-GFP Fusion Protein to the Nucleus in Transgenic Arabidopsis." *J. Cell. Biol.* 145(3): 437-445.

Zhu et al. (2000) "Phytochrome B binds with greater apparent affinity thatn phytochrome A to the basic helix-loop-helidx factor PIF3 in a reaction requiring the PAS domain of PIF3" *Proc. Natl. Acad. Sci., USA*, 97(24): 13419-13424.

Taiz et al. (1998) Phytochrome Chapter 17, Plant Physiology 1nd Sinauer Associates, Inc. Publishers, pp. 487.

(1988) Dorland's Illlustrated Medical Dictionary, pp. 113, 1362.

Kusugi et al. (2002) Interations of the Arbidopsis E2F and DP Proteins Confers Their Concommitant Nuclear Translocation and Transactivation Plant Physiology vol. 128 pp. 833-843.

Guralnick et al. (1996) The Plant Cell Transport of DNA into the Nuclei of Xanopus Oocytes by a Modified VirE2 Protein of Agrobacterium. Vo. 8. pp. 363-373.

* cited by examiner

```
gaattccccacgtcaacgtgactgtgcattccacgtggcggatgtgggccctatagttgg    60
accatgactcggacggatgttgaaattcattgtcgttgccaattgcgtttgtctcactga   120
aactgtgaaaattttatctcttttatagataaAGAATCTTGCTTTTTTCAGTTTTCAGTA   180
TGAAGAAGAATTGAAGAGAGTGTCCGAGGAAGGAGACCTTTGGTTTCAGTTTGTGAGTCT   240
TGTTGTAATGGCTTTATCAATGGAGTTTGGGTTTTCAATTGGGTCATGCTTCAAGGCACC   300
           M  A  L  S  M  E  F  G  F  S  I  G  S  C  F  K  A  P
AAACCCACCTGTTCTAATCTCTGCAAGCCCTAATAAGATCAATTTCACGTTGAGAAGGAG   360
 N  P  P  V  L  I  S  A  S  P  N  K  I  N  F  T  L  R  R  R
AAAGAAAAGATTCTTACTTAGAGTCTCTGCTGTGTCGTATAAGGAATTCGCAGAGTCTGC   420
                 hy2-106 *****
  K  K  R  F  L  L  R  V  S  A  V  S  Y  K  E  F  A  E  S  A
TTTAGAAGAAACCAGGAAAAGGATCGTTCTTGAACCTTCACATCTCCAGgtatatgcaat   480
 L  E  E  T  R  K  R  I  V  L  E  P  S  H  L  Q
tacatttagttagtgtagtgggaggattatatttctcattgtttcttgctgtgaattttg   540
ggtaaattgatttgagttgtcattaggaaccaaacaaataactttactgttatagactgc   600
ttatataagtaaaagttcagattttgtttttctaatcacgaaactgtttcagGAAAAGTA   660
                                                    E  K  Y
TAGTAGCATGACAGGACTAGATGGTAAGACCGAACTTCAAATGCTTGCTTTTAAATCTTC   720
 S  S  M  T  G  L  D  G  K  T  E  L  Q  M  L  A  F  K  S  S
AAAGATTAGACTCTTGAGGAGTATGGCAATAGAGAATGAGACAATGCAGgtttaacttca   780
 K  I  R  L  L  R  S  M  A  I  E  N  E  T  M  Q
gcagtacaaactgattgctttagtcccatttccttactttcaattgattgattgtttgta   840
      hy2-105 **********************
tcttcgcttagGTCTTTGACTTTGCGGGTTTCATGGAGCCTGAGTATGATACTCCCATAT   900
                                       hy2-1,hy2-104   T
              V  F  D  F  A  G  F  M  E  P  E  Y  D  T  P  I  F
TCTGTGCTAACTTTTTCACATCTACCAACGTTAACATAGTTGTATTgtaagttatcttct   960
 C  A  N  F  F  T  S  T  N  V  N  I  V  V  L
agttatgctggagttatcaggtctgtattgtccaaactgatgttcaatattttactgtat  1020
gttcttctttagGGACCTTAATCCTTTGCATCAGTTGACTGACCAGACGGATTACCAAGA  1080
             D  L  N  P  L  H  Q  L  T  D  Q  T  D  Y  Q  D
CAAGTATTATAACAAGATAATGTCCATATATCACAAATATGCTGAGgtgaccacaagaat  1140
 K  Y  Y  N  K  I  M  S  I  Y  H  K  Y  A  E
acaccaaattactcaattgcaagtaaacctaatgctgaggtgtaaatgactgatcttgag  1200
atttatttgcagACTTTCCCATGGGGAGGGAAATTGACTGGTGAATCCATAAAGTTTTTC  1260
             hy2-101  A
              T  F  P  W  G  G  K  L  T  G  E  S  I  K  F  F
TCGCCTTTGGTGATGTGGACTAGGTTTTCGTCTAGCAAAGAAAAACATAAGGCTTTGTTC  1320
 S  P  L  V  M  W  T  R  F  S  S  S  K  E  K  H  K  A  L  F
TCTGCGTTTCTAGAGTACTATCAGgtatatactcagcggccaaaagctaaggttttattg  1380
 S  A  F  L  E  Y  Y  Q
gaaactttgactgagaatctatcatcttcttcctacagGCATGGCTTGAGATGACAATCC  1440
                                       hy2-107  a
                                        A  W  L  E  M  T  I  Q
AAGTGAGGGAGGAGATGGAACCATCTCATGTGAGAGCCAATTGTGAAGCACAACACAAGT  1500
 V  R  E  E  M  E  P  S  H  V  R  A  N  C  E  A  Q  H  K  Y
ACCTGACATGGCGAGCACAAAAGgtgatttcatttccttttgtgtaatttgcatgtttga  1560
  hy2-103  A
  L  T  W  R  A  Q  K
acagacactgtatctgtattgttacaatggatattgatttggtgtttgcagGATCCTGGA  1620
                          hy2-102  a
                                                     D  P  G
CATGGTCTTCTTAAAAGATTAGTAGGTGAAGCAAAGGCAAAGgtataaaagatttgatcc  1680
 H  G  L  L  K  R  L  V  G  E  A  K  A  K
cattagtgtcccattattaattagcttgtgaagatgttgaaaatgatttgaacaaaatc  1740
```

HY2 FAMILY OF BILIN REDUCTASES

CROSS-REFERENCE TO RELATED APPLICATIONS

This application claims benefit of and priority to U.S. Ser. No. 60/271,758 filed on Feb. 26, 2001, and to U.S. Ser. No. 60/210,286, filed on Jun. 8, 2000, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made, in part, with Government support under Grant Nos: 98-35304-6404 and AMD-9801768 awarded by the United States Department of Agriculture. The Government of the United States of America may have certain rights in this invention.

FIELD OF THE INVENTION

This invention relates to the field of phytochromes. In particular, this invention relates to the discovery of a phytochromobilin synthase and a family of related enzymes from photosynthetic prokaryotes that is are capable of converting a biliverdin into a the phytochrome- and phycobiliprotein chromophore precursors—phytochromobilin, phycocyanobilin and phycoerythrobilin.

BACKGROUND OF THE INVENTION

The phytochromes comprise a family of biliprotein photoreceptors that enable plants to adapt to their prevailing light environment (Kendrick and Kronenberg (1994) Kendrick, Pp. 828 in *Photomorphogenesis in Plants*, Dordrecht, The Netherlands: Kluwer Academic Publishers). Phytochromes possess the ability to efficiently photointerconvert between red light absorbing Pr and far red light absorbing Pfr forms, a property conferred by covalent association of a linear tetrapyrrole (bilin or phytobilin) with a large apoprotein. Phytochromes from cyanobacteria, to green algae and higher plants consist of a well conserved N-terminal polypeptide, roughly 390–600 amino acids in length (see, e.g. U.S. Pat. No. 6,046,014), to which the phytobilin prosthetic group, e.g., phytochromobilin (PΦB) or phycocyanobilin (PCB) is bound.

Phytobilins are linear tetrapyrrole molecules synthesized by plants, algae, and cyanobacteria that function as the direct precursors of the chromophores of the light-harvesting phycobiliproteins and of the photoreceptor phytochrome (Beale (1993) *Chem. Rev.* 93: 785–802; Hughes and Lamparter (1999) *Plant Physiol.* 121: 1059–1068). The pathways of phytobilin biosynthesis have been elucidated by biochemical fractionation of plant and algal extracts, by overcoming a blocked step with exogenous putative intermediates, and by analysis of linear tetrapyrrole-deficient mutants (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345; Terry et al. (1993) *Arch. Biochem. Biophys.* 306: 1–15). These studies indicate that the biosynthesis of phytobilins shares common intermediates with heme and chlorophyll biosynthetic pathways to the level of protoporphyrin IX, at which point the latter two pathways diverge by metalation with iron or magnesium (Beale (1993) *Chem. Rev.* 93: 785–802). Phytobilins are derived from heme, which is converted to biliverdin IXa (BV), the first committed intermediate in their biosynthesis. In red algae, cyanobacteria, and plants, this interconversion is accomplished by ferredoxin-dependent heme oxygenases that are related in sequence to the mammalian heme oxygenase (Cornejo et al. (1998) *Plant J.* 15: 99–107.; Davis et al. (1999) *Proc. Natl. Acad. Sci., USA*, 96: 6541–6546; Muramoto et al. (1999) *Plant Cell* 11: 335–347). Although they catalyze the same reaction, mammalian heme oxygenases use an NADPH-dependent cytochrome P450 reductase to generate reducing power for heme catabolism (Maines (1988) *FASEB J.* 2: 2557–2568).

The metabolic fate of BV differs in mammals, cyanobacteria, and plants, with BV being metabolized by different reductases with unique double-bond specificities (FIG. 1). Mammalian biliverdin IXa reductase (BVR), an NAD(P)H-dependent enzyme that catalyzes the two-electron reduction of BV at the C10 methine bridge to produce bilirubin IXa (BR), was the first of these enzymes to be discovered (Maines and Trakshel (1993) *Arch. Biochem. Biophys.* 300: 320–326). A similar enzyme, encoded by the gene bvdR, was identified in cyanobacteria (Schluchter and Glazer (1997) *J. Biol. Chem.* 272: 13562–13569). Cyanobacteria and red algae also possess novel ferredoxin-dependent bilin reductases for the synthesis of the linear tetrapyrrole precursors of their phycobiliprotein light-harvesting antennae complexes (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345; Cornejo et al. (1998) *Plant J.* 15: 99–107). Primarily on the basis of studies with the red alga *Cyanidium caldarium*, these investigators proposed that the biosynthesis of the two major phycobiliprotein chromophore precursors, phycoerythrobilin (PEB) and phycocyanobilin (PCB), utilized two ferredoxin-dependent bilin reductases and several double-bond isomerases. The first bilin reductase catalyzes the two-electron reduction of BV at the C15 methine bridge to produce the BR isomer 15,16-dihydrobiliverdin (DHBV), whereas the second bilin reductase catalyzes the conversion of 15,16-DHBV to 3Z-PEB, a formal two-electron reduction of the C2 and C3 diene system. In *C. caldarium*, an additional enzyme mediates the isomerization of 3Z-PEB to 3Z-PCB, both of which appear to be isomerized to their corresponding 3E isomers before assembly with the nascent phycobiliprotein apoproteins (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345).

More recent studies lend support for a similar pathway of PCB and PEB synthesis in cyanobacteria (Cornejo and Beale (1997) *Photosynth. Res.* 51: 223–230). In contrast with mammals and phycobiliprotein-containing organisms, plants and green algae reduce BV to 3Z-PFB by the ferredoxin-independent enzyme PΦB synthase, which targets the $2,3,3^1,3^2$-diene system for reduction (Terry et al. (1995) *J. Biol. Chem.* 270: 11111–11118; Woo et al. (1997) *J. Biol. Chem.* 272: 25700–25705). In plants, 3Z-PFB is isomerized to its 3E isomer, which appears to be the immediate precursor of the phytochrome chromophore (Ibid). The green alga *Mesotaenium caldariorum* possesses a second bilin reductase activity that catalyzes the reduction of the 18-vinyl group of PFB to produce 3Z-PCB (Wu et al. (1997) *J. Biol. Chem.* 272: 25700–25705). These investigations also revealed that 3E-PCB is the natural phytochrome chromophore precursor in this organism.

Despite the extensive biochemical analysis of the phytobilin biosynthetic pathways in plants, algae, and cyanobacteria, the low levels of bilin reductase expression have previously hindered efforts to clone these enzymes.

SUMMARY OF THE INVENTION

This invention pertains to the isolation and characterization of a family of bilin reductases (designated herein as the HY2 family). These bilin reductases catalyze the conversion of a biliverdin to a phytobilin and can form component (s) of a phytochrome biosynthetic pathway. The bilin reductases of this invention can be used in vivo or in vitro to simply convert biliverdins to phytobilins or, in conjunction with other enzymes in the phytochrome synthetic pathway to synthesize complete phytochromes and/or phytofluors.

In one embodiment, this invention provides an isolated HY2 family bilin reductase comprising an amino acid consensus sequence as illustrated in FIG. 5 or in FIG. 10 and having bilin reductase activity. In certain embodiments, the bilin reductase comprises at least 50% sequence conservation, preferably at least 70% sequence conservation, most preferably at least 90% sequence conservation as shown in FIG. 10 and/or at least 80% sequence conservation more preferably at least 100% sequence conservation as shown in FIG. 5. In certain preferred embodiments, the bilin reductase is PebA and/or PebB.

In another embodiment, this invention provides a ferredoxin-dependent bilin reductase comprising at least 15%, preferably at least 20%., more preferably at least 30%, and most preferably at least 50%, at least 75%, at least 90% or at least 95% sequence identity with an enzyme selected from the group consisting of HY2_ARATH, YCP2_SYNPY, YHP2_PROMA, YIP3_PROMA, YCP3_SYNPY, SLR0116, PcyA_ANASP, PcyA_NOSPU, PcyA_SyNY3, PcyA_SYN8.1, PcyA_PROME, PebA_SYNPY, PebA_SYN8.1, PebA_PROMA, PebA_PROME, PewbB_NOSPU, HY2_ARATH, RCCR_ARATH, and RCCR_HORVU, and where, when aligned with HY2, comprises conserved hydrophobic residues at position 137, 157, 158, 256, and 314. In preferred embodiments, the bilin reductase, when aligned with HY2, comprises a residue selected from the group consisting of Pro-151, Phe-221, Ser222, and ASP-171 and more preferably when aligned with HY2, comprises Pro-151, Phe-221, Ser-222, and ASP-171.

In certain embodiments, the HY2 bilin reductases (HY2 family members) of this invention exclude (proviso out) one or more of the following: hvrccr, atrccr, rccr_horvu, rccr_arath, ycp2_synpy, ycp3_synpy, and HY2.

In still another embodiment, this invention provides an isolated bilin reductase having bilin reductase activity and comprising an amino acid sequence of polypeptide selected from the group consisting of HY2, athy2, slr0116, c362_anab, ycp2_synpy, ycp3_synpy, PcyA_ANASP, PcyA_NOSPU, PcyA_SYNY3, PcyA_SYN81, PcyA_PROME, PebA_SYNPY, PebA_SYN81, PebA_PROMA, PebA_PROME, PebA_NOSPU, PebB_SYNPY, PebB_SYN81, PebB_PROMA, PebB_PROME, PebB_NOSPU, HY2_ARATH, RCCR_ARATH, and RCCR_HORVU, or conservative substitutions thereof. In preferred embodiments, the bilin reductase comprises an amino acid sequence of a polypeptide selected from the group consisting of athy2, slr0116, c362_anab, ycp2-synpy, ycp3_synpy, PcyA_ANASP, PcyA_NOSPU, PcyA_SYNY3, PcyA_SYN81, PcyA_PROME, PebA_SYNPY, PebA_SYN81, PebA_PROMA, PebA_PROME, PebA_NOSPU, PebB_SYNPY, PebB_SYN81, PebB_PROMA, PebB_PROME, PebB_NOSPU, HY2_ARATH, RCCR_ARATH, and RCCR_HORVU.

This invention also provides methods of converting a biliverdin to a phytobilin. The methods involve contacting a bilin reductase of this invention (e.g. an HY2 family bilin reductase) with a biliverdin whereby the biliverdin is converted to a phytobilin. In certain embodiments, the bilin reductase is a cyanobacterial bilin reductase, and/or an algal bilin reductase, and/or a plant bilin reductase. The bilin reductase can be a recombinantly expressed bilin reductase. The contacting can be in vivo or ex vivo. In certain embodiments, the contacting is in a cell and the bilin reductase is a heterologous polypeptide. The methods can further comprise contacting the phytochromobilin with a second bilin reductase to produce a phytochrome. In certain embodiments, the methods further comprise contacting the phytochromobilin with a second bilin reductase (e.g. PebB) to produce a phytofluor. In certain embodiments, the bilin reductase is ycp2-snpy and/or ycp3-snpy.

This invention also provides isolated nucleic acids encoding a bilin reductase as described herein (e.g. an HY2 family member). Preferred nucleic acids comprise a vector.

Also are provided cells comprising a heterologous nucleic acid comprising a nucleic acid encoding a bilin reductase (e.g. an HY2 family member) as described herein. Preferred cells include, but are not limited to algal cells, plant cells, yeast cells, bacterial cells, insect cells, and mammalian cells.

In still another embodiment, this invention provides a a nucleic acid that specifically hybridizes with a nucleic acid encoding any of the bilin reductases described herein under stringent conditions and that encodes a polypeptide having bilin reductase activity. In certain embodiments, the nucleic acids exclude (proviso out) nucleic acids encoding one or more of the following: hvrccr, atrccr, rccr_horvu, rccr_arath, ycp2_synpy, ycp3_synpy, and HY2. Preferred nucleic acids are vectors (e.g. plasmids, cosmids, etc.).

In still another embodiment, this invention provides a method of detecting expression of a polypeptide. The method comprises providing a cell comprising a nucleic acid encoding an apophytochrome; and a nucleic acid encoding a bilin reductase that produces a phytobilin that assembles with said apophytochrome to produce a holophytochrome or a phytofluor; and detecting an optical signal produced by the holophytochrome or phytofluor.

This invention also provides a method of producing a photoactive holophytochrome. The method involves co-expressing in a cell (e.g., an algal cell, a yeast cell, a bacterial cell, a plant cell, an insect cell, a mammalian cell, etc.): a heme oxygenase; an apophytochrome; and a ferredoxin-dependent bilin reductase; whereby the cell produces the photoactive holophytochrome and where one or more of the apophytochrome and the ferredoxin-dependent bilin reductase are expressed by heterologous nucleic acids. In preferred embodiments, the ferredoxin-dependent bilin reductase is an HY2 family bilin reductase (e.g. HY2, pcyA, etc.). In a preferred embodiment, the apophytochrome and the ferredoxin-dependent bilin reductase are both expressed by heterologous nucleic acids. In certain embodiments, the heme oxygenase is expressed by a heterologous nucleic acid. In certain particularly preferred embodiments, the photoactive holophytochrome is not a phytofluor, while in other preferred embodiments, the photoactive holophytochrome is a phytofluor. The apophytochrome can be expressed as a fusion protein with a protein that is to be labeled with the phytofluor or holophytochrome. In certain preferred embodiments, the method comprises expressing the ferredoxin-dependent bilin reductase pebA and/or pebB. In a particularly preferred embodiment the cell is a bacterial cell (*E. coli*). The method can further involve recovering the photoactive holophytochrome or phytofluor from the cell.

In another embodiment this invention provides a cell (e.g., an algal cell, a yeast cell, a bacterial cell, a plant cell, an insect cell, and a mammalian cell) comprising: a heme oxygenase; an apophytochrome; and a ferredoxin-dependent bilin reductase; whereby the cell produces a photoactive holophytochrome and where one or more of the apophytochrome and the ferredoxin-dependent bilin reductase are expressed by heterologous nucleic acids. The ferredoxin-dependent bilin reductase is preferably an HY2 family bilin reductase (e.g. HY2, pcyA, etc.). In certain embodiments, the apophytochrome and the ferredoxin-dependent bilin reductase are both expressed by heterologous nucleic acids. They can both be expressed by the same heterologous nucleic acid. In certain cells the heme oxygenase is an endogenous heme oxygenase. In other cells, the heme oxygenase is expressed by a heterologous nucleic acid. The expressed holophytochrome is, in certain embodiments, not a phytofluor and, in other embodiments, is a phytofluor. Certain preferred cells express pebA and/or pebB. One preferred cell is a bacterial cell (e.g. *E. coli*).

This invention also provides an isolated nucleic acid comprising: a nucleic acid encoding a heme oxidoreductase; and a nucleic acid encoding and a ferredoxin-dependent bilin reductase; where the nucleic acid expresses a functional heme oxidoreducase and a functional bilin reductase. The heme oxidoreductase and the bilin reductase can be under control of the same, or different, promoters. The promoter can include a constitutive promoter, an inducible promoter, or a tissue-specific promoter. The nucleic acid can be present in a cell (e.g. a bacterial cell, a plant cell, a yeast cell, a mammalian cell, an insect cell, etc.). Preferred nucleic acids include one or more genes selected from the group consisting of HO1, HY2, PcyA, PebA, and PebB. One preferred nucleic acid comprises an HO1 coding region and/or a pcyA coding region and/or a pcyB.

Definitions.

The term "fluorescent adduct" refers to a fluorescent molecule (i.e., one capable of absorbing light of one wavelength and emitting light of a second wavelength) comprising an "apoprotein" (also referred to as an apophytochrome) component joined to a "bilin" component, both of which are described below. The fluorescent phytochrome-bilin conjugates (e.g., phytochrome-PEB adducts), are also referred to herein as "phytofluors". The manner in which the two components are joined to form an adduct is irrelevant to the present invention. Typically, the two components spontaneously form an adduct through covalent interactions. The components may also be deliberately linked through covalent bonds (e.g., through the use of crosslinking reagents). The fluorescent adducts of this invention do not require pairing of an apoprotein with its corresponding native bilin. To the contrary, the invention contemplates adducts consisting of naturally occurring or engineered apoproteins with bilins derived from different organisms, or with non-naturally occurring synthetic linear oligopyrroles or oligopyrrole mimetics.

The terms "apoprotein", "apophytochrome", or "apoprotein polypeptide", as used herein, refer to polypeptides derived from eukaryotes, such as vascular plants, non-vascular plants, and algae, or from prokaryotes, such as cyanobacteria and prochlorophytes. The term encompasses both naturally occurring apoproteins and variant polypeptides, e.g. derived through mutagenesis. The apoproteins have a hydrophobic pocket, referred to as chromophore binding site, capable of forming an adduct with a bilin component. The apoproteins of the invention are typically homodimeric proteins about 1100 amino acids in length, each subunit being composed of two major domains. The globular 70 kD N-terminal domain contains the hydrophobic pocket, while the more elongated 55 kD carboxyl terminal domain contains the sites at which the two subunits are associated. Preferred analogues are recognized by and thus comprise the consensus sequence of FIG. 6 in U.S. Pat. No. 6,046,014. The apoprotein can be derived from vascular and non-vascular plants, green alga, or bacteria, can be recombinantly expressed, or can be chemically synthesized de novo. Preferred apoproteins are encoded by plant genes, algal genes, bacterial genes, or cyanobacterial genes. Particularly preferred apoproteins include any of the apoproteins described herein or in U.S. Pat. No. 6,046,014 or those listed in the sequence listing of U.S. Pat. No. 6,046,014 or conservative substitutions of these sequences. Most preferred apoproteins include apoproteins from plants (e.g., oats with an apoprotein having about 1100 amino acid residues), green algae (e.g., *Mesotaenium caldariorum*), or cyanobacteria (as illustrated in U.S. Pat. No. 6,046,014), or related, proteins having conservative substitutions. Truncated apoproteins consisting of a chromophore domain; the apoprotein N-terminal subsequence sufficient for lysase activity are particularly preferred. One preferred N-terminal subsequence consists of less than about 600 N-terminal amino acids, more preferably less than about 515 N-terminal amino acids, and most preferably less than about 400 N-terminal amino acids. Apophytochromes can be readily identified by one of skill in the art by comparison of the polypeptide sequence in question with the apophytochrome consensus sequence provided in FIG. 6 of U.S. Pat. No. 6,046,014 using standard sequence comparison methodologies. For a general discussion of apoprotein structure and function, see, Quail et al. (1997) *Plant Cell and Environment*, 20: 657–665.

The "bilin" components of the adducts of the invention are linear polypyrroles (e.g., di-, tri-, or tetrapyrroles) capable of fluorescing, or photointerconverting between spectrophotometrically distinct forms, when associated with an apoprotein. Typically, the bilin components of the invention are isolated from vascular plants, algae, or cyanobacteria according to standard techniques. The bilin components can also be synthesized de novo. For a general discussion of bilins useful in the present invention see, Falk (1989) Pp. 355–399 In: *The Chemistry of Linear Oligopyrroles and Bile Pigments*., Springer-Verlag, Vienna.

The term "chromophore domain" or "minimal chromophore domain" refers to the apoprotein N-terminal subsequence sufficient for lyase activity; the ability to spontaneously assemble in the presence of a bilin to form a phytofluor. Chromophore domains typically comprise less than 600 amino acids of the N terminus of the apoprotein, preferably less than about 515 amino acids, more preferably less than about 450 amino acids and most preferably less than about 400, 390, 350 or even as few as 197 N-terminal amino acids known as the "bilin lyase domain", see Wu and Lagarias (2000) *Biochemistry* 39: 13487–13495. One preferred chromophore domain comprises the 514 N-terminal amino acids of a cyanobacterial phytochrome.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

The terms "isolated" "purified" or "biologically pure" refer to material which is substantially or essentially free from components which normally accompany it as found in its native state. With respect to nucleic acids and/or polypeptides the term can refer to nucleic acids or polypeptides that are no longer flanked by the sequences typically flanking them in nature.

The term "recombinant" or "recombinantly expressed" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

An "HY2-related gene" or a "member of the HY2 family" refers to a gene that encodes a ferredoxin-dependent bilin reductase and that that can catalyze a two or four electron reduction of a linear tetrapyrrole to the biologically active precursors of the chromophores of phytochromes and phycobiliproteins. Typically 200–300 amino acids in length, these enzymes can be recognized by the characteristic signature sequence depicted in FIGS. 5 and 10.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology— Hybridization with Nucleic Acid Probes part I chapter 2 Overview of principles of hybridization and the strategy of nucleic acid probe assays*, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term conservative substitution is used herein to refer to replacement of amino acids in a protein with different amino acids that do not substantially change the functional properties of the protein. Thus, for example, a polar amino acid might be substituted for a polar amino acid, a non-polar amino acid for a non-polar amino acid, and so forth. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), and Tryptophan (W).

BRIEF DESCRIPTION OF THE DRAWINGS

FIGS. 3A and 3B illustrate the HY2 locus of *Arabidopsis*. FIG. 3A shows a map of the region of chromosome 3 containing HY2. Two distinct mapping populations were screened, and mapping results with molecular markers are summarized schematically, indicating that HY2 lies in a region 66 kb in length. Markers starting with the letter c are CAPS markers developed during this study. DNA sequence information for bacterial artificial chromosomes (BACs) MZB10 and F3L24 is available in GenBank/EMBL/DDBJ. The HY2 gene structure with mutations is illustrated at the bottom. Exons are depicted as dark boxes and thick lines, which reflect coding regions and 59/39 untranslated regions, respectively. Dotted lines indicate introns. FIG. 3B shows the genomic sequence of HY2 (SEQ ID NO:32) and the deduced HY2 protein sequence (SEQ ID NO:33) from the Columbia (Col) ecotype. Uppercase letters represent exons determined by sequence analysis of HY2 cDNAs. Introns and spacer sequences are indicated with lowercase letters. The stop codon is double underlined. Mutations in hy2 alleles are shown in boldface letters. Single nucleotide polymorphisms in both Ler and Wassilewskija (Ws) ecotypes include the following: inserted T (at nucleotide 234), G364T conversion with amino acid change to Asn, and G1182A conversion (silent). Single nucleotide polymorphisms in the Ler ecotype only include the following: C515A (in intron), G884A (silent), C1145T (in intron), and G1717A (in intron). The single nucleotide polymorphism in Ws ecotype only is C1910T (silent).

FIG. 4A: Total RNA (10 mg) from 1-week-old seedlings was analyzed by RNA gel blotting using the MZB10.18/F3L24.1 cDNA as a probe. RNA was prepared from seedlings of the hy2 mutants and corresponding wild-type plants. FIG. 4B: The same RNA gel blot was probed with rDNA as a loading control of RNA.

FIG. 5 shows an alignment of HY2 and HY2-Related Proteins. Alignment of the HY2 protein (SEQ ID NO:34) with proteins of unknown function from oxygenic photosynthetic bacteria identified by PSI BLAST. Conserved residues in 100 or 80% of the aligned sequences are depicted in the consensus sequence with uppercase or lowercase letters, respectively. Sequence similarity groups shown in the consensus sequence reflect conservation in 100% of the sequences. These are labeled as follows: 1, D 5 N; 4, R 5 K; 5, F 5 Y 5 W; and 6, L 5 I 5 V 5 M. Dark shading with white letters, gray shading with white letters, and gray shading with black letters reflect 100, 80, and 60% sequence conservation, respectively. Sequence identifiers correspond to hypothetical proteins from *Synechococcus* sp WH8020 (YCP2_SYNPY (SEQ ID NO:35) and YCP3_SYNPY) (SEQ ID NO:36), from *Prochlorococcus* (YHP2_PROMA (SEQ ID NO:37) and YHP3_PROMA) (SEQ ID NO:38), and from *Synechocystis* sp PCC 6803 gene (cyanobase locus slr0116 (SEQ ID NO:39); see http://www.kazusa.or.jp/cyano/cyano.html). Database accession numbers are AB045112 for HY2 (DDBJ), Q02189 for YCP2_SYNPY (SWISSPROT), Q02190 for YCP3_SYNPY (SWISSPROT), CAB95700.1 for YBP2_PROMA (EMBL), CAB95701.1 for YIP3_PROMA (EMBL), and S76709 for slr0116 (Protein Information Resource). Asterisks are indicated every 20 residues.

FIGS. 6A to 6C: Cells expressing GFP (onion) (FIG. 6A), the HY2 chloroplast transit peptide fused to GFP (HY2TP-GFP) (onion) (FIG. 6B), and HY2TP-GFP (tobacco) (FIG. 6C) were analyzed by fluorescence microscopy using the green channel for GFP. FIG. 6D: The same sample as in (C) imaged using the red channel for chlorophyll. Bars in (6A) and (6B) 5 100 mm; bars in (6C) and (6D) 5 10 mm.

FIG. 10 shows a multiple sequence alignment of the identified bilin reductases. All identified sequences were aligned using the programs CLUSTAL W and MEME. Conserved residues in 90 or 70% of the aligned sequences are depicted in the consensus sequence with uppercase or lowercase letters, respectively. Sequence similarity groups, labeled 1 (D, E), 2 (R, K), 3 (F, Y, W), and 4 (L, I, V, M), shown in the consensus sequence reflect conservation in >90% of the sequences. Dark shading with white letters, gray shading with white letters, and gray shading with black letters reflect 90, 70, and 50% sequence conservation, respectively. SYNY3, *Synechocystis* sp PCC6803; SYNPY, *Synechococcus* sp WH8020; SYN81, *Synechococcus* sp WH8102; PROMA, *Prochloroccocus* sp SS120; PROME, *Prochloroccocus* sp MED4; NOSPU, *Nostoc punctiforme*; ANASP, *Anabaena* sp PCC7120; ARATH, *Arabidopsis thaliana*; and HORVU, *Hordeum vulgare*. Database accession numbers are GB: AF339056 for PcyA_ANASP (SEQ ID NO:40) (CyanoBase contig 362), GB: AF339057 for PcyA_NOSPU (SEQ ID NO:41) (JGI contig 632), PIR: S76709 for PcyA_SYNY3, (SEQ ID NO:42), PcyA_SYN81 (SEQ ID NO:43) is on JGI contig 51, GB: AF352050 for PcyA_PROME (SEQ ID NO:44) (JGI contig 26), SW: Q02189 for PebA_SYNPY (SEQ ID NO:45), PIR: S31075 (fragment)/JGI contig 72 for PebA_SYN81 (SEQ ID NO:46), EMB: CAB95700.1 for PebA_PROMA (SEQ ID NO:47), PebA_PROME (SEQ ID NO:48) is on JGI contig 26, GB: AF352049 for PebA_NOSPU (SEQ ID NO:49) (JGI contig 622), SW: Q02190 for PebB_SYNPY (SEQ ID NO:50), PebB_SYN81 (SEQ ID NO:51) is on JGI contig 72, EMB: CAB95701.1 for PebB_PROMA (SEQ ID NO:52), PebB_PROME (SEQ ID NO:53) is on JGI contig 26, GB: AF339058 for PebB_NOSPU (SEQ ID NO:54) (JGI contig 622), DDBJ: AB045112 for HY2_ARATH (SEQ ID NO:55), EMB: CAB77705.1 for RCCR_HORVU (SEQ ID NO:56), EMB: CAB16763.1 for RCCR_ARATH (SEQ ID NO:57). Asterisks indicate every tenth amino acid; dashes indicate gaps; numbers above the line indicate amino acid sequence numbering starting with number one.

FIG. 13A: BV was incubated with a soluble protein extract of isopropylb thiogalacto pyranoside-induced *E. coli* DH5a strain carrying pGEXNN under standard PFB synthase assay conditions for 30 min at 28° C. under green safe light. Recombinant apoCph1 was added to the reaction and incubated for additional 30 min at room temperature under green safelight, and a phytochrome difference spectrum was obtained. The difference spectrum shown as a solid line was obtained with apoCph1 incubated with PcyA_SYNY3 metabolites, the spectrum shown in dashed lines was obtained with mHY2 metabolites. Absorption maximum and minimum were indicated as nm. Neither PebA_SYNPY, PebB_SYNPY, or a mixture of both was able to form a photoconvertible holophytochrome (no difference spectrum shown). FIG. 13B: Phytofluor fluorescence spectra of recombinant cyanobacterial phytochrome (Cph1) incubated with PebA and PebB metabolites. The fluorescence excitation and emission spectra of the phytofluor were obtained after incubation of apoCph1 with the reaction metabolites of PebA_SYNPY and PebB_SYNPY. The solid line represents the excitation spectrum monitored with an emission wavelength of 590 nm. The dashed line shows the emission spectrum obtained with an excitation wavelength of 545 nm.

DETAILED DESCRIPTION

This invention pertains to the isolation and characterization of a family of bilin reductases (designated herein as the HY2 family). In certain embodiments, these bilin reductases catalyze the conversion of a biliverdin to a phytobilin and form a component of a phytochrome biosynthetic pathway. The bilin reductases of this invention can be used in vivo or in vitro to simply convert biliverdins to phytobilins or, in conjunction with other enzymes in the phytochrome synthetic pathway to synthesize complete phytochromes and/or phytofluors. This invention also pertains to the recombinant synthesis of a phytochrome or phytofluor.

Figure 1:
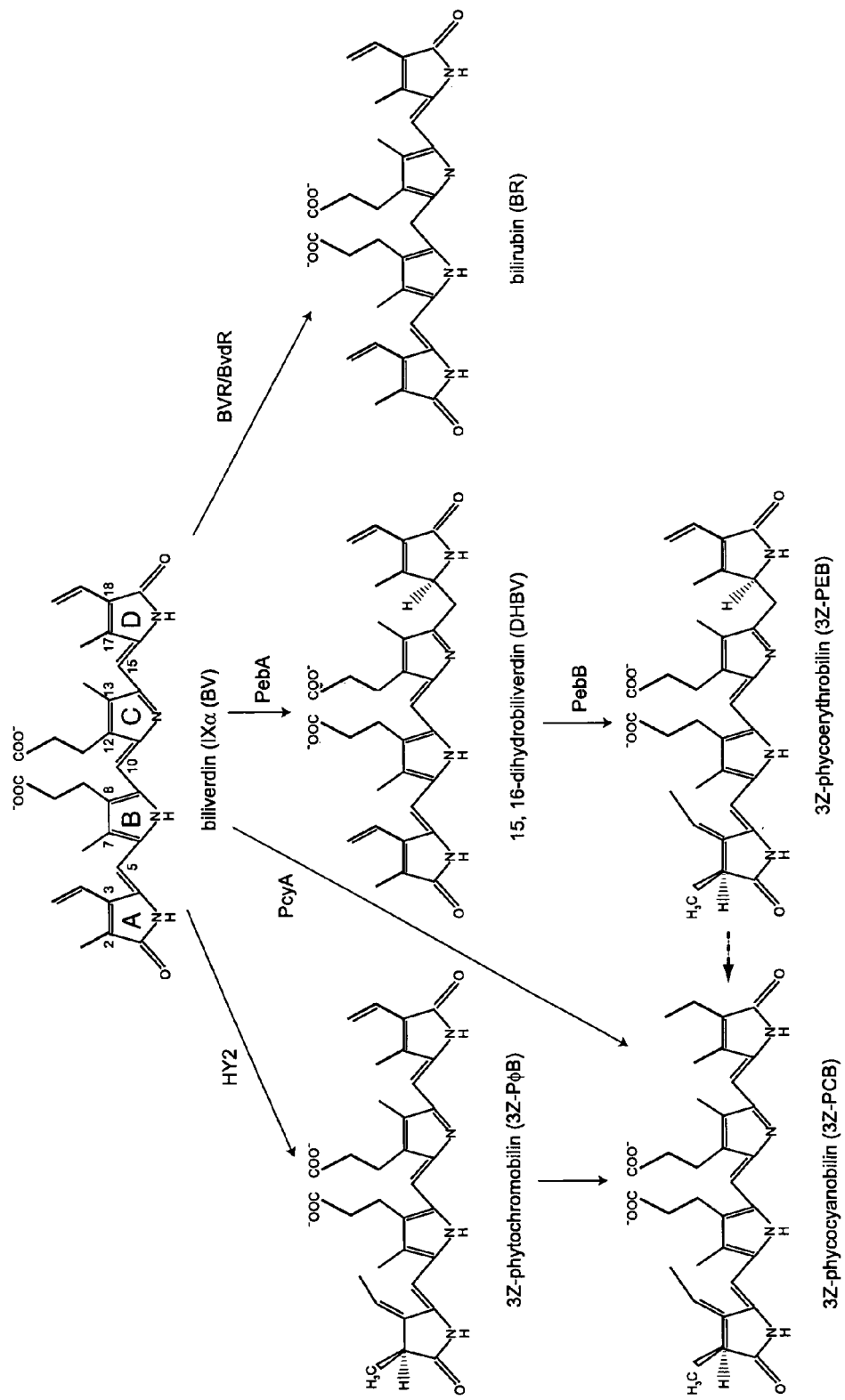
FIG. 1 illustrates a pathway for the biosynthesis of bilin pigments. The mammalian bile pigment bilirubin and the linear tetrapyrrole precursors of the phytochrome and phycobiliprotein chromophores of plants, algae, and cyanobacteria share the common intermediate biliverdin IXa. HY2, phytochromobilin synthase or 3Z-phytochromobilin:ferredoxin oxidoreductase; PcyA, 3Z-phycocyanobilin:ferredoxin oxidoreductase; PebA, 15,16-dihydrobiliverdin:ferredoxin oxidoreductase; PebB, 3Z-phyco-erythrobilin:ferredoxin oxidoreductase; BVR/BvdR, biliverdin IXa:NAD(P)H oxidoreductase. The dashed arrow with a question mark indicates a second type of putative 3Z-phycocyanobilin:ferredoxin oxidoreductase. The dashed arrow indicates a putative phycoerythrobilin-phycocyano-bilin isomerase (Beale and Cornejo (1991) *J. Biol. Chem.* 266:22333–22340).

The phytochrome chromophore biosynthetic pathway shown in FIG. 1 has been elucidated by the classical approach of overcoming a blocked step with exogenous putative intermediates (Terry et al. (1993) *Arch. Biochem. Biophys.*, 306:1–15) and by analysis of phytochrome-chromophore deficient mutants (Terry (1997) *Plant Cell Environ.*, 20: 740–745). This pathway shares common intermediates with heme and chlorophyll biosynthesis to the level of protoporphyrin IX, at which point the latter two pathways diverge by metallation with iron or magnesium (Beale (1993) *Chemical Rev.*, 93:785–802; Porra (1997) *Photochem. Photobiol.*, 65:492–516; Reinbothe and Reinbothe (1996) *Eur. J. Biochem.*, 237:323–343). As shown FIG. 1, heme is converted to biliverdin IXα (BV), the first committed intermediate in the biosynthethic pathways of the chromophores of the phytochromes and of the light-harvesting phycobiliproteins in cyanobacteria, red algae and cryptophytes. This reaction is accomplished by a ferredoxin-dependent heme oxygenase in red algae and cyanobacteria (Rhie and Beale (1995) *Arch. Biochem. Biophys.*, 320: 182–194; Cornejo and Beale (1997) *Photosynthesis Res.*, 51:223–230) and by an enzyme in plants that is likely to be similar in structure (Terry (1997) *Plant Cell Environ.*, 20: 740–745). This contrasts with heme oxygenases found in mammalian systems that utilize cytochrome P450 reductase for the oxygen-requiring conversion of heme to BV (Maines (1997) *Annl. Rev. Pharmacol. and Toxicol.*, 37: 517–554).

As illustrated in Scheme 1 (FIG. 1), the metabolic fate of BV differs in green plants, cyanobacteria and mammals, with BV being metabolized by different reductases with unique double bond specificities. Mammalian biliverdin IXα reductase (BVR), an NAD(P)H-dependent enzyme that catalyzes the reduction at the C10 methine bridge to produce bilirubin (BR), was the first to be discovered (Singleton and Laster (1965) *J. Biol. Chem.*, 240: 4780–4789). Mammalian BVRs are small soluble enzymes consisting of a single NAD(P)H and bilin binding subunit (Kutty and Maines (1981) *J. Biol. Chem.*, 256: 3956–3962; Maines and Trakshel (1993) *Arch. Biochem. Biophys.*, 300: 320–326). Active recombinant versions of rat and human BVRs have been cloned and expressed in *E. coli* (Fakhrai and Maines (1992) *J. Biol. Chem.*, 267: 4023–4029; McCoubrey and Maines (1994) *Eur. J. Biochem.*, 222: 597–603; Maines et al. (1996) *Eur. J. Biochem.*, 235: 372–381). The unexpected discovery of the gene bvdR in the cyanobacterium *Synechocystis* sp PCC 6803, which encodes a BVR that also catalyzes the NADPH-dependent reduction of the C10 methine bridge of BV (Schluchter and Glazer (1997) *J. Biol. Chem.*, 272: 13562–13569), has established that this enzyme has ancient evolutionary origins. Interestingly, bvdR plays a key role in the regulation of phycobiliprotein biosynthesis in this cyanobacterium since its inactivation leads to reduced accumulation of phycocyanin (Schluchter and Glazer (1997) *J. Biol. Chem.*, 272: 13562–13569).

Cyanobacteria possess additional bilin reductases for the synthesis of the linear tetrapyrrole precursors of their phycobiliprotein light-harvesting antennae complexes (Cornejo and Beale (1997) *Photosynthesis Research*, 51: 223–230). Based on this investigation and previous studies with the red alga *Cyanidium caldarium* (Beale and Cornejo (1991) *J. Biol. Chem.*, 266: 22328–22332; Beale and Cornejo (1991) *J. Biol. Chem.*, 266: 22333–22340; Beale and Cornejo (1991) *J. Biol. Chem.*, 266: 22341–22345), Beale and colleagues have proposed that the biosynthesis of the phycobiliprotein chromophore precursors, phycoerythrobilin (PEB) and phycocyanobilin (PCB), involves two ferredoxin-dependent bilin reductases. The first of these enzymes catalyzes the reduction of BV at the C15 methine bridge to give 15,16-dihydrobiliverdin (i.e. DHBV synthase), while the second reduces 15,16-dihydrobiliverdin (DHBV) at the C2 double bond to produce 3Z-PEB (see Scheme 1). In *Cyanidium*, an additional enzyme appears to mediate the isomerization of 3Z-PEB to 3Z-PCB, both of which appear to be further isomerized to their corresponding 3E isomers prior to assembly with the nascent phycobiliprotein apoproteins.

By contrast with mammals and phycobiliprotein-containing organisms, BV is reduced at the C2 double bond in plants and green algae to yield 3Z-PΦB by the ferredoxin-dependent enzyme PΦB synthase (Terry et al. (1995) *J. Biol. Chem.*, 270:11111–11118; Wu et al. (1997) *J. Biol. Chem.*, 272:25700–25705). In both higher and lower plants (e.g. mosses, ferns), 3Z-PΦB and/or its 3E-isomer have been established to be the immediate precursor of the phytochrome chromophore (Terry et al. (1993) *Arch. Biochem. Biophys.*, 306: 1–15). Recent studies have established that PCB is the natural phytochrome chromophore precursor in the green alga *Mesotaenium caldariorum*, and both PΦB synthase and PΦB reductase, the enzyme that catalyzes the reductive conversion of 3Z-PΦB to 3Z-PCB, have been detected in soluble protein extracts from the chloroplast of this organism (Wu et al. (1997) *J. Biol. Chem.*, 272:25700–25705). While a 3Z to 3E PΦB isomerases have been hypothesized, this enzyme has not been identified in plant extracts (Terry et al. (1993) *Arch. Biochem. Biophys.*, 306: 1–15; Beale (1993) *Chemical Rev.*, 93:785–802). The final step of phytochrome chromophore biosynthesis is the covalent attachment of PΦB or PCB to apophytochrome.

Biochemical analysis of known phytochrome chromophore-deficient mutants, which include the hy1 and hy2 mutants of *A. thaliana* (Koornneef et al. (1980) *Zeitschrift fur Pflanzenphysiology*, 100:147–160; Chory et al. (1989) *Plant Cell*, 1:867–880), the aurea and yg2 mutants of tomato (Koornneef et al. (1985) *J. Plant Physiol.*, 120:153–165; Van Tuinen et al. (1996) *Plant Journal*, 9:173–182; Terry and Kendrick (1996) *J. Biol. Chem.*, 271:21681–21686), the pcd1 and pcd2 mutants of pea (Weller et al. (1996) *Plant Cell*, 8: 55–67; Weller et al. (1997) *Plant J.*, 11: 1171–1186), supports the conclusion that these mutations reflect lesions in the structural genes for either heme oxygenase or PΦB synthase (reviewed in Terry (1997) *Plant Cell Environ.*, 20: 740–745). Indeed, the HY1 locus of *Arabidopsis* has been shown to encode a ferredoxin-dependent heme oxygenase.

This invention pertains to the cloning and sequence analysis of HY2 and the demonstration that the HY2 locus encodes phytochromobilin synthase, a ferredoxin-dependent bilin reductase enzyme that converts BV to PΦB. In addition it is demonstrated that protein relatives of HY2 are also biliverdin (BV) reductases.

I. HY2 and HY2 Family Members.

A) HY2.

The genomic sequence of HY2 and the protein sequence are provided in FIG. 3B. Based on cDNA sequence analysis, the HY2 protein contains 329 residues with a calculated molecular mass of 38.1 kD. At its N terminus, the HY2 protein sequence is rich in serine, with few acidic residues (six serine and one aspartic acid among 45 residues), which suggests a possible transit peptide for localization to plastids (Gravel and von Heijne (1990) *FEBS Lett.* 261: 455–458). The second amino acid after the initiation methionine is alanine, which is often observed in plastid transit peptides.

The program CHLOROP was also used to predict the transit peptide of HY2, and it indicated that the first 45 amino acid residues of the HY2 protein form a chloroplast transit peptide (Emanuelsson et al. (1999) *Protein Sci.* 8: 978–984; http://www.cbs.dtu.dk/services/ChloroP/).

The calculated molecular mass of the mature HY2 protein is 33.0 kD and its predicted pI is 5.66, which are similar to those of PΦB synthase purified from oat seedlings. The HY2 protein has no predicted transmembrane helices, which is also consistent with the observation that oat PΦB synthase is a soluble protein.

B) The HY2 Family and Family Members.

Using the HY2 protein sequence as a query sequence, HY2 family members are identified using an iterative PSI-BLAST search of the nonredundant GenBank/EMBL database, e.g. using default search parameters (Altschul et al. (1997) *Nucleic Acids Res.* 25, 3389–3402). No HY2-related gene was identified by this search in the nearly complete *Arabidopsis* genome. In contrast, this search identified HY2-related sequences from two marine cyanobacteria, *Prochlorococcus marinus* sp. SS120 (EMBL accession numbers CAB95700.1 and CAB95701.1) and *Synechococcus* sp. WH8020 (SWISS-PROT accession numbers Q02189 and Q02190), and a related protein sequence from the cyanobacterium *Synechocystis* sp. PCC 6803 (cyanobase locus slr0116; Protein Information Resource accession number S76709).

Both marine cyanobacteria possess two HY2-related ORFs that appear to be part of multigene operons. The *Synechococcus* ORFs, ycp2_synpy and ycp3_synpy, are located within a cluster of genes involved in phycobiliprotein biosynthesis (Wilbanks and Glazer (1993) *J. Biol. Chem.* 268: 1226–1235), whereas the *Prochlorococcus* ORFs, which we term yhp2_proma and yhp3_proma, are located immediately downstream of a gene related to heme oxygenase (GB:AJ278499.1). These observations suggest that these genes are involved in phycobilin biosynthesis.

Figure 10A:
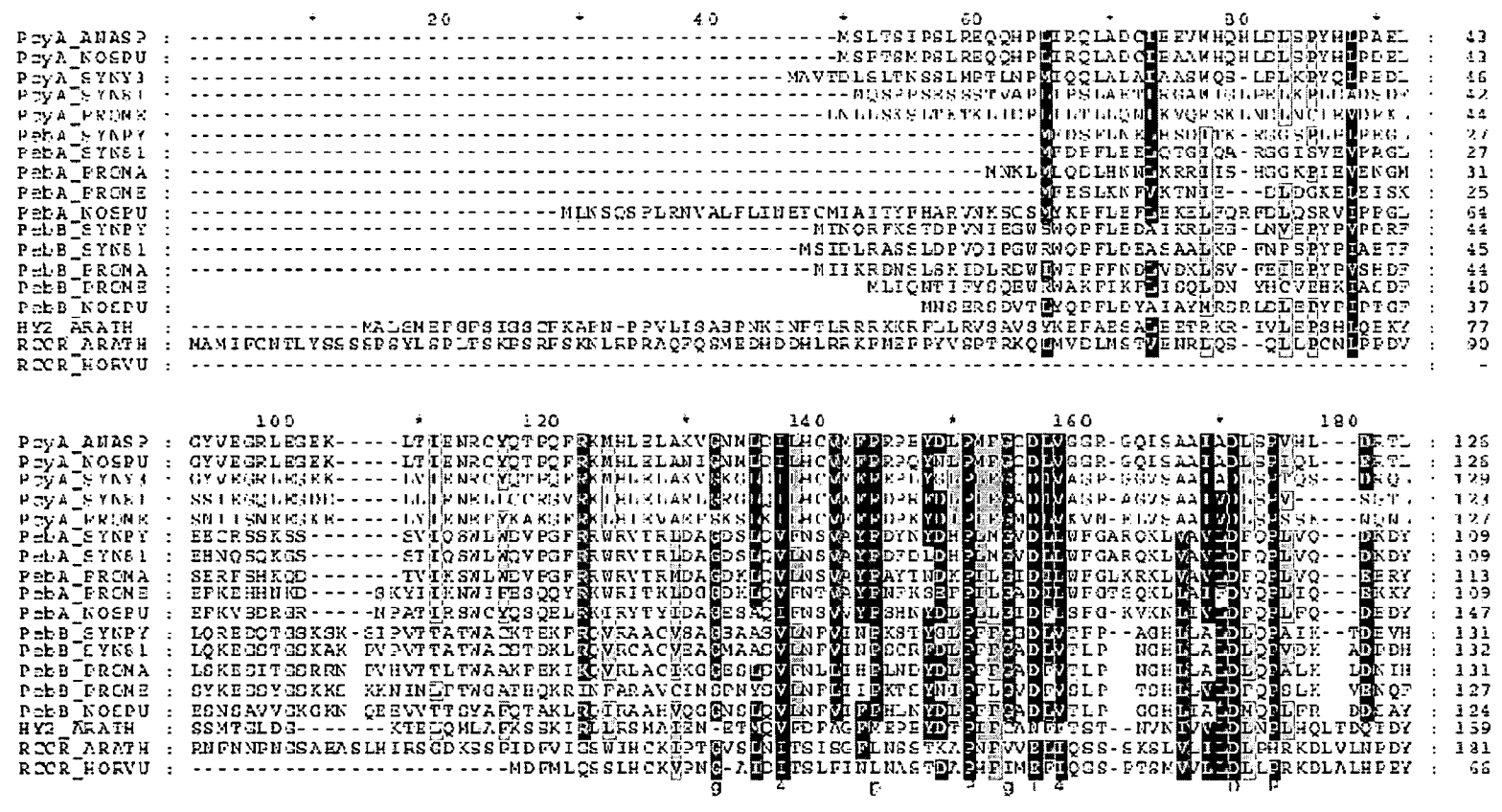
Figure 10B:
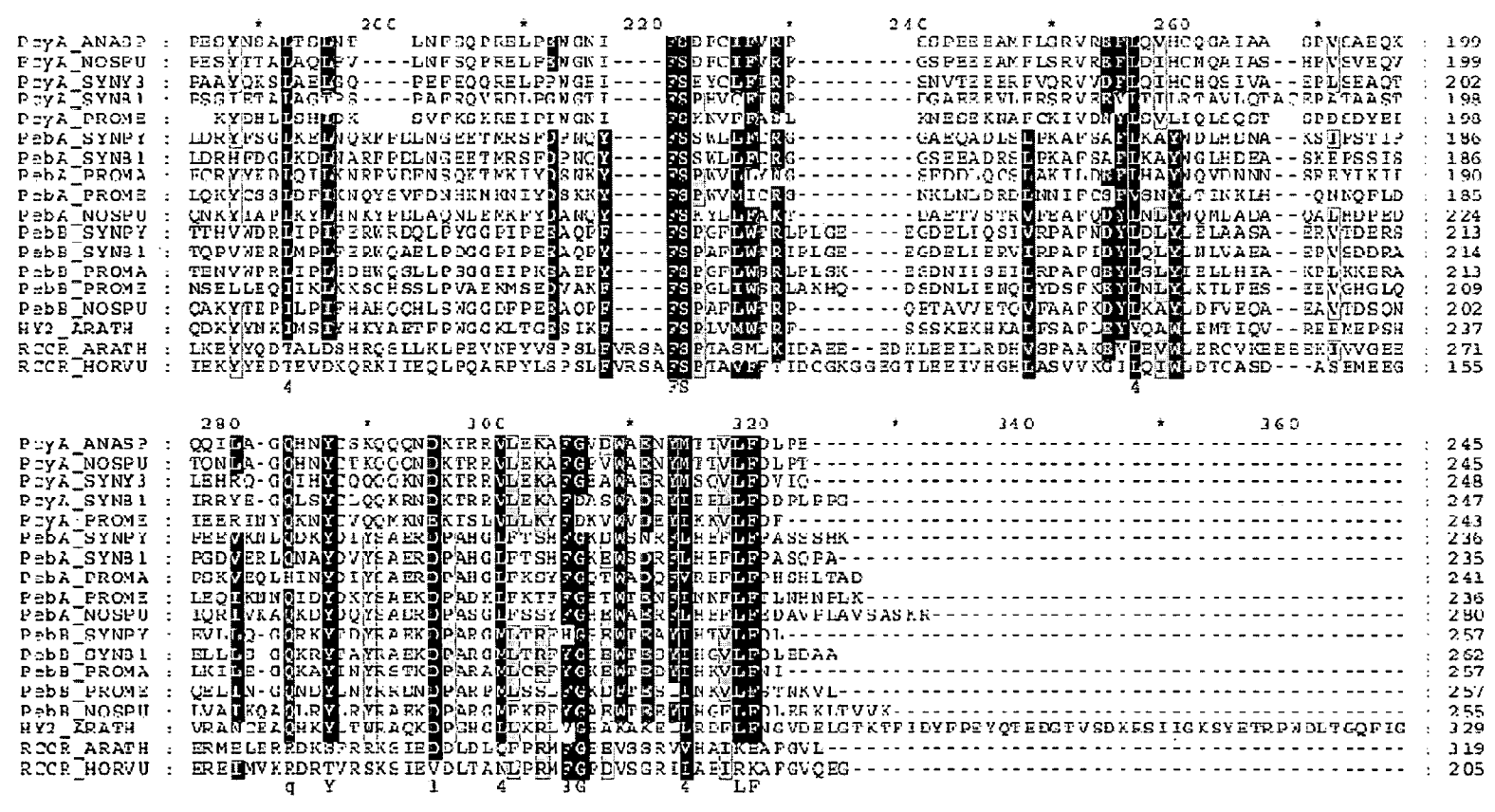

Examination of highly conserved residues in the entire HY2 family and those within each of the five classes of bilin reductases provides information regarding residues important to the protein structure, ferredoxin interaction site, and substrate/product specificity. In this regard, only a small number of residues are conserved in the entire HY2 family of enzymes. These include hydrophobic residues at positions 137, 157, 158, 256, and 314, Pro151, Phe221, Ser222, and Asp171 (FIG. 10). The notable lack of conserved basic residues suggests that the propionyl moieties of the bilin substrates do not form salt linkages with the enzymes. The conserved hydrophobic residues proline and phenylalanine are likely to be involved in overall protein structure (i.e., folding). Alternately, they may form hydrophobic interactions with conserved regions of the various bilin substrates.

The loss-of-function hy2-1 and hy2-104 alleles of phytochromobilin synthase from *Arabidopsis* support the critical role of Pro151 in HY2's structure. The conserved serine and aspartate residues likely play catalytic roles, such as hydrogen bonding with the substrate and/or substrate protonation to make the bound bilin a better electron acceptor. Despite the wide divergence of the HY2 family, we believe that these conserved residues indicate that the active sites of all members of this class are similar. We believe the distinct doublebond reduction specificities of the BV reductases (i.e., PcyA, PebA, HY2), the 15,16-DHBV reductases (i.e., PebB), and the RCCR families reflect the positioning of the respective substrates within the catalytic pocket. Because the A/B and C/D rings of BV are very similar but not identical, it is conceivable that the substrate binding sites of the PebA and HY2 enzymes are tailored to position BV in opposite orientations, favoring electron transfer to the bilin C/D ring or A ring, respectively. If this is true, then the PebB class might tether its 15,16-DHBV substrate in an orientation similar to that of the HY2 family, whereas RCC might be bound to RCCR in a manner similar to that in which BV is bound to PebA.

1) pcvA

We have documented that the pcyA genes of the cyanobacteria *Synechocystis* sp PCC6803, *Anabaena* sp PCC7120, and *Nostoc punctiforme* encode bilin reductases that catalyze the four electron reduction of BV to 3Z-PCB. PCB is the precursor of the chromophores of the phycobiliproteins phycocyanin and allophycocyanin, which are abundant in all three cyanobacteria. PcyA enzymes are atypical bilin reductases because all others catalyze two-electron reductions. Formally, these enzymes catalyze two electron reductions of both the A and D rings of BV; however, we have not detected the production of semireduced intermediates such as PΦB and $18^1,18^2$-DHBV. Thus, it appears that the partially reduced intermediates are tightly bound to the enzyme. The direct conversion of BV to PCB in these cyanobacteria is in contrast to the proposed pathways of PCB biosynthesis in the red alga *C. caldarium*, which involves the intermediacy of PEB, and in the green alga *M. caldariorum*, in which 3Z-PΦB is an isolable intermediate. pcyA-related genes also are present in the oxyphotobacterium *Prochlorococcus* sp. MED4, an unanticipated observation in view of the lack of phycobiliproteins in this organism. We were able to clone the *Prochlorococcus* sp. MED4 pcyA gene and express it as an N-terminal GST fusion. We determined that recombinant PcyA_PROME was able to reduce BV to PCB in our standard phytochrome-based assay (data not shown). It therefore possesses the same enzymatic activity as other studied PcyA enzymes.

2) pebA and pebB

We have observed that the pebA and pebB genes of the cyanobacteria *Synechococcus* sp WH8020 and *N. punctiforme* encode bilin reductases that catalyze the conversions of BV to 15,16-DHBV and 15,16-DHBV to 3ZPEB, respectively (FIG. 1). PebA therefore is a 15,16-DHBV:ferredoxin oxidoreductase, whereas PebB is a 3Z-PEB:ferredoxin oxidoreductase. Both activities are consistent with the pathway of PEB biosynthesis in the red alga *C. caldarium*. The two peb genes also are found in the same operon in both phycoerythrin-producing cyanobacteria, and their close association with the major phycobiliprotein gene clusters supports their role in phycobilin biosynthesis.

Without being bound to a particular theory, we believe PebA and PebB function as a dual enzyme complex, in view of the synergistic metabolism of BV observed when the two enzymes are coincubated. A peb operon is not present in the genome of the cyanobacterium *Synechocystis* sp PCC6803, an organism that lacks phycoerythrin. This strongly suggests that PCB is synthesized in this cyanobacterium via the PcyA-dependent pathway, as opposed to the PEB pathway found in *C. caldarium*. In this regard, biochemical analyses of crude extracts from *Synechocystis* sp PCC6803 provide no evidence for the production of PEB. The MED4 and SS120 subspecies of the oxyphotobacteria *Prochlorococcus* also possess peb operons very similar to those of *Synechococcus* sp WH8020 and WH8102, except that the former possess upstream genes related to heme oxygenase. This strongly suggests that both oxyphotobacterial subspecies can synthesize PEB.

We also believe that *Prochlorococcus* PebA and PebB are likely functional orthologs of the *Synechococcus* and *Nostoc* enzymes. It is likely that numerous bilin isomerases are present in these oxygenevolving photosynthetic organisms.

C) Identification of other Members of the HY2 Family.

Other members of the HY2 family of bilin reductases can readily be identified using the methods described herein (see e.g., Example 2). In a preferred embodiments, such methods involve using alignment algorithms with one or more members of the HY2 family as described herein to search nucleic acid and/or protein databanks to identify related genes/polypeptides.

The activity of the putative bilin reductase can be confirmed, e.g. using a standard bilin reductase activity assay. One such bilin reductase assay is described in detail in Examples 1 and 2. Basically, the putative bilin reductase is combined with a biliverdin in a buffer system compatible with enzyme activity. The assay mixture is incubated for a period of time. Product analysis can be accomplished using a direct HPLC assay (see Example 1) or by a coupled assay after the addition of an appropriate apophytochrome (e.g. recombinant cyanobacterial phytochrome such as Cph1) using spectroscopic methods.

II. Uses for HY2.

The HY2 bilin reductases of this invention are useful tools for applications. The ability to engineer the biosynthesis of phycoerythrobilin (PEB) in any biliverdin-producing organism is now feasible via the introduction of one or two genes. Similarly, photoactive holophytochromes (e.g. bilin pigments bound to apophytochromes) can be produced in any ferredoxin-containing organism.

Coexpression of bilin reductase genes with apophytochromes enables us to produce holophytochromes in a wide number of cell types including, but not limited to algal cells, plant cells, bacteria, yeast, vertebrate cells (including mammalian cells), insect cells, and the like. This facilitates not only three-dimensional structural analysis of phytochrome, but also the reconstruction of phytochrome signaling in a non-plant system in which we can exploit the power of molecular genetic analyses. Recombinantly expressed phytochromes thus present an excellent model system useful for a wide variety studies. Similar approaches has proven invaluable for the structure-function analysis of the steroid hormone receptor family.

By introducing the pcyA gene into wild-type and chromophore-deficient mutant plants, it is possible to change the wavelength specificity of phytochrome, which can favorably alter plant growth and development in the field environment. Introduction of the pebA and pebB genes into plants can shunt the conversion of BV to PEB, yielding photomorphogenetically challenged plants with fluorescent phytochromes. This is especially useful for the analysis of the temporal and spatial patterns of phytochrome expression in plants.

A) In vivo and Ex vivo Conversion of Biliverdin to Phytobilin.

In certain embodiments, the HY2 family of bilin reductases of this invention can be used as simple reagents (reducing agents) to convert a biliverdin to a phytobilin. The enzymes can be used in vivo (e.g. in a plant) in vitro (e.g. in a cell culture), or ex vivo as a simple reagent. Thus, for example, one or more bilin reductases can be contacted with a biliverdin ex vivo in an appropriate buffer system (e.g., typically in the presence of a ferredoxin) resulting in the conversion of the biliverdin to a phytobilin (see, e.g., Example 1). The phytobilin is then readily purified e.g. using HPLC, e.g. as described herein in the Examples.

Alternatively, a host cell can be transfected with a nucleic acid encoding one or more bilin reductases of this invention and/or other components of the phytochrome biosynthetic pathway. The bilin reductases are expressed in the host cell where, in the presence of ferredoxin, they convert a biliverdin to a phytobilin. Such methods can be simply used to produce a phytobilin, or can be used in increase expression/production of a holophytochrome (e.g. by augmenting the phytochrome synthetic machinery already present in a plant cell, algal cell, photoactive bacterial cell, etc.) or a phytofluor.

Preferred host cells are cells that natively provide a heme and/or a heme oxygenase and/or a ferredoxin. Various preferred cells include, in certain embodiments, cells that do not normally produce a phytochrome (e.g. certain bacterial cells, mammalian cells, etc.) and in certain other embodiments, cells that typically express phytochromes (e.g. plant cells, algal cells, etc.).

B) Expression of Holophytochromes.

The bilin reductases, and other enzymes identified herein, can be used to assemble photoactive holophytochromes including photoactive chromophore precursors and fluorescent phytofluor chromophore precursors. It was a surprising discovery of this invention that a cell transfected with nucleic acids encoding the components of a bilin synthetic pathway (e.g., HO1, PcyA, and/or HY2) and a nucleic acid encoding an apophytochrome (e.g. Cph1, native and recombinant oat phytochrome A (ASPHYAST), *Avena sativa* phyA (Asphya), *Arabidopsis* phyA (AtphyA), *Mesotaenium caldariorum* phylb (Mcphylb), *Synechocystis* sp 6803 phy1 (S6803 phy1), and the like (see, U.S. Pat. No. 6,046,014)) will express a phytochromobilin that assembles with the apophytochrome to produce a photoactive holophytochrome (e.g. chromophore or phytofluor).

The holophytochrome, whether chromophore or phytofluor finds a number of uses. In one particularly preferred use, the chromophore or phytofluor are useful as detectable labels (e.g. colorometric or fluorescent labels). Such labels are useful for the visualization, and/or localization and/or isolation of attached ligands. In particularly preferred embodiments, the apophytochrome is expressed as a fusion protein with a polypeptide that it is desired to label. The apophytochrome can be directly fused to the polypeptide or separated by a peptide linker. When the fusion protein is expressed, the apophytochrome component combines with the bilin to produce a chromophore or phytofluor which then acts as a label for the polypeptide.

In particularly preferred embodiments, the holophytochrome is a phytofluor. Phytofluors are fluorescent apophytochrome-bilin conjugates (e.g., apophytochrome-PEB adducts), that are intensely fluorescent, photostable proteins useful as fluorescent labels (e.g. as probes for biological research, see, e.g., U.S. Pat. No. 6,046,014).

In certain embodiment the host cells are transfected with the pebA and pebB genes to shunt the conversion of biliverdin to PEB, yielding a fluorescent phytofluor.

C) Heterologous Holophytochromes as Model Systems.

The methods of this invention can be used to express a holophytochrome in essentially any cell including cells that, in their native state, do not harbor a phytochrome. Cells containing recombinant holophytochrome provide model systems having a wide variety of uses. For example, such cells can be used to screen for agents that alter the activity and/or spectral sensitivity of the phytochrome. In such assays the cells are contacted with the agent(s) in question and then assayed for changes in physiological activity and/or changes in phytochrome localization or conformation and/or changes in spectral characteristics.

Such model systems are also useful for dissecting the metabolic pathways in which phytochromes are involved.

Recombinant holophytochromes of this invention can be introduced into plants, algae, and the like that normally harbor phytochromes as well. Such introduced heterologous phytochromes alter the wavelength specificity plant, which can favorably alter plant growth and development in the field environment. Using such methods the host range of various plants can be improved.

III. Cloning and Expression of HY2 Proteins and Other Enzymes in the Phytochrome Biosynthetic Pathway.

It is often desirable to provide isolated ferredoxin-dependent bilin reductases (e.g. HY2 family members) and/or holophytochromes (e.g. chromophores or phytofluors) of this invention. These polypeptides and/or phytochromes can be used to raise an immune response and thereby generate antibodies specific to the phytochrome or to components of the biosynthetic system which can then be used to localize and/or visualize such elements in cells. In addition, as indicated above, the isolated phytochromes can be coupled to various moieties and act as detectable labels. The enzyme components of the bilin synthetic pathway can be used as chemical reagents.

As explained below, the holophytochromes and components of the phytochrome and/or bilin synthetic pathway can be conveniently produced using synthetic chemical syntheses or recombinant expression methodologies. In addition to the intact full-length polypeptides, in some embodiments, it is often desirably to express immunogenically relevant fragments (e.g. fragments that can be used to raise specific antibodies).

A) De Novo Chemical Synthesis.

The phytochrome pathway components and/or apophytochromes the active bilin lyase domain or other subsequences can be synthesized using standard chemical peptide synthesis techniques. Where the desired subsequences are relatively short (e.g., when a particular antigenic determinant is desired) the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology. Vol. 2: Special Methods in Peptide Synthesis, Part A.*, Merrifield, et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

B) Recombinant Expression.

In a preferred embodiment, the holophytochromes of this invention and/or components of the phytochrome synthetic pathway (e.g. HY2 family reductases) are synthesized using recombinant expression systems. Generally this involves creating a DNA sequence that encodes the desired protein(s), placing the DNA in an expression cassette under the control of a particular promoter, expressing the protein in a host, and, if desired isolating the expressed protein.

1) Nucleic Acids.

Using the information provided herein, (e.g. HY2 family member sequences, primers, etc.) the nucleic acids (e.g., encoding apoproteins, HY2 family reductases, and the like) can be prepared using standard methods known to those of skill in the art. For example, the HY2 family nucleic acid(s) may be cloned, or amplified by in vitro methods, such as the polymerase chain reaction (PCR), the ligase chain reaction (LCR), the transcription-based amplification system (TAS), the self-sustained sequence replication system (SSR), etc. A wide variety of cloning and in vitro amplification methodologies are well-known to persons of skill. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89: 117.

DNA encoding desired proteins (e.g. HY2 family members) described herein can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al.(1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, the nucleic acids of this invention can be cloned using DNA amplification methods such as polymerase chain reaction (PCR) (see, e.g., Example 1). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired sequence (e.g. HY2 sequence) or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information and representative primers are provided herein. Appropriate restriction sites can also be added to the nucleic acid encoding the desired protein or protein subsequence by site-directed mutagenesis. The plasmid containing the desired sequence or subsequence (e.g. HY2 bilin reductase sequence) is cleaved with the appropriate restriction endonuclease and then ligated into the vector encoding the second molecule according to standard methods.

The nucleic acid sequences encoding desired protein or protein subsequences may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and often an enhancer (e.g., an enhancer derived from immunoglobulin genes, SV40, cytomegalovirus, etc.), and a polyadenylation sequence, and may include splice donor and acceptor sequences.

The isolation and expression of an HY2 nucleic acid is illustrated in Examples 1 and 2.

2) Expression Vectors

A nucleic acid of the invention encoding a one or more enzymes of a phytochrome biosynthetic pathway, e.g., as described above, can be incorporated into a recombinant expression vector in a form suitable for expression of the enzyme(s) (and in certain embodiments, assembly of a holophytochrome) in a host cell. The term "in a form suitable for expression of the fusion protein in a host cell" is intended to mean that the recombinant expression vector includes one or more regulatory sequences operably linked to the nucleic acid encoding the enzyme(s) in a manner that allows for transcription of the nucleic acid into mRNA and translation of the mRNA into the subject protein(s). The term "regulatory sequence" is art-recognized and intended to include promoters, and/or enhancers and/o other expression control elements (e.g., polyadenylation signals). Such regulatory sequences are known to those skilled in the art (see, e.g., Goeddel (1990) *Gene Expression Technology: Meth. in Enzymol.* 185, Academic Press, San Diego, Calif.; Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, NY, etc.).

The design of the expression vector may depend on such factors as the choice of the host cell to be transfected and/or particular protein(s) to be expressed. When used in mammalian cells, a recombinant expression vector's control functions are often provided by viral genetic material. Preferred promoters include, but are not limited to CMV immediate early, HSV thymidine kinase, early and late SV40, LTRs from retrovirus, and mouse metallothionein-I. Use of appropriate regulatory elements can allow for high level expression of the polypeptide(s) in a variety of host cells. A number of suitable expression systems are commercially available. In one preferred embodiment, the sequences encoding the desired polypeptide(s) are expressed in TA cloning plasmid, pCR2.1 (Invitrogen), e.g. as described in Example 3.

It will be appreciated that desired polypeptides can be operably linked to constitutive promoters for high level, continuous expression. Alternatively, inducible and/or tissue-specific promoters can be utilized.

In one embodiment, the recombinant expression vector of the invention is a plasmid or cosmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used.

Examples of techniques and instructions sufficient to direct persons of skill through cloning procedures are found in Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, NY; Ausubel et al. (1994) *Current Protocols in Molecular Biology*, Current Protocols, a joint venture between Greene Publishing Associates, Inc. and John Wiley & Sons, Inc., U.S. Pat. No. 5,017,478; and European Patent No. 0,246,864.

3) Host Cells.

The holophytochromes and/or components of the phytochrome biosynthetic pathway can be expressed in virtually any cell. Preferred cells, however, comprise an endogenous heme and/or a ferredoxin or are modified to comprise a heme and/or a ferredoxin. Particularly preferred cells include, but are not limited to algal cells, bacterial cells, yeast cells, plant cells, vertebrate cells, and mammalian cells including human cells.

The holophytochromes and/or components of the phytochrome biosynthetic pathway are expressed in a host cell by introducing nucleic acid encoding the subject polypeptide(s) into the host cell, wherein the nucleic acid is in a form suitable for expression of the subject polypeptide(s) in the host cell. For example, a recombinant expression vector of the invention, encoding the subject polypeptide(s), is introduced into a host cell. Alternatively, nucleic acid encoding the subject polypeptide(s) which is operatively linked to regulatory sequences (e.g., promoter sequences) but without additional vector sequences can be introduced into a host cell.

As used herein, the term "host cell" is intended to include any cell or cell line so long as the cell or cell line is not incompatible with the protein(s) to be expressed, the selection system chosen or the culture system employed. As indicated above suitable cells include, but are not limited to algal cells, bacterial cells (e.g. *E. coli*), yeast cells (e.g., *S. cerevisiae, S. pombe, P. pastoris, K. lactis, H. polymorpha*, see, e.g., Fleer (1992) *Curr. Opin. Biotech.* 3(5): 486–496), fungal cells, plant cells (e.g. *Arabdopsis*), invertebrate cells (e.g. insect cells) and vertebrate cells including mammalian cells. Non-limiting examples of mammalian cell lines which can be used include CHO cells (Urlaub and Chasin (1980) *Proc. Natl. Acad. Sci. USA* 77: 4216–4220), 293 cells (Graham et al. (1977) *J. Gen. Virol.* 36: 59), or myeloma cells like (e.g., SP2 or NSO, see Galfre and Milstein (1981) *Meth. Enzymol.* 73(B):3–46), and the like.

Examples of vectors for expression in yeast *S. cerivisae* include, but are not limited to pYepSec1 (Baldari. et al. (1987) *Embo J.* 6: 229–234), pMFa (Kurjan and Herskowitz, (1982) *Cell* 30: 933–943), pJRY88 (Schultz et al., (1987) *Gene* 54:113–123), and pYES2 (Invitrogen Corporation, San Diego, Calif.). The desired polypeptides can be expressed in insect cells (e.g., SF9 cells) using baculovirus expression vectors (see, e.g., O'Reilly et al. (1992) *Baculovirus Expression Vectors: A Laboratory Manual*, Stockton Press).

4) Introduction of Nucleic Acid into a Host Cell.

Nucleic acid(s) encoding the apophytochrome and/or components of the bilin biosynthetic pathway n can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (1989) *Molecular Cloning: A Laboratory*

*Manual, 2nd Edition*, Cold Spring Harbor Laboratory press, and other laboratory textbooks.

The number of host cells transformed with a nucleic acid of the invention will depend, at least in part, upon the type of recombinant expression vector used and the type of transfection technique used. Nucleic acid can be introduced into a host cell transiently, or for long term. In long-term systems, the nucleic acid is stably integrated into the genome of the host cell or remains as a stable episome in the host cell.

Certain vectors integrated into host cells at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

Nucleic acid encoding the polypeptides of the invention can be introduced into cells growing in culture in vitro by conventional transfection techniques (e.g., calcium phosphate precipitation, DEAE-dextran transfection, electroporation, biolistics, etc.). Nucleic acid can also be transferred into cells in vivo, for example by application of a delivery mechanism suitable for introduction of nucleic acid into cells in vivo, such as retroviral vectors (see e.g., Ferry et al. (1991) *Proc. Natl. Acad. Sci., USA*, 88: 8377–8381; and Kay et al. (1992) *Human Gene Therapy* 3: 641–647), adenoviral vectors (see, e.g., Rosenfeld (1992) *Cell* 68: 143–155; and Herz and Gerard (1993) *Proc. Natl. Acad. Sci., USA*, 90:2812–2816), receptor-mediated DNA uptake (see e.g., Wu, and Wu (1988) *J. Biol. Chem.* 263: 14621; Wilson et al. (1992) *J. Biol. Chem.* 267: 963–967; and U.S. Pat. No. 5,166,320), direct injection of DNA (see, e.g., Acsadi et al. (1991) *Nature* 332: 815–818; and Wolff et al. (1990) *Science* 247:1465–1468) or particle bombardment (biolistics) (see e.g., Cheng et al. (1993) *Proc. Natl. Acad. Sci., USA*, 90:4455–4459; and Zelenin et al. (1993) *FEBS Letts*. 315: 29–32).

5) Recovery of Expressed Polypeptide or Holophytochrome.

In some instances, it is desired to recover the expressed polypeptide (e.g. HY2 family reductase) and/or the assembled holophytochrome or the holophytochrome labeled polypeptide. Once expressed, the desired proteins and/or holophytochromes can be purified according to standard procedures of the art, including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification.*, Academic Press, Inc. N.Y.). In certain embodiments, substantially pure compositions of at least about 90 to 95% homogeneity are preferred, and 98 to 99% or more homogeneity are most preferred. The cloning and expression of a HY2 family members is illustrated in Examples 1 and 2, and the expression of a holophytochrome is illustrated in Example 3.

One of skill would recognize that modifications can be made to the apophytochrome and/or the HY2 reductases (or other components of the phytochrome synthetic pathway) without diminishing their biological activity. Some modifications may be made to facilitate the cloning, and expression of the subject molecule(s). Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

IV. Assembly of Phytochromes and Phytofluors.

In certain preferred embodiments, this invention provides for the assembly of holophytochromes. It was a surprising discovery of this invention that a cell transfected with nucleic acids encoding the components of a bilin synthetic pathway (e.g., HO1, PcyA, and/or HY2) and a nucleic acid encoding an apophytochrome (e.g. Cph1)) will express a phytochromobilin that assembles with the apophytochrome to produce a photoactive holophytochrome.

It has been demonstrated that recombinant apophytochromes produced in microorganisms can self assemble with the bilins, phycocyanobilin, phytochromobilin and phycoerythrobilin, to produce photoreversible holophytochromes and intensely fluorescent phytofluors in vitro (Wahleithner et al. (1991) *Proc. Natl. Acad. Sci. USA*, 88: 10387–10391; Li and Lagarias (1992) *J. Biol. Chem.*, 267: 19204–19210; Murphy and Lagarias (1997) *Curr. Biol.* 7: 870–876; U.S. Pat. No. 6,046,041).

This invention additionally provides the genes encoding ferredoxin-dependent bilin reductases that convert biliverdin to phytochromobilin, phycocyanobilin or phycoerythrobilin (see FIG. 1). In one aspect, this invention describes an in vivo expression system for holophytochrome.

One preferred approach involved the design of a synthetic operon comprising HO1 and PcyA coding regions from *Synechocystis* sp. PCC6803 (Yanofsky et al. (1981) *Nucl. Acids Res.*, 9: 6647–6667; Baneyx (1999) *Curr. Opin. Biotechnology*, 10: 411–421; Yeh, et al. (1997) *Science*, 277: 1505–1508). Cloning of ho1 and pcyA genes from *Synechocystis* sp. PCC6803 in the plasmid pPROLarA122 (Clontech Laboratories) places these genes under the control of dual Ara/Lac promotor. Upon introduction of this plasmid into *E. coli* cells harboring the Cph1-expression plasmid, pBAD/Cph1(514), photoactive holophytochrome is expressed/assembled in vivo.

Another particularly preferred approach, illustrated in Example 3, involved the production of a synthetic operon comprised of HO1 from *Synechocystis* sp. PCC6803 and the mature HY2 coding region (mHY2) from *Arabidopis thaliana* that lacks the plastid targeting sequence. The cloning of HO1 and mHY2 open reading frames into the plasmid pPROLarA122 (Clontech Laboratories) placed this operon under regulatory control of a dual Ara/Lac promoter. Upon introduction of this plasmid into *E. coli* cells harboring the Cph1-expression plasmid, pBAD/Cph1(514), in which Cph1(N514) is under regulatory control of a Ara promoter, the production of photoactive holophytochrome in vivo was observed.

These approaches are illustrative and not meant to be limiting. Using the teaching provided herein, numerous other approaches will be available to one of skill in the art. For example, cell lines naturally harboring HO1 can be used thereby eliminating the need to provide this enzyme from a heterologous nucleic acid. Alternatively, the cell can be provided exogenous biliverdin using a variety of transfection reagents (e.g. (e.g. cationic lipids, lipofectamine™, Chariot™, etc.).

Other bilin reductases can be used, numerous apoproteins or minimal domains thereof sufficient to form holophytochromes and/or phytofluors can be used, and other components of the bilin biosynthetic pathway can be provided by heterologous nucleic acids. For example, it is cells expressing an apophytochrome, HO1, pebA and pebB will produce phytofluors in vivo. Similarly, co-expression of the structural gene for a phycobiliprotein, a phycobiliprotein bilin lyase and the genes necessary for a phytobilin biosynthetic pathway from heme will lead to the production of fluorescent phycobiliproteins in living cells.

V. Kits.

This invention also provides kits for the practice of the methods of this invention. In one embodiment the kits include a container containing one or more bilin reductases of this invention (e.g. HY2 family members) and/or nucleic acids encoding one or more bilin reductases of this invention. In certain embodiments, the kits comprise a container containing nucleic acids sufficient express and assemble a holophytochrome (e.g. a bilin chromophore or a phytofluor) in a host cell. Such kits, optionally include a vector encoding an apoprotein and, optionally, a restriction site to insert a nucleic acid into the vector so the heterologous nucleic acid expresses a fusion protein with the apoprotein.

The kits may optionally include devices and reagents to facilitate performing the methods of this invention. Such devices and reagents include, but are not limited to microtiter plates (e.g. for high-throughput applications), culture plates, culture media, cell lines, buffers, labels, and the like.

In addition, the kits optionally include labeling and/or instructional materials providing directions (i.e., protocols) for the practice of the methods of this invention. Preferred instructional materials describe the expression of a bilin reductase and/or the in vivo expression/assembly of a holophytochrome and/or a phytofluor and/or the expression of a polypeptide labeled (as a fusion protein) with a holophytochrome or a phytofluor.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

The *Arabidopsis* HY2 Gene Encodes Phytochromobilin Synthase, a Ferredoxin-Dependent Biliverdin Reductase Light perception by the plant photoreceptor phytochrome requires the tetrapyrrole chromophore phytochromobilin (PΦB), which is covalently attached to a large apoprotein. *Arabidopsis* mutants hy1 and hy2, which are defective in PΦB biosynthesis, display altered responses to light due to a deficiency in photoactive phytochrome. In this example, we describe the isolation of the HY2 gene by map-based cloning. hy2 mutant alleles possess alterations within this locus, some of which affect the expression of the HY2 transcript. HY2 encodes a soluble protein precursor of 38 kD with a putative N-terminal plastid transit peptide. The HY2 transit peptide is sufficient to localize the reporter green fluorescent protein to plastids. Purified mature recombinant HY2 protein exhibits PΦB synthase activity (i.e., ferredoxin-dependent reduction of biliverdin IXα to PΦB), as confirmed by HPLC and by the ability of the bilin reaction products to combine with apophytochrome to yield photoactive holophytochrome. Database searches and hybridization studies suggest that HY2 is a unique gene in the *Arabidopsis genome* that is related to a family of proteins found in oxygenic photosynthetic bacteria.

Introduction.

Plants are exquisitely sensitive to their environment. Because they are sessile and use light as the energy source for photosynthesis, plants have developed well-refined photoreception and signaling systems to modulate their growth and development. The family of phytochromes, which are sensory photoreceptors for red and far red light, play a key role in mediating responses to light quality, quantity, direction, and duration throughout plant development (Kendrick and Kronenberg (1994) *Photomorphogenesis in Plants*. (Dordrecht, The Netherlands: Martinus Nijhoff Publishers); Quail et al. (1995) *Science* 268: 675–680; Furuya, and Schäfer (1996) *Trends Plant Sci*. 1: 301–307; Neff et al. (2000) *Genes Dev*. 14: 257–271). Plant phytochromes are homodimers composed of ~125-kD subunits each with a thioether-linked phytochromobilin (PΦB) prosthetic group (Lagarias and Rapoport (1980) *J. Am. Chem. Soc*. 102: 4821–4828). Phytochrome action depends on its ability to photointerconvert between the red light-absorbing form and the far-red-light absorbing form, a property conferred by covalently bound PΦB in holophytochrome.

Figure 2:
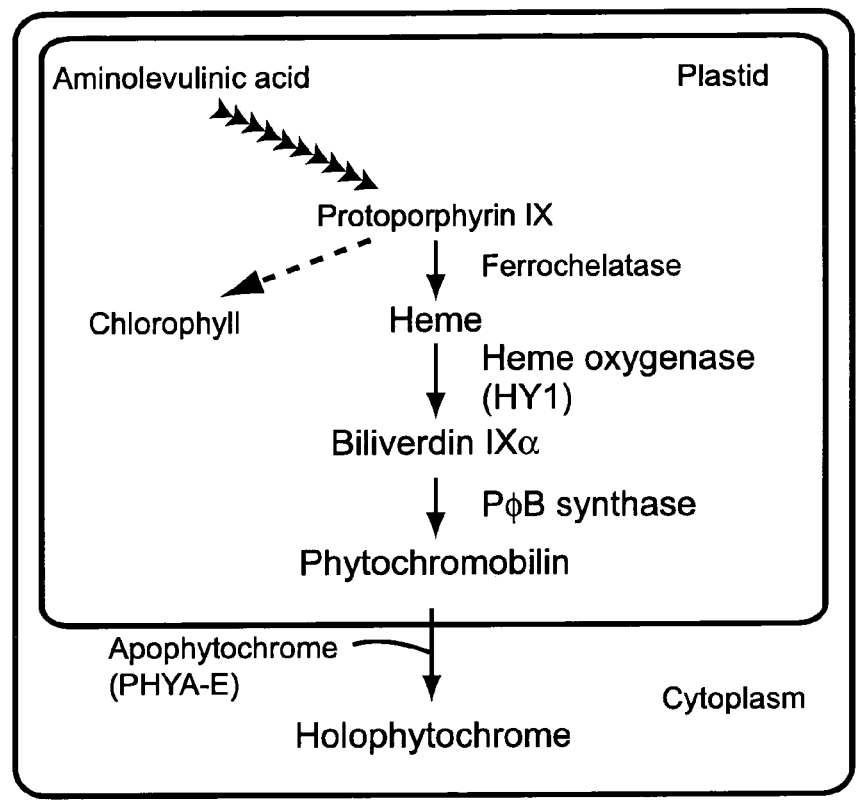
FIG. 2 illustrates phytochrome biosynthesis in *Arabidopsis*.

Two pathways are involved in the biosynthesis of holophytochrome, one for the apoprotein, which is encoded by a small multigene family (e.g., PHYA-E in *Arabidopsis*) (Sharrock and Quail (1989) *Genes Dev*. 3: 1745–1757; Clack et al. (1994) *Plant Mol. Biol*. 25: 413–427), and another for the synthesis of the PΦB (Terry et al. (1993) *Arch. Biochem. Biophys*. 306: 1–15). Apophytochrome is synthesized in the cytosol, whereas PΦB is synthesized entirely within the plastid compartment, followed by its release to the cytosol, where holophytochrome assembly occurs (FIG. 2). Based on spectroscopic studies of purified phytochromes, in vitro bilin assembly studies with recombinant apophytochromes, and physiological analyses of chromophore-deficient mutants, PΦB appears to be the immediate chromophore precursor of all higher plant and cryptophyte phytochromes (Terry et al. (1993) *Arch. Biochem. Biophys*. 306: 1–15; Terry (1997) *Plant Cell Environ*. 20: 740–745).

PΦB is synthesized from 5-aminolevulinic acid and shares many intermediates with the pathways of chlorophyll and heme biosynthesis (Elich and Lagarias (1987) *Plant Physiol*. 84: 304–310; Elich et al. (1989) *J. Biol. Chem*. 264: 183–189). These analyses established that biliverdin IXα (BV) is a PΦB precursor, suggesting the intermediacy of heme in the phytochrome chromophore biosynthetic pathway. Indeed, the first committed step of PΦB biosynthesis is catalyzed by a ferredoxin-dependent heme oxygenase, which is encoded by the HY1 gene in *Arabidopsis* and by its ortholog in rice (Davis et al. (1999) *Proc. Natl. Acad. Sci*., USA, 96: 6541–6546; Muramoto et al. (1999) *Plant Cell* 11: 335–347; Izawa et al. (2000) *Plant J.* 22: 391–399). Ferredoxin-dependent heme oxygenases were first identified in red algae and cyanobacteria, in which they catalyze the oxygen-dependent conversion of heme to BV (Beale and Cornejo (1984) *Arch. Biochem. Biophys.* 235, 371–384; Cornejo and Beale (1988) *J. Biol. Chem.* 263: 11915–11921; Cornejo and Beale (1997) *Photosynth. Res.* 51: 223–230; Cornejo et al. (1998) *Plant J.* 15: 99–107). BV, therefore, is the first committed intermediate in the biosynthetic pathways of PΦB as well as those of the phycobilins phycocyanobilin and phycoerythrobilin, which are precursors of the light-harvesting prosthetic groups of the phycobiliproteins in cyanobacteria, red algae, and cryptomonads (Beale (1993) *Chem. Rev.* 93: 785–802).

In plants, BV is subsequently reduced to 3Z-PΦB by the ferredoxin-dependent bilin reductase PΦB synthase, which has not yet been cloned (T Terry and Lagarias (1991) *J. Biol. Chem.* 266: 22215–22221). Although 3Z-PΦB can serve as a functional precursor of the phytochrome chromophore, its facile isomerization to 3E-PΦB, which is also a precursor of the phytochrome chromophore, likely occurs in plants (Terry et al. (1995) *J. Biol. Chem.* 270: 11111–11118). Ferredoxin-dependent bilin reductases are also present in cyanobacteria and red algae, where they catalyze the conversion of BV to the phycobilins (reviewed by Beale (1993) *Chem. Rev.* 93: 785–802). None of these bilin reductases has previously been cloned.

Our understanding of photomorphogenesis in plants has been aided greatly by the isolation of five classic photomorphogenic *Arabidopsis* mutants (hy1 to hy5) that are impaired in response to light (Koornneef et al. (1980) *Z. Pflanzenphysiol.* 100: 147–160). Photoreceptor-deficient mutants have proven to be powerful tools to analyze which photoreceptors mediate specific photomorphogenetic responses (Koornneef and Kendrick (1994) *Photomorphogenic mutants of higher plants.* Pp. 601–628 *In Photomorphogenesis in Plants*, R. E. Kendrick and G. H. M. Kronenberg, eds Dordrecht, The Netherlands: Kluwer Academic Pub.; Whitelam and Devlin (1997) *Plant Cell Environ.* 20: 752–758). Phytochrome chromophore-deficient mutants, including hy1 and hy2 in *Arabidopsis*, yg-2 and aurea in tomato, pcd1 and pcd2 in pea, and pew1 and pew2 in *Nicotiana plumbaginifolia*, have often been used as phytochrome-deficient mutants (reviewed by Terry (1997) *Plant Cell Environ.* 20: 740–745). The *aurea* mutant of tomato has been used widely for physiological studies of phytochrome, for the study of other photoreceptors, and to study phytochrome signaling (Becker et al. (1992) *Planta* 188: 39–47; Bowler and Chua (1994) *Plant Cell* 6: 1529–1541). Knowledge of the molecular basis of these mutations will help in the interpretation of physiological experiments with these mutants. Biochemical analyses have established that the hy1, pcd1, and yg-2 mutants are deficient at the step at which BV is synthesized from heme, whereas pcd2 and *aurea* mutants are unable to synthesize PΦB from BV (Terry and Kendrick (1996) *J. Biol. Chem.* 271: 21681–21686; van Tuinen et al. (1996) *Plant J.* 9: 173–182; Weller et al. (1996) *Plant Cell* 8: 55–67; Weller et al. (1997) *Plant J.* 11: 1177–1186). The cloning of HY1 has provided valuable insight into the first committed enzyme of phytochrome chromophore biosynthesis, heme oxygenase (Davis et al. (1999) *Proc. Natl. Acad. Sci., USA*, 96: 6541–6546; Muramoto et al. (1999) *Plant Cell* 11: 335–347).

Of the five classic photomorphogenetic mutants, only hy2 remains to be cloned. It is widely believed that HY2 encodes PΦB synthase. However, the observation that a hy2 mutant is partially "rescued" by BV treatment suggests other possibilities (Parks and Quail (1991) *Plant Cell* 3: 1177–1186). Although it is similar to hy1 mutants, the chlorophyll-deficient phenotype of hy2 mutants is typically less severe (Koornneef et al. (1980) *Z. Pflanzenphysiol.* 100: 147–160; Chory et al. (1989) *Plant Cell* 1: 867–880). The gene identification of HY2 in *Arabidopsis* should help to resolve these paradoxes. In this study, we describe the molecular basis for the phytochrome-deficient phenotype in the hy2 mutant of *Arabidopsis*. We show that the HY2 gene encodes PΦB synthase, a ferredoxin-dependent BV reductase that is responsible for the final step in phytochrome chromophore biosynthesis in plastids. This work has enabled us to identify other members of the HY2-related, ferredoxin-dependent bilin reductase family in phycobiliprotein-producing photosynthetic organisms (see Example 3 herein).

Results.

Figure 3A:
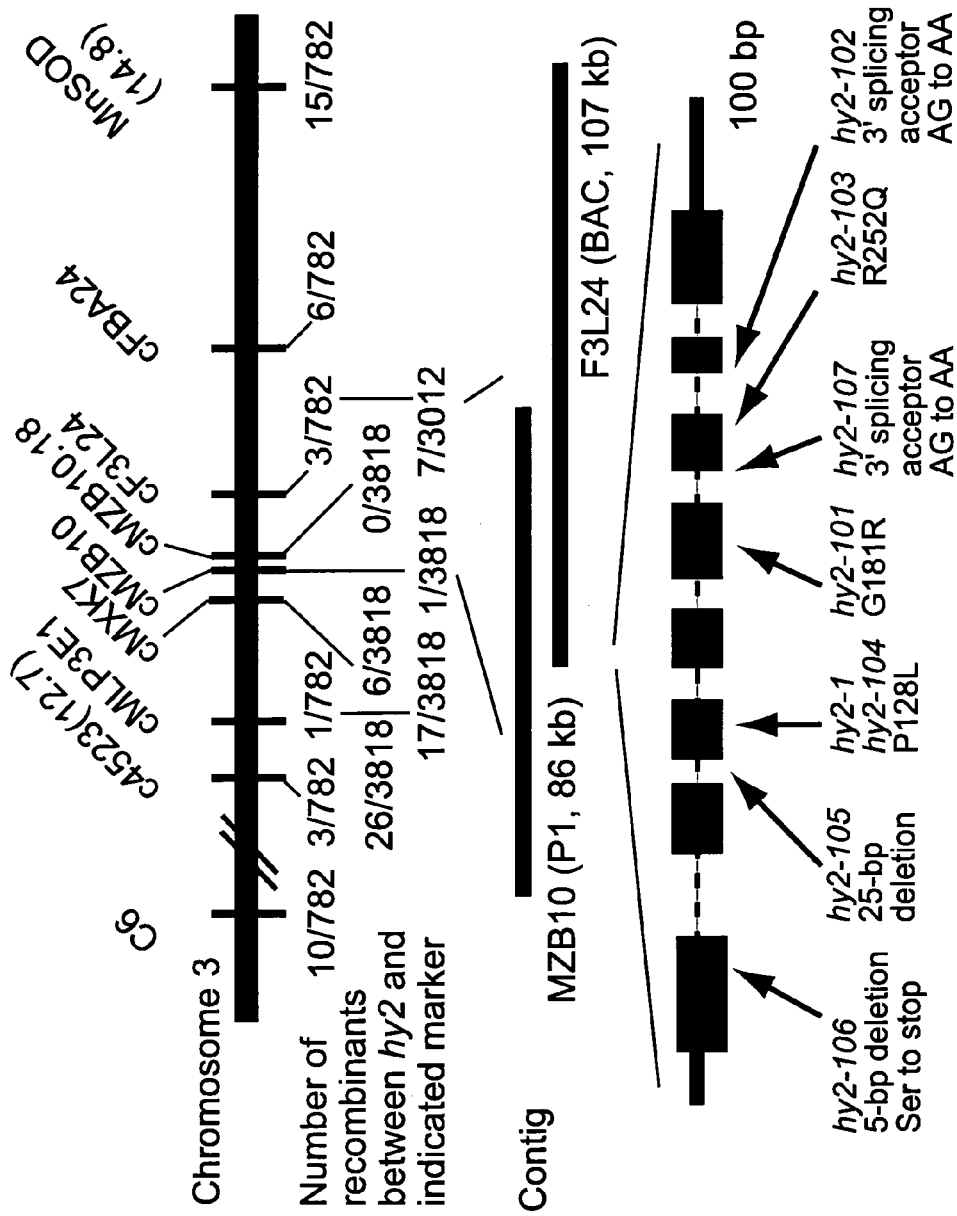

Fine Mapping Localizes the HY2 Gene to Two Overlapping Bacterial Artificial Chromosome Clones We used a positional cloning strategy to isolate the HY2 gene, which previously had been mapped to chromosome 3. Because the hy2 long hypocotyl phenotype is easy to score in seedlings, the HY2 locus has served as a useful landmark for classic mapping. For fine mapping, we crossed the hy2-1 mutant of Landsberg erecta (Ler) ecotype to the wild-type Columbia ecotype, and segregating F2 populations with the hy2 phenotype were used for DNA preparation. First, we prepared DNA from ~400 plants to perform genetic mapping of hy2 using cleaved amplified polymorphic sequence (CAPS) markers (Konieczny and Ausubel (1993) *Plant J.* 4: 403–410) that we developed and that are available in the database at the *Arabidopsis* Information Resource (TAIR; http://www.arabidopsis.org/maps/CAPS_Chr3.html). With ~400 plants, HY2 was mapped to an interval of ~360 kb between positional markers cMLP3E-1 and cF3L24 (FIG. 3A), indicating that recombination frequency in this region was much lower than expected. Therefore, we increased the size of the mapping population to ~2000 plants. This approach enabled us to map the HY2 locus to an interval of ~66 kb between the markers cMZB10 and cF3L24 (FIG. 3A).

During these mapping studies, the sequences of two bacterial artificial chromosome clones, MZB10 and F3L24, spanning the HY2 locus genetically defined above, were deposited in the GenBank database (accession numbers AC009326 and AC011436). There are at least 21 putative genes in the region between the closest recombinations. We screened HY2 candidate genes based on the following expectations. First, HY2 should be categorized as an unknown or putative gene, because neither gene nor protein sequences of any ferredoxin-dependent bilin reductase were known. Second, HY2 should possess a plastid transit peptide, because enzymatic activity for PΦB synthase was detected in plastids (Terry and Lagarias (1991) *J. Biol. Chem.* 266: 22215–222211). Third, weak sequence similarity between HY2 and an unidentified open reading frame(s) (ORFs) in fully sequenced cyanobacterial bacterial genomes might be detectable, because HY2-related bilin reductase activities have been reported in cyanobacteria (Cornejo and Beale (1997) *Photosynth. Res.* 51: 223–230). The predicted amino acid sequences for all 21 genes in the HY2 region were used for TBLASTN (Altschul et al. (1990) *J. Mol. Biol.* 215: 403–410) and CHLOROP (Emanuelsson et al. (1999) *Protein Sci.* 8: 978–984; http://www.cbs.dtu.dk/services/ChloroP/) analyses. By these criteria, one of these genes with two distinct annotations, MZB10.18 (GenBank accession number AC009326-18) or F3L24.1 (GenBank accession number AC0011436-1), appeared to be a strong candidate for HY2.

The HY2 Gene is Identified by DNA Sequences of Wild-Type and Mutant Alleles

Figures 4A, 4B:
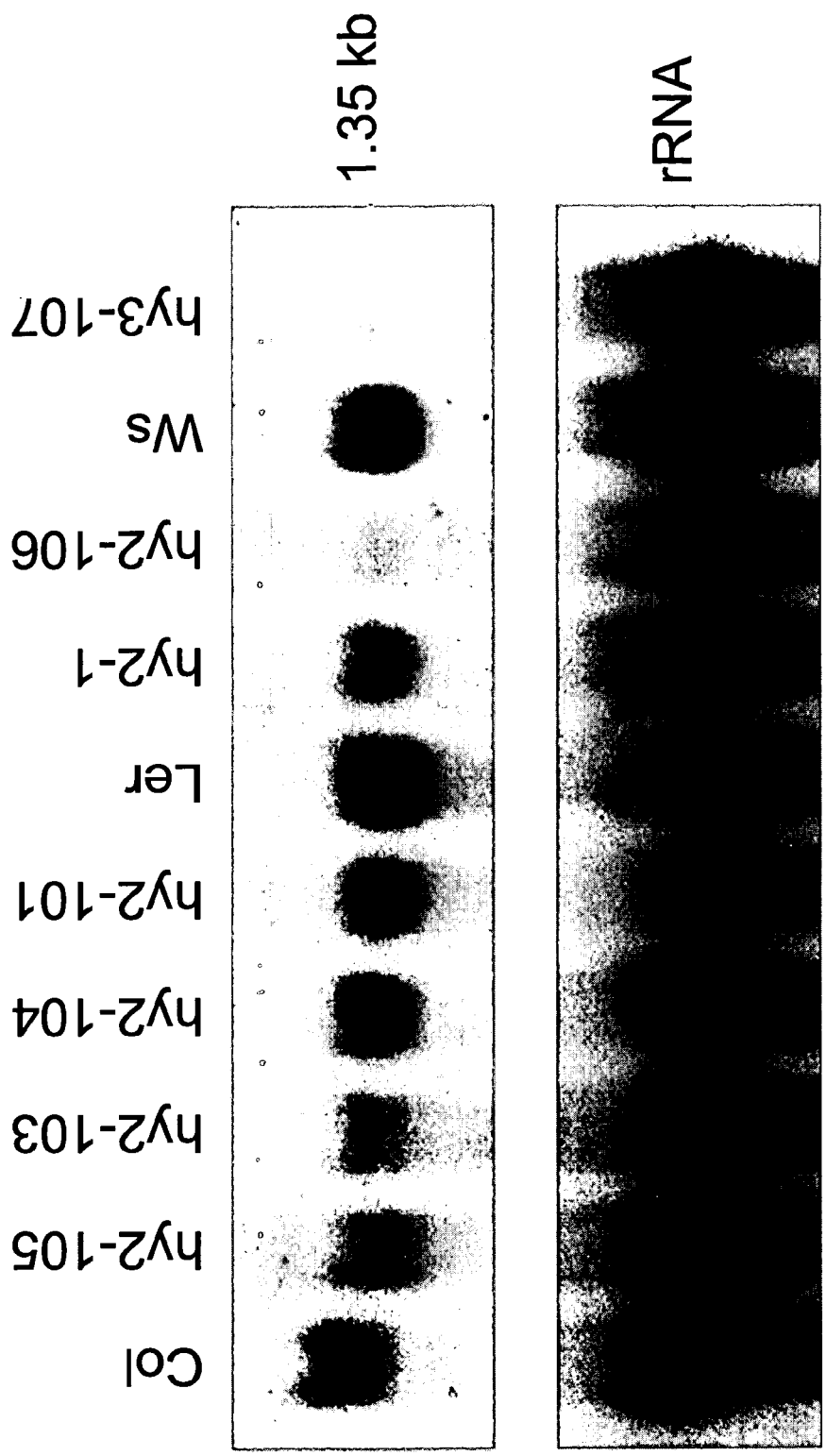
FIGS. 4A and 4B show a RNA gel blot hybridization of MZB10.18/F3L24.1.

To help identify the HY2 gene, RNA gel blot analysis of wild-type and hy2 mutant seedlings was performed using the cDNA for MZB10.18/F3L24.1 as a probe. Because the hy2 phenotype is readily observed in seedlings, we analyzed the accumulation of transcripts in *Arabidopsis* seedlings (FIG. 4). Transcripts were detected in wild-type of three ecotypes tested. The slow migration of mRNA of Col was verified as a gel artifact (data not shown). RNA gel blotting showed that the transcript levels were decreased severely in the hy2-1, hy2-106, and hy2-107 mutants and were decreased slightly in other mutant lines. Consequently, we focused our attention on the MZB10.18/F3L24.1 gene. To determine if mutations were present in the MZB10.18/F3L24.1 gene in hy2 mutants, DNA fragments corresponding to the region from the end of the upstream gene to the beginning of the downstream gene from various hy2 alleles were amplified by polymerase chain reaction (PCR). The nucleotide sequences were determined directly from the PCR products. In all hy2 alleles tested, nucleotide substitutions or deletions were detected (FIGS. 3A and 3B). Based on these data and biochemical data presented below, we conclude that locus MZB10.18/F3L24.1 corresponds to the HY2 gene.

Figure 5:
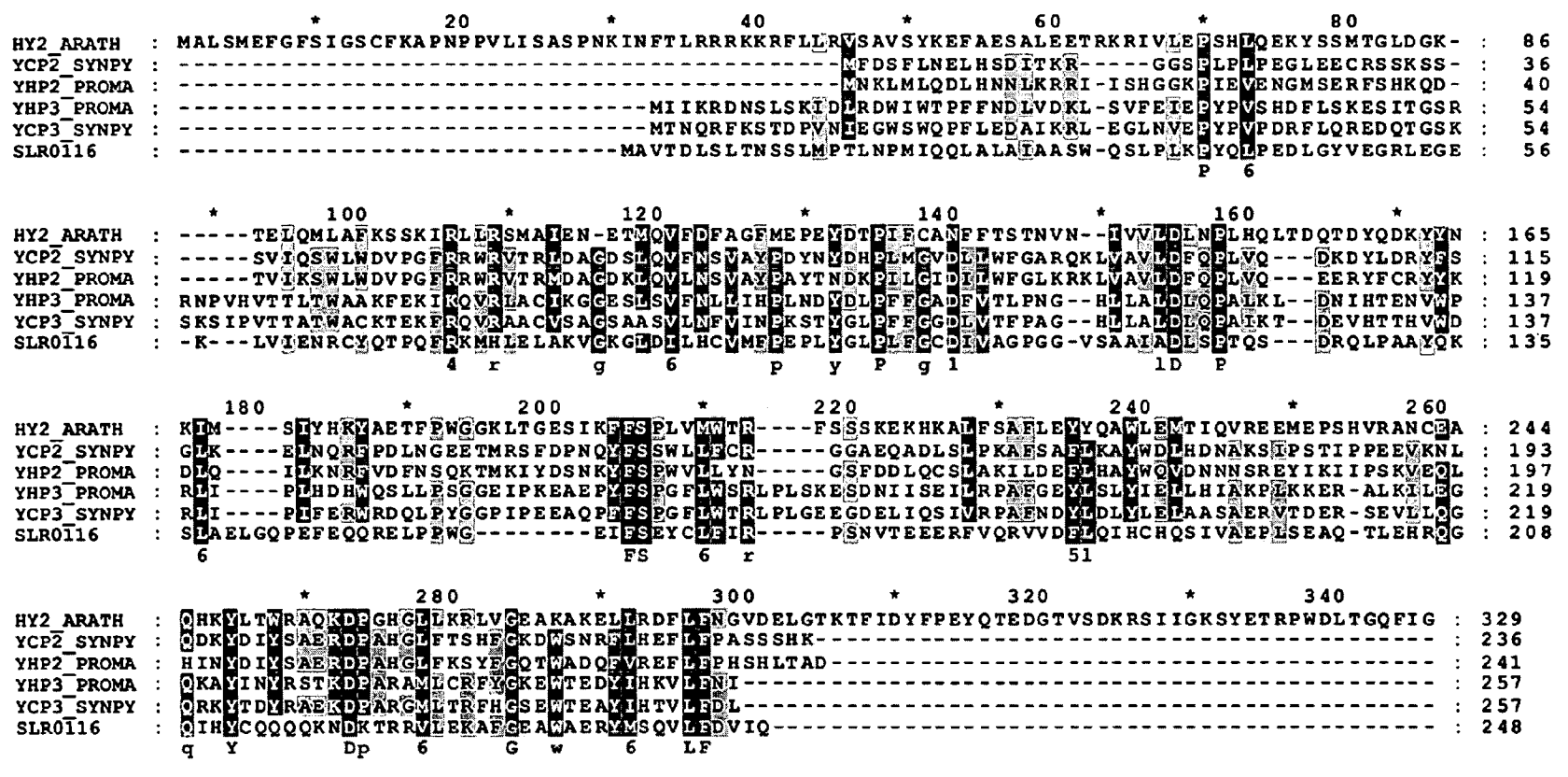

As a result of the conflict in annotation of the HY2 gene in MZB10.18 and F3L24.1 (i.e., the former encodes a protein of 273 amino acids, and the latter encodes a protein of 329 amino acids), we sought to verify experimentally the structure of the HY2 gene. To do so, seven cDNA clones prepared from Columbia seedling mRNA were isolated from ~300,000 clones examined. The nucleotide sequences of independent cDNA clones were determined, and they revealed a single reading frame that matched that of the annotation for F3L24.1. The HY2 gene contains eight small exons ranging from 51 to 222 nucleotides separated by seven introns ranging from 74 to 183 nucleotides. The longest cDNA insert contained a full length 990-bp ORF, a 95-bp 5'-untranslated region, a 231-bp 3'-untranslated region, and a poly(A)$^+$ stretch, as shown in FIG. 5 (DNA Data Bank of Japan [DDBJ] accession number AB045112).

FIG. 3A shows the genomic structure of the HY2 gene with positions of the mutations in hy2 alleles. Two hy2 alleles, hy2-102 and hy2-107, were found to have point mutations at 3' splice sites in the seventh and fifth introns, respectively. Such mutations in the G of the essential AG dinucleotide at the 3' splice site have been reported to lead to missplicing with a downstream AG, resulting in a frameshift in the protein (Brown (1996) *Plant J*. 10: 771–780). hy2-105 was another possible splicing mutant, with a 25-bp deletion in the second intron. This mutation truncates the second intron to 57 nucleotides, much smaller than the average size of *Arabidopsis* introns (240 nucleotides). The efficiency of intron splicing might be reduced because of a minimum intron size requirement (Deutsch and Long (1999) *Nucleic Acids Res*. 27: 3219–3228), although we have not checked the significance of defects in pre-mRNA splicing experimentally. A fast neutron-generated allele, hy2-106, carries a 5-bp deletion in the first exon, making an immediate stop codon. Four ethyl methanesulfonate-generated alleles, hy2-1, hy2-101, hy2-103, and hy2-104, have single nucleotide changes to produce amino acid substitutions compared with the corresponding wild-type allele. Two of these alleles, hy2-1 and hy2-104, have the same mutation (P128L), whereas hy2-101 and hy2-103 possess G181R and R252Q substitutions, respectively.

The HY2 Protein is Related to a Family of Cyanobacterial Proteins.

Based on cDNA sequence analysis, the HY2 protein contains 329 residues with a calculated molecular mass of 38.1 kD. At its N terminus, the HY2 protein sequence is rich in serine, with few acidic residues (six serine and one aspartic acid among 45 residues), which suggests a possible transit peptide for localization to plastids (Gravel and von Heijne (1990) *FEBS Lett*. 261: 455–458). The second amino acid after the initiation methionine is alanine, which is often observed in plastid transit peptides. The program CHLOROP was also used to predict the transit peptide of HY2, and it indicated that the first 45 amino acid residues of the HY2 protein form a chloroplast transit peptide (Emanuelsson et al. (1999) *Protein Sci*. 8: 978–984; http://www.cbs.dtu.dk/services/ChloroP/). The calculated molecular mass of the mature HY2 protein is 33.0 kD and its predicted pI is 5.66, which are similar to those of PΦB synthase purified from oat seedlings. The HY2 protein has no predicted transmembrane helices, which is also consistent with the observation that oat PΦB synthase is a soluble protein.

Using the HY2 protein sequence as a query sequence, we performed an iterative PSI-BLAST search of the nonredundant GenBank/EMBL database (http://www.ncbi.nlm.nih.gov/blast/psiblast.cgi) using default search parameters (Altschul et al. (1997) *Nucleic Acids Res*. 25, 3389–3402). Surprisingly, no HY2-related gene was identified by this search in the nearly complete *Arabidopsis* genome. In contrast, this search identified HY2-related sequences from two marine cyanobacteria, *Prochlorococcus marinus* sp. SS120 (EMBL accession numbers CAB95700.1 and CAB95701.1) and *Synechococcus* sp. WH8020 (SWISS-PROT accession numbers Q02189 and Q02190), and a related protein sequence from the cyanobacterium *Synechocystis* sp. PCC 6803 (cyanobase locus slr0116; Protein Information Resource accession number S76709). Both marine cyanobacteria possess two HY2-related ORFs that appear to be part of multigene operons. Interestingly, the *Synechococcus* ORFs, ycp2_synpy and ycp3_synpy, are located within a cluster of genes involved in phycobiliprotein biosynthesis (Wilbanks and Glazer (1993) *J. Biol. Chem*. 268: 1226–1235), whereas the *Prochlorococcus* ORFs, which we term yhp2_proma and yhp3_proma, are located immediately downstream of a gene related to heme oxygenase (GB: AJ278499.1). These observations strongly support the hypothesis that these genes are involved in phycobilin biosynthesis.

FIG. 5 shows an optimized multiple sequence alignment of HY2 and HY2-related cyanobacterial sequences using the programs CLUSTALW (Higgins et al. (1996) *Meth. Enzymol*. 266: 383–402), MEME to guide hand alignments (http://meme.sdsc.edu/meme/website/), and GENEDOC for highlighting (http://www.psc.edu/biomed/genedoc). As expected, the HY2-related cyanobacterial proteins lack the putative plastid transit peptide sequence found at the N terminus of HY2. Pairwise sequence identities between HY2 and the cyanobacterial ORFs are quite low (<20%), although the similarities between YCP2_SYNPY and YHP2_PROMA and between YCP3_SYNPY and YHP3_PROMA suggest that these pairs of proteins have similar functions. That the mutation in the hy2-1 and hy2-104 alleles (P128L) lies in a conserved proline residue is consistent with a critical role of this residue in the enzyme's structure. Proline residues are typically involved in cis-peptide bonds, which occur at β-turns in proteins. Examination of the amino acid alterations in the two other missense alleles, G181R in hy2-101 and R252Q in hy2-103, reveals that neither mutation corresponds to a strongly conserved residue in this protein family.

The HY2 Protein is Localized to the Plastid.

Figure 6:
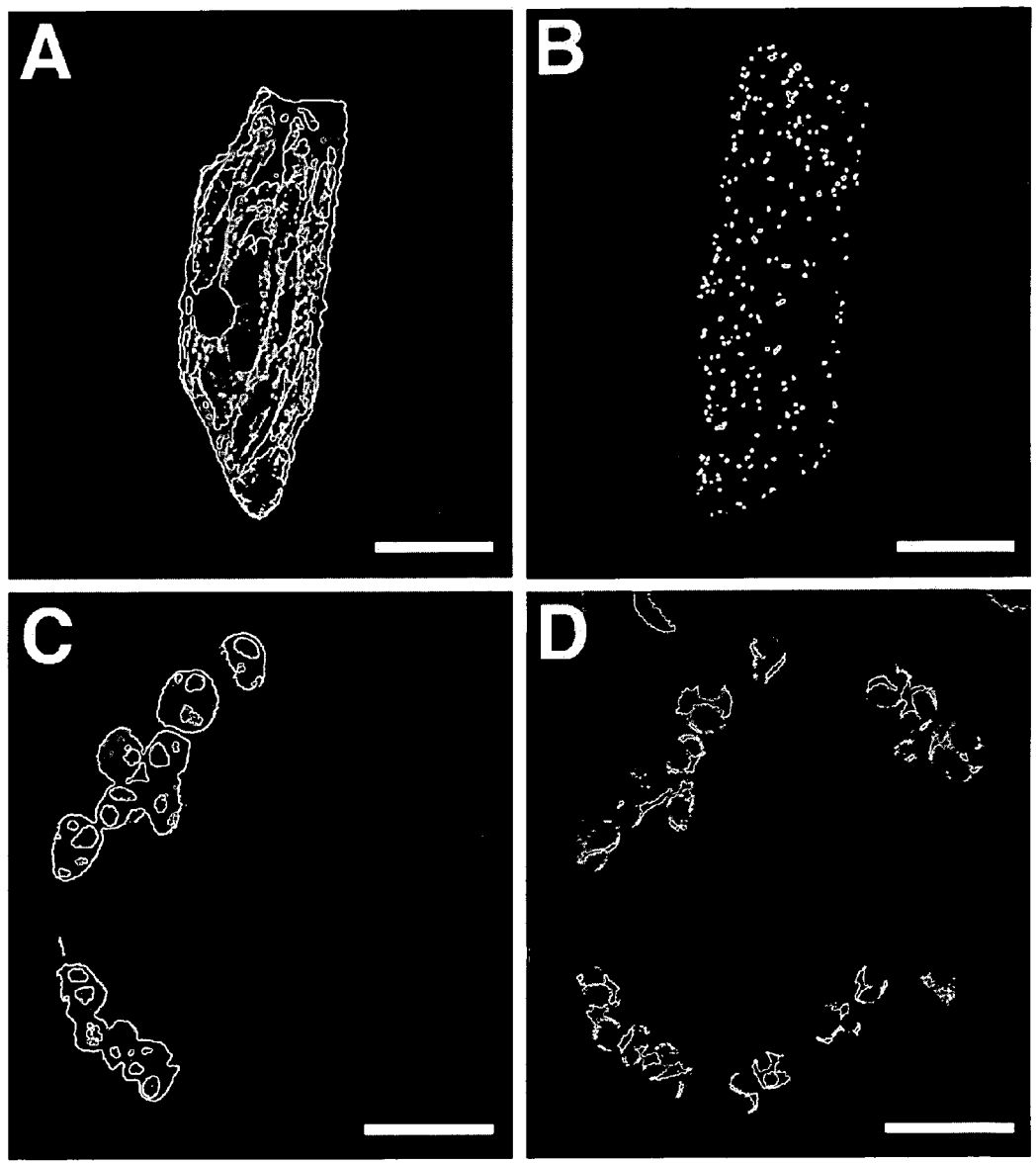
FIGS. 6A through 6D show transient expression of GFP fusion in onion cells and tobacco cells.

The N terminus of HY2 has a stretch of 45 amino acids with features of a chloroplast transit peptide. To determine whether this peptide is a functional plastid-targeting sequence, we fused the transit peptide coding region of HY2 to a modified gene of green fluorescent protein (GFP) from jellyfish under the control of modified cauliflower mosaic virus 35S promoter (Chiu et al. (1996) *Curr. Biol.* 6: 325–330). The construct was introduced into onion skin cells and tobacco leaves by bombardment with DNA-coated particles, and transient expression was analyzed using confocal laser scanning microscopy. Although a control construct without the putative transit peptide showed GFP fluorescence throughout the cytoplasm and the nucleus of onion cells (FIG. 6A), clear localization of GFP fluorescence to small dots, most likely plastids, was observed when the putative transit peptide was fused to GFP (FIG. 6B). For better visualization, we also introduced the construct into tobacco leaves, where the chloroplasts are well developed in guard cells. GFP fluorescence was localized exclusively in oval structures (FIG. 6C) that match the red autofluorescence from the chlorophyll of the chloroplasts (FIG. 6D), demonstrating that the fusion protein is efficiently targeted to chloroplasts. This finding confirms the presence of a functional transit peptide and implies that the HY2 gene product is localized in the chloroplast.

Recombinant HY2 Exhibits PΦB Synthase Activity

Figure 7:
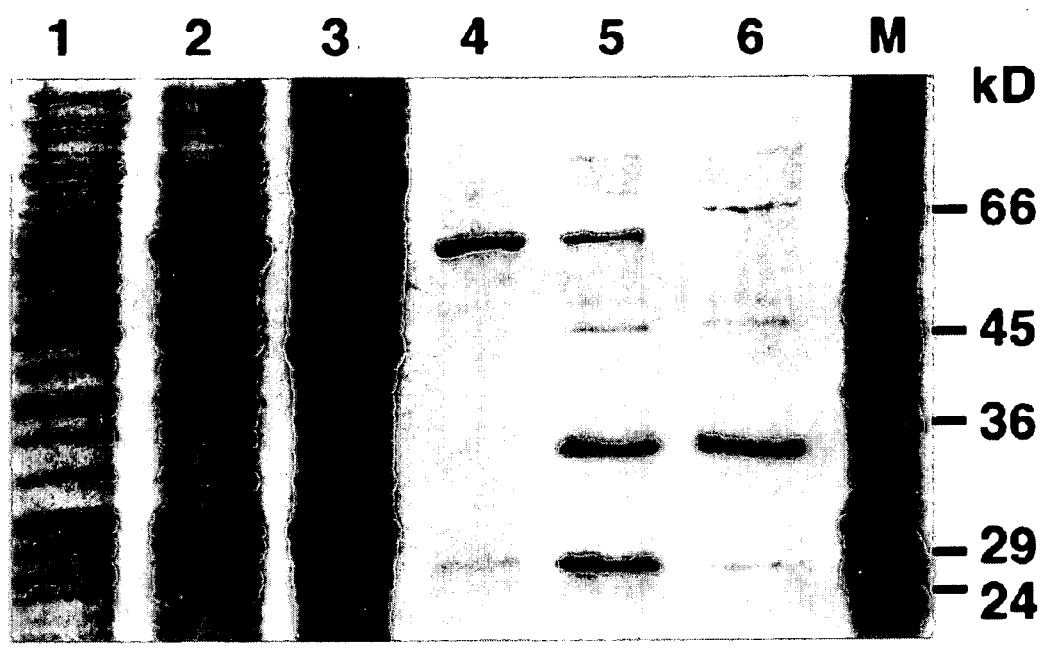
FIG. 7 shows an SDSPAGE of the purification of recombinant *Arabidopsis* mHY2. Lane 1, cell-free extract from uninduced *Escherichia coli* strain DH5a carrying pGEXmHY2; lane 2, cell-free extract from isopropylthioβgalactoside-induced *Escherichia coli* strain DH5a carrying pGEXmHY2; lane 3, soluble fraction of the induction; lane 4, GSTmHY2 after glutathione agarose affinity chromatography; lane 5, GSTmHY2 after PreScission protease treatment; lane 6, purified recombinant mHY2 after a second round of glutathioneagarose affinity chromatography; lane M, molecular mass standards. Numbers at right indicate positions of molecular weight markers (Sigma, SDS7) in kilodaltons.

The HY2 protein lacking the transit peptide, mHY2, was synthesized in *Escherichia* as a fusion protein with glutathione-S-transferase (GST) and purified by affinity chromatography, as described in Methods. The GST tag was removed by site-specific protease digestion. A second round of affinity chromatography yielded protein at >90% homogeneity. FIG. 7 shows SDS-PAGE results of the purification and processing of the protein. One liter of bacterial culture yielded approximately 1 mg of recombinant protein. The molecular mass of the *Arabidopsis* mHY2 deduced from the cDNA is 33 kD. However, the cloning and expression strategy for the mHY2 cDNA using pGEX-6P-1 was responsible for an additional five N-terminal amino acids (GPLGS) after protease treatment.

To determine whether mHY2 has PΦB synthase activity, its ability to reduce BV to PΦB was first assessed with a "coupled" holophytochrome assembly assay in which the reaction products were incubated with recombinant cyanobacterial phytochrome 1 (Cph1) apoprotein (Yeh et al. (1997) *Science* 277: 1505–1508).

Figure 8:
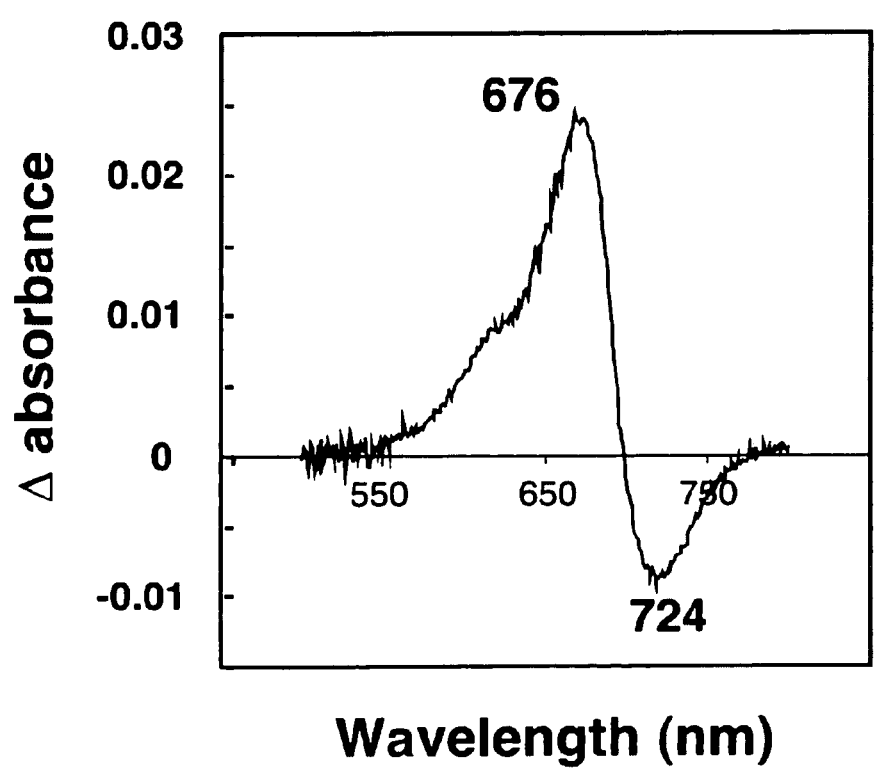
FIG. 8 shows phytochrome difference spectra of cph1 after incubation with BV metabolites. A soluble protein extract of isopropylthio-b-galactoside2-induced *E. coli* DH5a carrying pGEX-mHY2 was assayed for PΦB synthase activity as described herein. Recombinant Cph1 was added to the bilin reaction mixture, which was incubated for another 30 min at room temperature under green safe light, and a phytochrome difference spectrum was obtained. The absorption maximum and minimum are indicated in nanometers.
Figure 9:
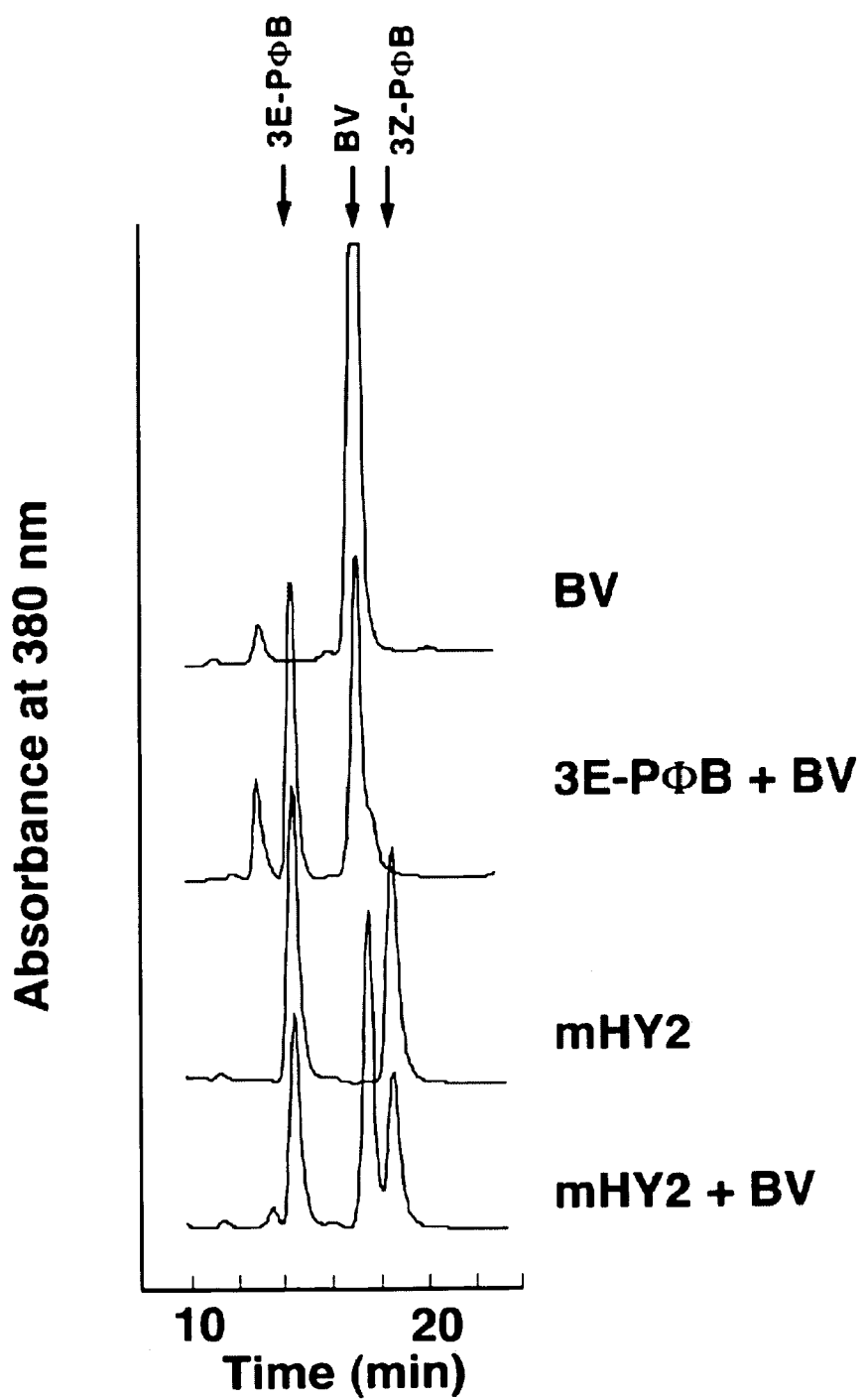
FIG. 9 shows that HY2 converts BV to PΦB as detected by HPLC. Purified recombinant HY2 protein (40 mg) was assayed for PFB synthase activity as described in herein. Bilins were extracted from the incubation mixture using a SepPak C18 reversed phase cartridge and analyzed by reversed phase HPLC as described herein. The HPLC solvent was acetone:20 mM formic acid (50:50 [v/v]), and the eluate was monitored at 380 nm. The top traces represent the standard bilins BV and 3E-PFB. The third trace shows the bilin metabolites obtained after incubation of BV with HY2. The bottom trace has, in addition, BV as an internal standard.

FIG. 8 shows a phytochrome difference spectrum obtained after incubation of apoCph1 with the bilin products from a PΦB synthase assay of a crude cell-free bacterial extract expressing GST-mHY2. The difference spectrum has a peak at 676 nm and a valley at 724 nm, which is consistent with a PΦB-Cph1 adduct (Yeh et al. (1997) *Science* 277: 1505–1508). To ensure that this activity was not due to a component of the crude *Escherichia* lysate, the ability of purified mHY2 to reduce BV to PΦB was analyzed using the coupled assembly assay as well as an HPLC assay. A phytochrome difference spectrum identical to that shown in FIG. 8 was obtained (data not shown). The HPLC results of the PΦB synthase assay mixture are shown in FIG. 9. After incubation of HY2 for 30 min under standard PΦB synthase assay conditions, all of the BV was converted to PΦB. Interestingly, both 3Z- and 3E-PΦB isomers were produced, although the relative amount of the 3E-PΦB isomer varied for different HY2 samples and may be an artifact of the presence of residual glutathione.

Discussion.

The hy2 mutant of *Arabidopsis* is one of five classic long hypocotyl mutants first identified by Koornneef et al. (1980) *Z. Pflanzenphysiol.* 100: 147–160. That the hy2 mutant is photomorphogenetically impaired due to a phytochrome deficiency has been well documented by physiological and photobiological analyses (Koornneef et al. (1980) *Z. Pflanzenphysiol.* 100: 147–160; Chory et al. (1989) *Plant Cell* 1: 867–880; Parks and Quail (1991) *Plant Cell* 3: 1177–1186; Goto et al. (1993) *Photochem. Photobiol.* 57: 867–871). Parks and Quail (1991) *Plant Cell* 3: 1177–1186, showed that the long hypocotyl phenotype of the hy1 and hy2 mutants was in part "rescued" by BV feeding and suggested that these mutants have lesions in the phytochrome chromophore biosynthetic pathway. Indeed, HY1 encodes a plastid-localized heme oxygenase that catalyzes the cleavage of heme to form BV (Davis et al. (1999) *Proc. Natl. Acad. Sci., USA*, 96: 6541–6546; Muramoto et al. (1999) *Plant Cell* 11: 335–347). This example establishes that HY2 encodes PΦB synthase, a plastid-localized enzyme responsible for the ferredoxin-dependent conversion of BV to PΦB, the immediate precursor of the phytochrome chromophore. Although complementation experiments are in progress, sequence analysis of eight mutant alleles has revealed molecular lesions within the HY2 gene. Many of the hy2 alleles also display altered expression of the HY2 transcript, providing compelling evidence that the reduced expression of this gene is responsible for the long hypocotyl phenotype.

Based on the presence of a functional plastid-targeting sequence in the HY2 protein, we can confidently conclude that the entire pathway of PΦB biosynthesis occurs within plastids. Nevertheless, the possibility of an alternative pathway in other subcellular compartments cannot be dismissed entirely. In this regard, there are three other heme oxygenase genes besides HY1 in the *Arabidopsis* genome whose products may play a role in an alternative pathway (M. Masuda, T. Muramoto, and T. Kohchi, unpublished data). However, our database searches revealed no other gene in the *Arabidopsis* genome that shows statistically significant similarity to HY2. Although a weak similarity between HY2 and a ferredoxin-dependent bilin reductase involved in chlorophyll catabolism, red chlorophyll catabolite reductase, was revealed by profile analysis, red chlorophyll catabolite reductase does not catalyze the reduction of BV to PΦB (Wüthrich et al. (2000) *Plant J.* 21: 189–198). Therefore, it appears that HY2 is the only PΦB synthase gene in *Arabidopsis*.

Physiological comparisons of the hy1 and hy2 mutants indicate that hy1 plants display more severe phytochrome-deficient phenotypes (Koornneef et al. (1980) *L Heynh. Z. Pflanzenphysiol.* 100: 147–160; Chory (1989) *Plant Cell* 1: 867–880). These observations are somewhat surprising in view of the apparent uniqueness of the HY2 gene and the existence of multiple HY1-related proteins in the *Arabidopsis genome*. However, this may reflect the strength of the hy1 and hy2 alleles examined. In this regard, the partial rescue of the hy2-1 mutant treated with BV (Parks and Quail (1991) *Plant Cell* 3: 1177–1186) can be explained by the hypothesis that the P131L missense mutation affords a partially active enzyme with a lower affinity for BV. Alternatively, it is possible that BV might be converted to PΦB by an enzyme unrelated to HY2 in *Arabidopsis*. Phytochrome chromophore biosynthetic mutants have been identified in other plant species (Terry (1997) *Plant Cell Environ.* 20: 740–745). In all cases, two classes of mutants have been identified: those that are deficient in heme oxygenase and those that are deficient in PΦB synthase. Based on biochemical analyses, the aurea mutant of tomato and the pcd2 mutant of pea are deficient in PΦB synthase activity (van Tuinen et al. (1996) *Plant J.* 9: 173–182; Weller et al. (1997) *Plant J.* 11: 1177–1186). The observations that the corresponding heme oxygenase mutants in these plant species (i.e., yg-2 and pcd1, respectively) exhibit less severe phenotypes further support the hypothesis that the relative allele strength of the two loci determines the phenotype. A phenotypic comparison of null alleles of hy1 and hy2 (e.g., hy2-106 and hy2-107) should help resolve this question.

The cloning of the *Arabidopsis* HY2 gene will help to identify PΦB synthase genes from other plant species and to confirm that the mutations in aurea and pcd2 occur in homologous genes. The aurea mutant of tomato has been used extensively to analyze phytochrome signal transduction (Bowler et al. (1994) *Cell* 77: 73–81), and knowledge of the molecular basis of this mutation is of considerable interest. The molecular basis of such mutations should provide insight into residues critical for substrate and/or potential cofactor (i.e., metal ions or organic single electron carriers) interactions as well as those necessary for protein-protein interactions (i.e., between HY2 and ferredoxin or between HY1 and HY2). The availability of HY1- and HY2-specific cDNA probes and specific antibodies to both enzymes will facilitate experiments to study the regulation of phytochrome chromophore biosynthesis. With such probes, several key questions can be addressed. Are the two enzymes expressed coordinately in all tissues? Is their expression spatially and temporally regulated? Do HY1 and HY2 proteins form a dual enzyme complex in the plastid that channels the conversion of heme to PΦB? Does the expression of HY1 affect HY2 expression and vice versa?

The molecular cloning of HY2 has provided a breakthrough in our knowledge of bilin biosynthesis in general. Our bioinformatic analyses reveal that HY2 is related to a number of cyanobacterial genes of unknown function (FIG. 5). Indeed, we believe these HY2-related proteins are enzymes involved in the biosynthesis of the chromophore precursors of the light-harvesting phycobiliproteins phycocyanobilin and phycoerythrobilin. As might be expected for enzymes with different substrate/product specificities, these proteins are highly diverged from HY2 (<20% sequence identity). The levels of identity between these proteins and HY2, which are highlighted in FIG. 5, likely reflect residues involved in overall protein folding and/or ferredoxin interaction that are common to the entire family of enzymes. In Example 2, we demonstrate that these HY2-related proteins are members of a growing family of ferredoxin-dependent bilin reductases with different double bond specificities.

The pathway for phytochrome chromophore biosynthesis shown in FIG. 1 has been clearly documented. Now that the two key genes of the phytochrome chromophore biosynthetic pathway have been cloned, we can elucidate how bilin biosynthesis is regulated throughout the plant, a process that is critical to the plant's ability to respond to light. The possible role of bilins as second messengers, which was raised by recent studies of transgenic plants expressing mammalian biliverdin reductase (Montgomery et al. (1999) *Plant Physiol.* 121: 629–639), can be addressed by manipulating the expression of HY1 and HY2 genes within different cells and tissues of the plant. Finally, it will be of particular interest to address the relationship of phytochrome chromophore biosynthesis and chlorophyll biosynthesis, not only because they share common biosynthetic intermediates but to determine how each pathway influences the other.

Methods.

Plant Materials

*Arabidopsis thaliana* ecotypes Columbia (Col), Landsberg erecta (Ler), and Wassilewskija (Ws) were obtained from our laboratory stocks. Mutant strains used in this work were obtained from Maarten Koornneef for hy2-1 (distributed as CS68 by the *Arabidopsis* Biological Stock Center, Columbus, Ohio; in Ler ecotype); from Jason Reed for hy2-101 (EMS89S73S-E isolated originally by J. Reed; in Col ecotype), hy2-102 (EMS195 isolated by J. Reed; in Col ecotype), hy2-103 (IAA$^R$-7 isolated by Allison Wilson; in Col ecotype), hy2-104 (IAA$^R$-12 isolated by A. Wilson; in Col ecotype), hy2-105 (γ10-9 isolated by J. Reed; in Col ecotype), and hy2-106 (FN16-3 isolated by Aron Silverstone; in Ler ecotype); and from Nam-Hai Chua for hy2-107 (segregated hy2 from T-DNA lines in his laboratory; in WS ecotype). Plants were grown under long day conditions at 22° C. in a growth chamber.

Map-Based Cloning

The hy2-1 mutant was outcrossed with wild-type Col ecotype, and the mapping population was selected from F2 families with the long hypocotyl phenotype. Genomic DNA was prepared using a protocol described by Edwards et al. (1991) *Nucleic Acids Res.* 19: 1349. We used cleaved amplified polymorphic sequence (CAPS) markers between Col and Ler (Konieczny and Ausubel (1993) *Plant J.* 4: 403–410), two CAPS markers (C6 and manganese-superoxide dismutase) in the *Arabidopsis* database, and seven new CAPS markers developed during this study. Primer sequences for polymerase chain reaction (PCR) amplification are listed here with the enzymes used for digestion indicated in parentheses:

```
c4523,
5'-ACA GCG AGA TTC AAA GGT CCA TTA    (SEQ ID NO:1)
                                ACC GGA-3' and
5'-GGG CTT ACA GTG ATA TCT GCA AGA    (SEQ ID NO:2)
                   CTT CTA-3' (HpaII);

cMLP3E1,
5'-TAA TGC TTG CGA CAA ACA GG-3' and (SEQ ID NO:3)
5'-GTT CAT CTC AGG GCC AAA AA-3'     (SEQ ID NO:4)
(RsaI);

cMXK7,
5'-GCT TTC AGA AAT CAG ACC TCA A-3'  (SEQ ID NO:5)
and
5'-CTG GTG TGG TTG ATC GAA TCT-3'    (SEQ ID NO:6)
(DdeI);

cMZB10,
5'-CTG CCA AGC TTC ATT TGG TT-3' and (SEQ ID NO:7)
5'-GCA GGA GCT GCA GAC AAT CT-3'     (SEQ ID NO:8)
(BsrI);

cMZB10.18 (=HY2),
5'-CAA TGC AGG TTT AAC TTC AGC A-3'  (SEQ ID NO:9)
and
5'-CCA TGG GAA AGT CTG CAA AT-3'     (SEQ ID NO:10)
(DdeI);

cF3L24,
5'-TCA AGC CCT TTT CCA ACA TC-3' and (SEQ ID NO:11)
5'-TTC CCC ATC TGA ACT CAA CC-3'     (SEQ ID NO:12)
(HinfI); and CF8A24,
5'-AAT GAT GCA TGG TGT TGG TG-3' and (SEQ ID NO:13)
5'-GCT CGA GGA AAA GTC ATC CA-3'     (SEQ ID NO:14)
(MboI).
```

Sequence Analysis of the HY2 Locus

A pair of primers (5'-CGT TTG TCT CAC TGA AAC TG-3' (SEQ ID NO:15) and 5'-CAA TCA TCT TGA AAT GCA GA-3' (SEQ ID NO:16)) was used to amplify 1.98-kb fragments of the MZB10.18 region from mutants and their corresponding wild-type plants. The PCR products were subjected directly to a cycle-sequencing protocol with several primers, and reactions were analyzed on an ABI373S sequencing apparatus (Applied Biosystems, Foster City, Calif.).

Isolation of HY2 cDNA

A cDNA library was constructed by K. Ando (Nara Institute of Science and Technology) from Col seedlings in λZAPII (Stratagene) according to the manufacturer's instructions. The DNA fragment containing MZB10.18 described above was used as a probe to screen ~300,000 cDNA clones by plaque hybridization. Several cDNA plasmids were recovered by in vivo excision according to the manufacturer's instructions.

RNA Isolation and Analysis

RNA was isolated from 1-week-old whole *Arabidopsis* seedlings by the acid guanidinium thiocyanate-phenol-chloroform extraction method using Isogen (Nippon Gene, Tokyo, Japan). Total RNA (10 μg/lane) was electrophoresed on a 1.2% formaldehyde/agarose gel and transferred to a nylon membrane (Hybond-N; Amersham Corp.). Prehybridization and hybridization were then performed in Church hybridization solution (Church and Gilbert (1984)*Proc. Natl. Acad. Sci., USA*, 81: 1991–1995) using radioactive probes ($3 \times 10^6$ to $5 \times 10^6$ cpm/mL). A fragment of cDNA produced by EcoRI and XhoI digestion was used as a hybridization probe. Filters were washed under highly stringent conditions three times with 1×SSC (1×SSC is 0.15 M NaCl and 0.015 M sodium citrate), 0.1% SDS at room temperature and twice with 0.2×SSC, 0.1% SDS at 65° C. for 15 min. To show equal loading of RNA, an rRNA probe was used for hybridization.

Subcellular Localization Experiment with Green Fluorescent Protein Fusion

The coding region of HY2 for the putative transit peptide and flanking amino acid residues (amino acids 1 to 62) isolated by PCR was cloned into pTH2XA, a modified green fluorescent protein (GFP) vector derived from 35SΩ-sGFP-S65T (Chiu et al. (1996) *Curr. Biol.* 6: 325–330). In pTH2XA, five glycine residues were included at the fusion junction to GFP (M. Takemura, unpublished data). The construct, which can express the HY2 transit peptide fused to the N terminus of a modified GFP gene under the control of the cauliflower mosaic virus 35S promoter, was introduced into onion bulbs and tobacco leaves. The conditions of bombardment were the same as those described by Muramoto et al. (1999) *Plant Cell* 11: 335–347. Transient expression was observed after overnight incubation using confocal laser scanning microscopy (LSM510; Carl Zeiss, Jena, Germany).

Construction of the PGEX-mHY2 Expression Vector mHY2, the mature HY2 gene without the predicted chloroplast transit peptide, was subcloned into the *Escherichia coli* expression vector pGEX-6-P1 (Amersham Pharmacia Biotech, Piscataway, N.J.) to produce pGEX-mHY2. mHY2 was amplified using the primers mHY2BglIIfwd. (5'-GA AGATCTG TCT CTG CTG TGT CGT ATA AGG-3', SEQ ID NO:17) and HY2SmaIrev. (5'-TCC CCCGGG TTA GCC GAT AAA TTG TCC TGT TAA ATC-3', SEQ ID NO:18), which contained BglII and SmaI sites (underlined), respectively, and was cloned into BamHI-SmaI-digested pGEX-6-P1 to give pGEX-mHY2. The integrity of the construct was verified by restriction analysis and complete DNA sequencing of the insert (Davis Sequencing, Inc., Davis, Calif.). The constructed vector contains the mHY2 sequence placed 3' to the glutathione-S-transferase (GST) gene of *Schistosoma japonicum* under the control of a Ptac promotor. A recognition sequence for PreScission protease, which is also a GST fusion protein, is located upstream of mHY2. Proteolytic cleavage yields the native *Arabidopsis* mHY2 with the five-amino acid N-terminal extension GPLGS.

Expression and Purification of Recombinant mHY2

The *Escherichia* strain DH5α containing pGEX-mHY2 was grown at 37° C. in 500-mL batches of Luria-Bertani medium containing ampicillin (100 μg/mL) to an $OD_{578}$ of 0.6. Cultures were induced by the addition of 1 mM isopropylthio-β-galactoside and incubated for an additional 3 hr, and bacteria were harvested subsequently by centrifugation. The bacterial pellet from 3 liters of culture was resuspended in 20 mL of lysis buffer (50 mM Tris-HCl, pH 8.0, 100 mM NaCl, 0.05% Triton X-100, 1 mM DTT, 2 mM benzamidine, 2 mM PMSF, leupeptin [2.0 μg/mL], and pepstatin A [3 μg/mL]) and disrupted with a French press (3×20,000 p.s.i.). Cell debris were removed by centrifugation for 30 min at 100,000 g. The resulting supernatant was loaded directly onto a glutathione-agarose (Sigma) column (1 cm×3 cm) that had been equilibrated with 5 column volumes of PBS. Unbound protein was removed by washing the column with 5 column volumes of PBS. GST-mHY2 fusion protein was eluted with 50 mM Tris-HCl, pH 8.0, containing 10 mM reduced glutathione. GST-mHY2-containing fractions were pooled and dialyzed overnight against cleavage buffer (50 mM Tris-HCl, pH 7.0, 100 mM NaCl, 1 mM EDTA, and 1 mM DTT). Digestion of the fusion protein was performed by adding 2 units of PreScission protease (Amersham Pharmacia Biotech) per 100 μg of fusion protein and incubating at 4° C. for 5 h. Removal of uncleaved fusion protein and excised GST tag was achieved by loading the digestion mixture onto a second glutathione-agarose column (1 cm×3 cm). Recombinant mHy2 was detected in the flow through, analyzed by SDS-PAGE, and concentrated using Centriprep-10 concentrator devices (Amicon, Beverly, Mass.). One liter of bacterial culture yielded approximately 1 mg of purified protein.

Determination of Protein Concentration

Protein concentration was determined using the method of Bradford (1976) *Anal. Biochem*. 72: 248–254, or by absorption at 280 nm for purified mHy2, where 1 absorption unit represents 0.64 mg/mL mHy2 (Gill and von Hippel (1989) *Anal. Biochem*. 182: 319–326).

PΦB Synthase Activity Assay

All enzymes used for PΦB synthase assay were obtained from Sigma. For a 1-mL assay of PΦB synthase, the protein fraction to be assayed was diluted into 50 mM Tes-KOH, pH 7.3, containing an NADPH-regenerating system (6.5 mM glucose-6-phosphate, 0.82 mM NADP$^+$, 1.1 units/mL glucose-6-phosphate dehydrogenase type XII from Torula yeast [EC 1.1.1.49]), a ferredoxin-reducing system (4.6 μM spinach ferredoxin, 0.025 units/mL spinach ferredoxin:NADP$^+$ oxidoreductase [EC 1.18.1.2]), and 10 μM BSA (fraction V, heat shock). Glucose-6-phosphate and NADP$^+$ were prepared as 100- and 25-mM stocks, respectively, in water; both were stored at 4° C. The glucose-6-phosphate stock was filter sterilized before storage. Glucose-6-phosphate dehydrogenase was prepared as a 500-unit/mL stock in 5 mM sodium citrate, pH 7.4, and stored at 4° C. Spinach ferredoxin:NADP$^+$ oxidoreductase was prepared as a 10-unit/mL stock with sterile water and stored at 4° C. BSA was made up as a 100-μM stock solution in 0.1 M potassium phosphate buffer, pH 7.4, and stored at either 4 or −20° C. The reaction was initiated by the addition of 5 μM (final concentration) purified biliverdin IXα (McDonagh and Palma (1980) *Biochem. J.* 189: 193–208) in 5 μL of DMSO. Assay mixtures were incubated in a 28° C. water bath under green safe light or under subdued light for the desired amount of time. The assays were stopped by placing them on ice. Product analysis used a direct HPLC assay or a coupled assay after the addition of recombinant cyanobacterial apophytochrome 1 (Cph1) and difference spectroscopy (see below).

Direct HPLC Assay

For the quantitative analysis of PΦB synthase activity, assay mixtures (outlined above) were loaded onto a Waters (Milford, Mass.) $C_{18}$ Sep-Pak Light (catalog No. WAT023501) preconditioned as follows: 3-mL wash with acetonitrile to wet the Sep-Pak, 3-mL wash with MilliQ water, and 3-mL wash with 50 mM 4-methylmorpholine/glacial acetic acid (pH 7.7). After the sample was loaded onto the Sep-Pak, it was washed with 3 mL of 4-methylmorpholine/glacial acetic acid (pH 7.7) followed by 3 mL of 0.1% (v/v) trifluoroacetic acid. The Sep-Pak was then eluted with 2 mL of 100% acetonitrile. The eluate was dried using a Speed-Vac lyophilizer. The dried samples were analyzed by HPLC. Samples were first dissolved in 10 μL of DMSO and then diluted with 200 μL of the HPLC mobile phase (acetone:20 mM formic acid [50:50, v/v]). After the samples were dissolved, they were centrifuged briefly, passed through a 0.45-μm polytetrafluoroethylene syringe filter, and chromatographed using a Varian (Palo Alto, Calif.) 5000 liquid chromatograph. The column eluate was monitored at 380 nm using a Varian UV100 flow-through absorbance detector. Peak areas were quantitated using a 3365 Chemstation II (Hewlett-Packard, Waldbronn, Germany). The HPLC column used for all of the analyses was a Phenomenex (Torrance, Calif.) Ultracarb 5-μm ODS (20) 4.6-mm× 250-mm analytical column with a 4.6-mm×30-mm guard column of the same material. The mobile phase used with this column was acetone:20 mM formic acid (50:50, v/v). The flow rate was 0.8 mL/min.

Coupled Difference Spectral Assay

An alternative to the direct analysis of PΦB synthase activity was the coupled, or indirect, assay. This assay was based on the method outlined previously (Terry and Lagarias (1991) *J. Biol. Chem.* 266: 22215–22221). The assay described above for PΦB synthase was performed as before, but instead of working up the sample by Sep-Pak, an aliquot of recombinant apophytochrome (Cph1 from *Synechocystis* sp. PCC 6803) was added to the sample. The sample was incubated for an additional 20 to 30 min at room temperature under green safe light, and then a difference spectrum was taken. The method for difference spectroscopy was described previously (Terry and Lagarias (1991) *J. Biol. Chem.* 266: 22215–22221).

Example 2

Functional Genomic Analysis of the HY2 Family of Ferredoxin-Dependent Bilin Reductases from Oxygenic Photosynthetic Organisms Phytobilins are linear tetrapyrrole precursors of the light-harvesting prosthetic groups of the phytochrome photoreceptors of plants and the phycobiliprotein photosynthetic antennae of cyanobacteria, red algae, and cryptomonads. Previous biochemical studies have established that phytobilins are synthesized from heme via the intermediacy of biliverdin IXα (BV), which is reduced subsequently by ferredoxin-dependent bilin reductases with different double-bond specificities. By exploiting the sequence of phytochromobilin synthase (HY2) of *Arabidopsis*, an enzyme that catalyzes the ferredoxin-dependent conversion of BV to the phytochrome chromophore precursor phytochromobilin, genes encoding putative bilin reductases were identified in the genomes of various cyanobacteria, oxyphotobacteria, and plants. Phylogenetic analyses resolved four classes of HY2-related genes, one of which encodes red chlorophyll catabolite reductases, which are bilin reductases involved in chlorophyll catabolism in plants. To test the catalytic activities of these putative enzymes, representative HY2-related genes from each class were amplified by the polymerase chain reaction and expressed in *Escherichia coli*. Using a coupled apophytochrome assembly assay and HPLC analysis, we examined the ability of the recombinant proteins to catalyze the ferredoxin-dependent reduction of BV to phytobilins. These investigations defined three new classes of bilin reductases with distinct substrate/product specificities that are involved in the biosynthesis of the phycobiliprotein chromophore precursors phycoerythrobilin and phycocyanobilin. Implications of these results are discussed with regard to the pathways of phytobilin biosynthesis and their evolution.

Introduction.

Phytobilins are linear tetrapyrrole molecules synthesized by plants, algae, and cyanobacteria that function as the direct precursors of the chromophores of the light-harvesting phycobiliproteins and of the photoreceptor phytochrome (Beale (1993) *Chem. Rev.* 93: 785–802; Hughes and Lamparter (1999) *Plant Physiol.* 121: 1059–1068). The pathways of phytobilin biosynthesis have been elucidated by biochemical fractionation of plant and algal extracts, by overcoming a blocked step with exogenous putative intermediates, and by analysis of linear tetrapyrrole-deficient mutants (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345 Terry et al. (1993) *Arch. Biochem. Biophys.* 306: 1–15). These studies indicate that the biosynthesis of phytobilins shares common intermediates with heme and chlorophyll biosynthetic pathways to the level of protoporphyrin IX, at which point the latter two pathways diverge by metalation with iron or magnesium (Beale (1993) *Chem. Rev.* 93: 785–802).

Phytobilins are derived from heme, which is converted to biliverdin IX (BV), the first committed intermediate in their biosynthesis. In red algae, cyanobacteria, and plants, this interconversion is accomplished by ferredoxin-dependent heme oxygenases that are related in sequence to the mammalian heme oxygenase (Cornejo et al. (1998) *Plant J.* 15: 99–107; Davis et al. (1999) *Proc. Natl. Acad. Sci., USA*, 96: 6541–6546; Muramoto et al. (1999) *Plant Cell* 11: 335–347). Although they catalyze the same reaction, mammalian heme oxygenases use an NADPH-dependent cytochrome P450 reductase to generate reducing power for heme catabolism (Maines (1988) *FASEB J.* 2: 2557–2568).

The metabolic fate of BV differs in mammals, cyanobacteria, and plants, with BV being metabolized by different reductases with unique double-bond specificities (FIG. 1). Mammalian biliverdin IX reductase (BVR), an NAD(P)H-dependent enzyme that catalyzes the two-electron reduction of BV at the C10 methine bridge to produce bilirubin IX (BR), was the first of these enzymes to be discovered (Maines and Trakshel (1993) *Arch. Biochem. Biophys.* 300: 320–326). A similar enzyme, encoded by the gene bvdR, was identified recently in cyanobacteria (Schluchter and Glazer (1997) *J. Biol. Chem.* 272: 13562–13569). Cyanobacteria and red algae also possess novel ferredoxin-dependent bilin reductases for the synthesis of the linear tetrapyrrole precursors of their phycobiliprotein light-harvesting antennae complexes (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345; Cornejo et al. (1998) *Plant J.* 15: 99–107).

Primarily on the basis of studies with the red alga *Cyanidium caldarium*, these investigators proposed that the biosynthesis of the two major phycobiliprotein chromophore precursors, phycoerythrobilin (PEB) and phycocyanobilin (PCB), requires two ferredoxin-dependent bilin reductases and several double-bond isomerases. The first bilin reductase catalyzes the two-electron reduction of BV at the C15 methine bridge to produce the BR isomer 15,16-dihydrobiliverdin (DHBV), whereas the second bilin reductase catalyzes the conversion of 15,16-DHBV to 3Z-PEB, a formal two-electron reduction of the C2 and C31 diene system. In *C. caldarium*, an additional enzyme mediates the isomerization of 3Z-PEB to 3Z-PCB, both of which appear to be isomerized to their corresponding 3E isomers before assembly with the nascent phycobiliprotein apoproteins (Beale and Cornejo (1991) *J. Biol. Chem.* 266: 22328–22332; Beale and Cornejo (1991) *J. Biol. Chem.* 266: 22333–22340; Beale and Cornejo (1991) *J. Biol. Chem.* 266: 22341–22345).

More recent studies lend support for a similar pathway of PCB and PEB synthesis in cyanobacteria (Cornejo and Beale (1997) *Photosynth. Res.* 51: 223–230). In contrast with mammals and phycobiliprotein-containing organisms, plants and green algae reduce BV to 3Z-PΦB by the ferredoxin-dependent enzyme PΦB synthase, which targets the 2,3,31,32-diene system for reduction (Terry et al. (1995) *J. Biol. Chem.* 270: 111111–11118; Wu et al. (1997) *J. Biol. Chem.* 272: 25700–25705). In plants, 3Z-PΦB is isomerized to its 3E isomer, which appears to be the immediate precursor of the phytochrome chromophore (Terry et al. (1995) *J. Biol. Chem.* 270: 11111–11118). The green alga *Mesotaenium caldariorum* possesses a second bilin reductase activity that catalyzes the reduction of the 18-vinyl group of PΦB to produce 3Z-PCB (Wu et al. 1997 R15R15). These investigations also revealed that 3E-PCB is the natural phytochrome chromophore precursor in this organism.

Despite the extensive biochemical analysis of the phytobilin biosynthetic pathways in plants, algae, and cyanobacteria, the low levels of bilin reductase expression have hindered efforts to clone these enzymes. Using a genetic approach the HY2 locus of *Arabidopsis*, which encodes the enzyme PΦB synthase was cloned (Example 1).

The studies reported here were undertaken to identify HY2-related genes in the protein and nucleic acid databases. Using cloning, expression, and biochemical characterization, our investigations revealed three new classes of ferredoxin-dependent bilin reductases with either unique substrate or product specificities.

Results.

The HY2-related Gene Family in Cyanobacteria, Oxyphotobacteria, and Plants

Example 1 describes the cloning of the HY2 gene of *Arabidopsis*. Using the deduced protein sequence of HY2, TBLASTN, BLASTP, and PSI-BLAST searches (Altschul et al. (1990) *J. Mol. Biol.* 215: 403410; Altschul et al. (1997) *Nucleic Acids Res.* 25: 3389–3402) were performed to identify putative bilin reductases in the nonredundant National Center for Biotechnology Information database, in CyanoBase (Nakamura et al. 2000 R20R20), and in the Joint Genome Institute Microbial Genome database (http://spider.jgi-psf.org/JGI_microbial/html). These searches identified 15 putative proteins from various photosynthetic bacteria and two known proteins from plants.

FIG. 10 shows a multiple sequence alignment of this family of proteins using CLUSTAL W (Higgins et al. (1996) *Meth. Enzymol.* 266: 383–402), hand adjustment with MEME (Bailey and Elkan (1995) pp. 21–29 In: *Proc. Third Internat. Conf. on Intelligent Systems for Molecular Biology*, Menlo Park, Calif.: American Association of Artificial Intelligence Press), and highlighting with GENEDOC (http://www.psc.edutbiomed/genedoc). This alignment revealed regions of strong similarity interspersed with highly diverged regions, with an average pairwise similarity score of 25%. No sequence similarity of these proteins was observed with mammalian biliverdin reductases.

On the basis of the biochemical data presented here, we name these HY2-related cyanobacterial loci after their roles in the biosynthesis of PCB (i.e., pcyA) and PEB (i.e., pebA and pebB). One of these proteins, the product of locus slr0116 (i.e., pcyA) in the genome of the cyanobacterium *Synechocystis* sp PCC6803, appears to be part of an operon with a putative response regulator located 62 bp upstream (Ashby and Mullineaux (1999) *FEMS Microbiol. Lett.* 181: 253–260). Interestingly, this response regulator belongs to the OmpR subfamily for which a mutation (ycf27) was shown to cause a reduced energy transfer from the phycobilisomes to photosystem I (Ashby and Mullineaux (1999) *FEMS Microbiol. Lett.* 181: 253–260). pcyA-related open reading frames (orfs) also were found in the oxyphotobacterium *Prochlorococcus* sp. MED4 (CCMP1378), which is also known as *Prochlorococcus marinus* MED4, in the marine cyanobacterium *Synechococcus* sp WH8102, and in the nitrogen-fixing, heterocyst-forming filamentous cyanobacteria *Anabaena* sp PCC7120 and *Nostoc punctiforme*. Among the other identified HY2-related genes are two orfs, orf236 and orf257, from the marine cyanobacterium *Synechococcus* sp WH8020 that lie adjacent to each other within the major phycobiliprotein gene cluster (Wilbanks and Glazer (1993) *J. Biol. Chem.* 268: 1226–1235; Wilbanks and Glazer (1993b) *J. Biol. Chem.* 268: 1236–1241). These orfs, which encode the proteins Ycp2_SYNPY and Ycp3_SYNPY, appear to be part of a three-gene operon containing an upstream orf of unknown function, orf200. A similar operon was identified in *Synechococcus* sp WH8102. The genomes of *N. punctiforme* and *Prochlorococcus*, both the MED4 and SS120 (CCMP1375) subspecies, also contain similar operons. In contrast to the *N. Punctiforme* and *Anabaena* operons, an upstream orf in the *Prochlorococcus* operons exhibits a striking similarity to the ferredoxin-dependent heme oxygenase gene HY1 (Davis et al. (1999) *Proc. Natl. Acad. Sci., USA*, 96: 6541–6546; Muramoto et al. (1999) *Plant Cell* 11: 335–347) and its homologs in the cyanobacterium *Synechocystis* sp PCC6803 (Cornejo et al. (1998) *Plant J.* 15: 99–107). On the basis of their roles in PEB biosynthesis shown in this study, we name these ORFs pebA and pebB.

PSI-BLAST iterations also identified a weak relatedness of HY2 to the red chlorophyll catabolite reductase (RCCR) from barley and *Arabidopsis*. RCCR is involved in chlorophyll catabolism and catalyzes the ferredoxin-dependent reduction of the linear tetrapyrrole, red chlorophyll catabolite (RCC), to yield the primary fluorescent chlorophyll catabolite (Wuthrich et al. (2000) *Plant J.* 21: 189–198). These investigators showed that RCCR was incapable of reducing BV to either bilirubin or PB (Wüthrich et al. (2000) *Plant J.* 21: 189–198). Interestingly, the sequence similarity between RCCR and the other HY2-related proteins is so weak that TBLASTN searches using the two RCCR sequences failed to identify HY2 or other HY2-related proteins present in the publicly available databases (Wüthrich et al. (2000) *Plant J.* 21: 189–198). This divergence undoubtedly reflects the unusual substrate specificity of the RCCR for bilins derived from chlorophyll catabolism.

Phylogenetic analysis of the HY2-related family of proteins was performed using a heuristic parsimony search with a modified PAM250 weighting matrix and the program PAUP* version 4.0 (see Methods). A single tree obtained with this analysis (FIG. 11) revealed four clades of HY2-related proteins with strong bootstrap support: PcyA, PebA, PebB, and RCCR. We noted that HY2 lies within in the PebB clade.

Recombinant HY2-Related Proteins are Bilin Reductases

Figure 12:
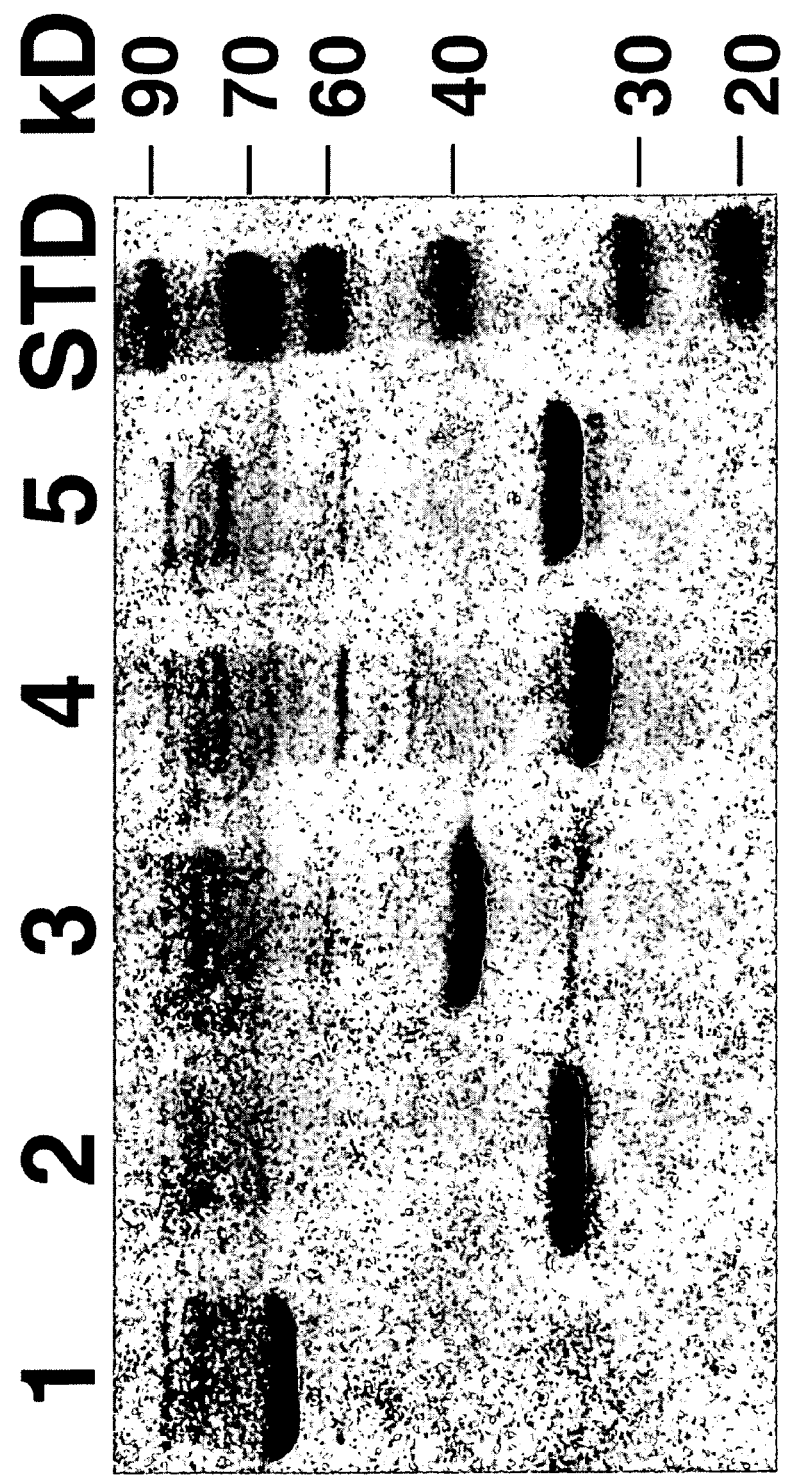
FIG. 12 shows an SDS-PAGE of affinity-purified bilin reductases. Lane 1, GST-PcyA_SYNY3 after glutathione agarose affinity chro-matography; lane 2, purified recombinant PcyA_ANASP after a second round of glutathione agarose affinity chromatography; lane 3, mHY2; lane 4, PebA_SYNPY; lane 5, PebB_SYNPY. STD, molecular mass standards (in kilodaltons).

The HY2-related cyanobacterial orfs were amplified by polymerase chain reaction and cloned into the *Escherichia coli* expression vector pGEX-6P-1, which is similar to the vector described for mHY2 (Example 1). With this vector, the proteins were expressed as glutathione S-transferase (GST) fusions, which enabled their purification by affinity chromatography. The GST tag was removed via site-specific protease digestion, which resulted in an additional five to eight N-terminal amino acids due to the cloning strategy. FIG. 12 shows SDS-PAGE results of purified recombinant protein representatives of the PcyA, PebA, PebB, and HY2 subfamilies. One liter of bacterial culture yielded between 1 and 10 mg of soluble recombinant protein depending on which protein was expressed. The deduced molecular masses of the recombinant processed proteins, confirmed by SDS-PAGE (FIG. 12), are as follows: *Anabaena* PcyA, 28.7 kD); *Synechocystis* PcyA, 28.9 kD; *Synechococcus* sp WH8020 PebA, 28 kD; *Synechococcus* sp WH8020 PebB, 30.3 kD; and *Arabidopsis* mHY2, 33.4 kD.

Figure 13A:
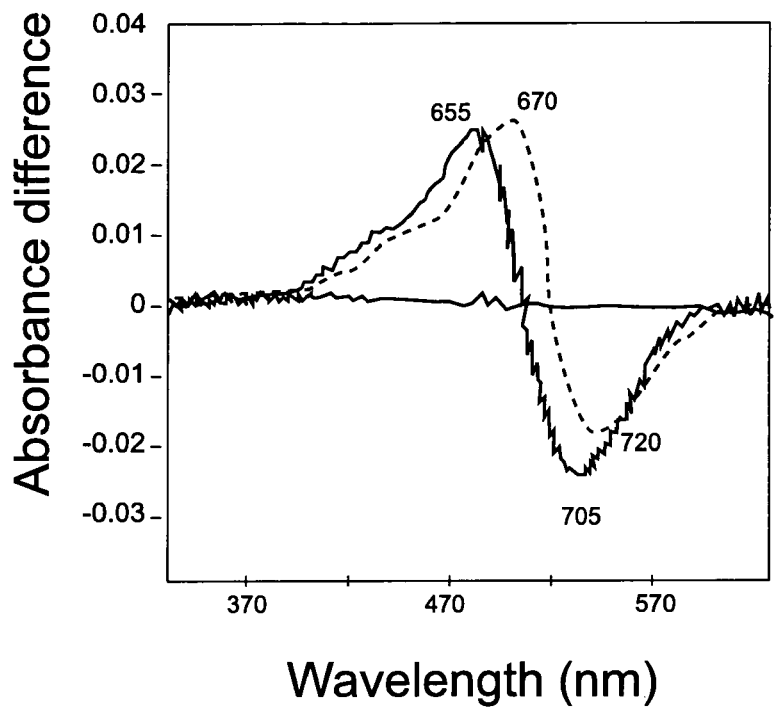
FIGS. 13A and 13B show phytochrome difference spectra and phytofluor fluorescence spectra of recombinant cyanobacterial phytochrome (Cph1) incubated with reaction metabolites.

To determine whether the recombinant HY2-related proteins possess bilin reductase activity, we used a coupled holophytochrome assembly assay to analyze crude protein extracts from *E. coli* expressing these proteins for their ability to convert BV to phytobilins under standard PB synthase assay conditions. FIG. 13A shows that crude bacterial lysates containing GST fusions of mHY2 and PcyA_SYNY3 (PcyA_ANASP; not shown) all exhibited BV reductase activities, yielding phytobilin products that could combine with the cyanobacterial phytochrome Cph1 apoprotein (apoCph1) to yield phytochrome difference spectra. The bilin metabolites incubated with apoCph1 resulted in different maxima and minima, suggesting that the various proteins reduced BV to distinct products. Both PcyA-containing extracts produced a BV metabolite(s) that gave spectra identical to those of the PCB adduct of apoCph1, with difference maxima at 655 nm and minima at 705 nm (Yeh et al. (1997) *Science* 277: 1505–1508). FIG. 13A shows that both difference peaks of the m-HY2 metabolites were markedly red shifted, with maxima at 670 and 730 nm, which is characteristic of the PΦB adduct of apoCph1 (Yeh et al. (1997) *Science* 277: 1505–1508; Example 1). Identical results were obtained using the purified recombinant HY2 and PcyA proteins (data not shown). Similarly, *E. coli* extracts lacking HY2 or PcyA proteins failed to metabolize BV to bilin products that could functionally assemble with apoCph1 (data not shown).

In contrast to the results for PcyA and HY2, no phytochrome difference spectrum was observed when the BV metabolites from reactions containing PebA_SYNPY, PebB_SYNPY, or a 1:1 mixture of the two *Synechococcus*-derived proteins were incubated with apoCph1. To determine whether fusion to GST is responsible for inhibiting the enzyme activity of these proteins, GST was removed by protease digestion and the full-length proteins were purified (FIG. 12). Neither the purified proteins nor the 1:1 mixture of PebA and PebB were able to convert BV to a bilin product(s) that yielded a photoactive adduct with apoCph1 (FIG. 13A). The observation that coincubation of a 1:1 ratio of PebA and PebB with BV elicited a color change of the assay mixture from bluish-green to pink suggested that these proteins converted BV to bilins unable to form a photoconvertible holophytochrome. It is noteworthy that this pronounced color change was not observed when either PebA or PebB was assayed separately. This strongly implied that the PebA/PebB mixture could convert BV to PEB, the precursor of the phycobiliprotein C-phycoerythrin.

Figure 13B:
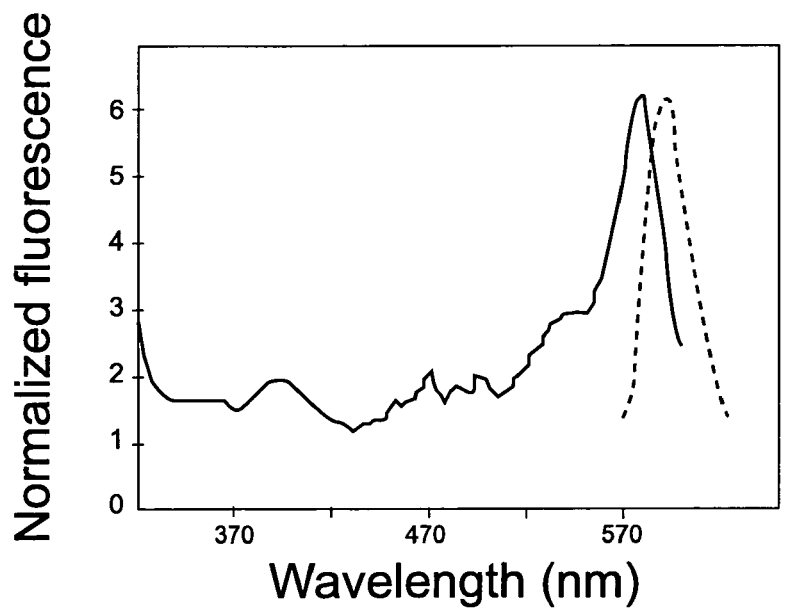

To test this hypothesis, BV-derived bilin metabolites from PebA, PebB, and PebA/PebB were incubated with apoCph1, and the mixtures were analyzed spectrofluorometrically for the production of the fluorescent PEB-apoCph1 "phytofluor" adducts (Murphy and Lagarias (1997) *Curr. Biol.* 7: 870–876). Only the PebA/PebB product mixture yielded a highly fluorescent compound, whose excitation and emission spectra were consistent with the formation of a phytofluor (FIG. 13B). This result suggested that PebA and PebB were both required for the conversion of BV to PEB.

Figure 14:
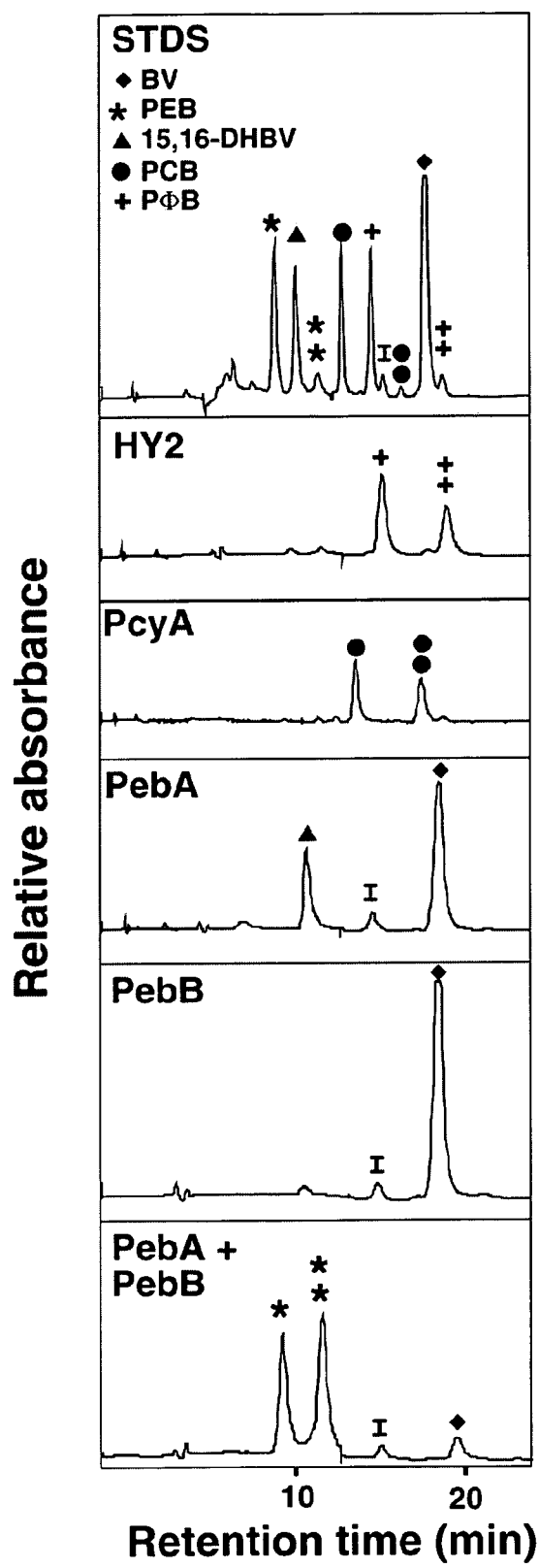
FIG. 14 shows HPLC analysis of the BV metabolites of PebA, PebB, PcyA, and HY2 bilin reductases. Forty micrograms of purified protein was incubated at 28° C. under green safelight in a total assay volume of 5 mL. The assay system contained an NADPH-regenerating system, spinach ferredoxin-NADP$^+$-reductase, spinach ferredoxin, and BSA. The reaction was started by adding 5 mM BV and was stopped by placing the mixture on ice. Bilins were extracted from the incubation mixture using a SepPak C18 reversed-phase column and analyzed by HPLC on a Phenomenex Ultracarb 5 mm ODS20 4.6 mm 3 250 mm column with a 4.6 mm 3 30 mm guard column. The HPLC solvent was acetone: 20 mM formic acid (50:50, v/v), and the effluent was monitored at 560 nm for the first 11.5 min and at 380 nm for the remaining time. STDS, mixture of different bilin standards; HY2, metabolites obtained by mHY2; PcyA, metabolites obtained by PcyA_SYNY3; PebA, metabolites obtained by PebA_SYNPY; PebB, metabolites obtained by PebB_SYNPY; PebA 1 PebB, metabolites obtained by a 1:1 mixture of PebA_SYNPY and PebB_SYNPY. Symbols are used for better visualization of peaks. Single symbols indicate the 3Eisomer (except 15,16-DHBV and BV) and double symbols indicate the 3Z isomer, respectively.

HPLC Reveals Distinct Substrate/Product Specificity for Each Member of the HY2 Family HPLC analysis was performed to identify the bilin metabolites of the HY2 family members using a chromatographic system that is able to separate 3E and 3Z isomers of PB, PCB, and PEB. As shown in Example 1, recombinant mHY2 efficiently reduced BV by two electrons to yield a mixture of both isomers of PB. In comparison, both PcyA proteins converted BV to a mixture of the 3E and 3Z isomers of PCB, a four-electron reduction (FIG. 14). A time-course experiment was performed and revealed no evidence for other colored bilin intermediates (data not shown). Incubation of PebA_SYNPY with BV resulted in the formation of an early eluting product that was detectable only at 560 nm and not at 380 nm (FIG. 14). Optical spectroscopy revealed that this product had an absorption maximum at 575 nm in acetone:20 mM formic acid (50:50, v/v) (data not shown). Based on its absorption spectrum (data not shown), early retention time, and results shown below, this product was determined to be 15,16-DHBV. A similar absorption spectrum for DHBV has previously been published (Beale and Cornejo (1991b) *J. Biol. Chem.* 266: 22333–22340). In contrast to PebA_SYNPY, PebB_SYNPY was unable to metabolize BV (FIG. 14). Identical results were observed with the *N. punctiforme* PebA and PebB homologs (data not shown).

A mixture of PebA and PebB effectively converted all of the BV to two colored pigments, one purple (retention time 9 min) and the other pink (retention time 10.5 min), whose retention times differed from that of 15,16-DHBV (FIG. 14). Both bilin metabolites have absorption maxima in acetone: 20 mM formic acid (50:50, v/v) near 580 nm (data not shown). Because PebB could not metabolize BV, these results suggest either that the 15,16-DHBV product of PebA was metabolized by PebB to the purple and pink bilins or that PebB forms a complex with PebA to alter its product profile. That 15,16-DHBV was a substrate for PebB was demonstrated by incubation of PebB with HPLC-purified 15,16-DHBV. In this case, the same two bilin products were observed (data not shown). HPLC coelution experiments showed the purple and pink pigments to be the 3E and 3Z isomers of PEB, respectively (data not shown). Both pigments are chemically stable in the HPLC mobile phase, eluting as single peaks after purification and reinjection. Moreover, both HPLC-purified pigments form phytofluors upon incubation with apoCph1, indicating that these are configurational isomers of PEB. HPLC-purified 15,16-DHBV from the PebA-mediated reduction of BV, however, was unable to form a fluorescent adduct with apoCph1 (data not shown).

Biochemical studies of ferredoxin-dependent bilin reductases from algae and plants indicated that the 3Z isomers of PEB, PCB, and PΦB were the primary metabolites of these enzymes, with the formation of the 3E isomer requiring distinct bilin isomerase(s) (Beale and Cornejo (1991a) *J. Biol. Chem.* 266: 22328–22332; Beale and Cornejo (1991b) *J. Biol. Chem.* 266: 22333–22340; Beale and Cornejo (1991c) *J. Biol. Chem.* 266: 22341–22345; Cornejo and Beale (1997) *Photosynth. Res.* 51: 223–230). Our results show that both bilin isomers are produced with recombinant HY2, PcyA, and PebA/PebB proteins. We believe that the production of the 3E isomers occurred because of the presence of glutathione in the assay mixture and because of heating in the Speed-Vac concentrator. In this regard, glutathione-mediated 3Z to 3E isomerization of phycobilins has been reported for bilin reductases from *C. caldarium* (Beale and Cornejo (1991) *J. Biol. Chem.* 266: 22341–22345). Preliminary experiments performed with GST fusion proteins that did not come in contact with reduced glutathione or with proteins that were eluted from the affinity column by protease digestion greatly increased the relative amount of 3Z isomers produced (data not shown). Heating that occurred during concentration also contributed to the formation of the 3E isomers. If the drying time was reduced, only 3Z isomers were detected (data not shown). Therefore, we conclude that in all cases the 3Z isomers are the primary reaction product of these reductases and that the production of the 3E isomers occurs by non-enzyme-mediated side reactions caused by heat and reduced glutathione.

The HY2 Family of Bilin Reductases Are Ferredoxin Dependent

All of the reductive interconversions of BV and 15,16-DHBV presented here were dependent on reduced ferredoxin, which necessitated the inclusion of ferredoxin: NADP+ oxidoreductase and an NADPH-regenerating system in the assay mixture. Indeed, none of the reduced bilin metabolites were detectable via HPLC when either ferredoxin or the NADPH-regenerating system was omitted from the assay mixture (data not shown). These results are in agreement with the ferredoxin dependence of the bilin reductases from plants and algae (Beale (1993) *Chem. Rev.* 93: 785–802). Thus, this family of proteins constitutes a new class of bilin:ferredoxin oxidoreductases (EC 1.3.7.n).

Discussion.

Figure 11:
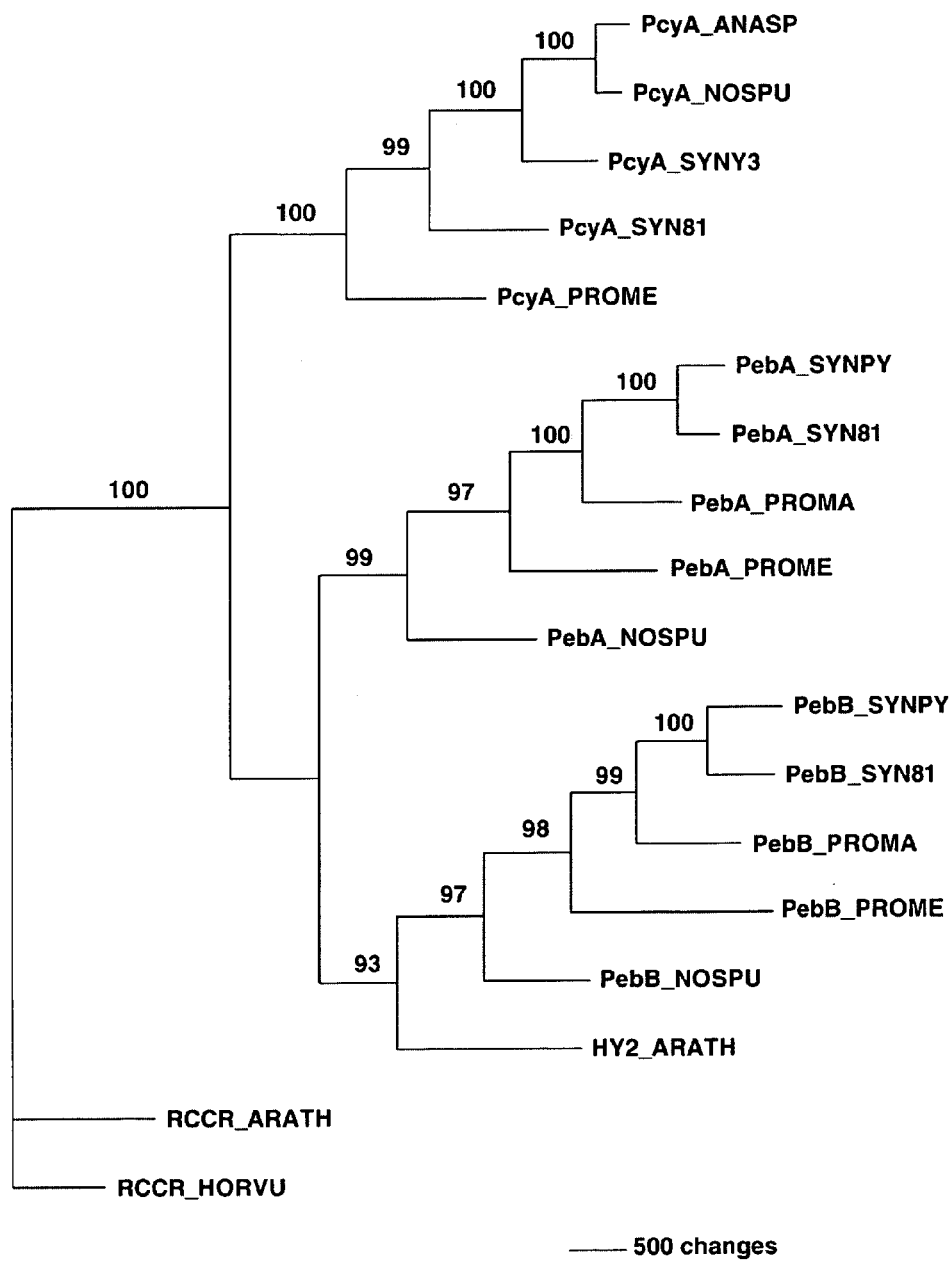
FIG. 11 shows a phylogenetic tree of the HY2 family of ferredoxin-dependent bilin reductases.

Using a combination of protein-based pattern searches of genomic databases, phylogenetic analysis, and biochemical characterization, these investigations establish that the HY2 family of ferredoxin-dependent bilin reductases can be subdivided into five classes: PcyA, PebA, PebB, HY2, and RCCR families (FIG. 11). This classification system is supported by the distinct substrate preference and double-bond regiospecificity of representative members of each bilin reductase subfamily. PcyA, PebA, and HY2 all recognize BV as a substrate, yet each yields different bilin products. PebB and RCCR possess unique bilin substrates (i.e., 15,16-DHBV and RCC, respectively), and neither metabolizes BV (Wüthrich et al. (2000) *Plant J.* 21: 189–198; this study). Biochemical analyses of representatives of the three new classes of bilin reductases identified here, PcyA, PebA, and PebB, document their involvement in the biosynthesis of the phycobiliprotein chromophore precursors PCB and PEB.

The PcyA Family of Ferredoxin-Dependent BV Reductases Plays a Key Role in PCB Biosynthesis In this investigation, we have documented that the pcyA genes of the cyanobacteria *Synechocystis* sp PCC6803, *Anabaena* sp PCC7120, and *N. punctiforme* (data not shown) encode bilin reductases that catalyze the four-electron reduction of BV to 3Z-PCB. PCB is the precursor of the chromophores of the phycobiliproteins phycocyanin and allophycocyanin, which are abundant in all three cyanobacteria. PcyA enzymes are atypical bilin reductases because all others catalyze two-electron reductions. Formally, these enzymes catalyze two-electron reductions of both the A and D rings of BV; however, we have not detected the production of semi-reduced intermediates such as PΦB and $18^1$, $18^2$-DHBV. Thus, it appears that the partially reduced intermediates are tightly bound to the enzyme. The direct conversion of BV to PCB in these cyanobacteria is in contrast to the proposed pathways of PCB biosynthesis in the red alga *C. caldarium*, which involves the intermediacy of PEB (Beale (1993) *Chem. Rev.* 93: 785–802), and in the green alga *M. caldariorum*, in which 3Z-PΦB is an isolable intermediate (Wu et al. (1997) *J. Biol. Chem.* 272: 25700–25705). pcyA-related genes also are present in the oxyphotobacterium *Prochlorococcus* sp MED4, an unanticipated observation in view of the lack of phycobiliproteins in this organism. Phylogenetic analyses place this oxyphotobacterial protein in the PcyA clade of PCB:ferredoxin oxidoreductases. We were also able to clone the *Prochlorococcus* sp MED4 pcyA gene and express it as an N-terminal GST fusion. We determined that recombinant PcyA_PROME was able to reduce BV to PCB in our standard phytochrome-based assay (data not shown). It therefore possesses the same enzymatic activity as all other studied PcyA enzymes.

peb Operons Encode Bilin Reductases Involved in PEB Biosynthesis

We have observed that the pebA and pebB genes of the cyanobacteria *Synechococcus* sp WH8020 and *N. punctiforme* encode bilin reductases that catalyze the conversions of BV to 15,16-DHBV and 15,16-DHBV to 3Z-PEB, respectively (FIG. 1). PebA therefore is a 15,16-DHBV: ferredoxin oxidoreductase, whereas PebB is a 3Z-PEB: ferredoxin oxidoreductase. Both activities are consistent with the pathway of PEB biosynthesis in the red alga *C. caldarium* (Beale (1993) *Chem. Rev.* 93: 785–802). The two peb genes also are found in the same operon in both phycoerythrin-producing cyanobacteria, and their close association with the major phycobiliprotein gene clusters supports their role in phycobilin biosynthesis (Wilbanks and Glazer (1993) *J. Biol. Chem.* 268: 1236–1241). We hypothesize that PebA and PebB function as a dual enzyme complex, in view of the synergistic metabolism of BV observed when the two enzymes are coincubated. A peb operon is not present in the genome of the cyanobacterium *Synechocystis* sp PCC6803, an organism that lacks phycoerythrin. This strongly suggests that PCB is synthesized in this cyanobacterium via the PcyA-dependent pathway, as opposed to the PEB pathway found in *C. caldarium* (Beale (1993) *Chem. Rev.* 93: 785–802). In this regard, biochemical analyses of crude extracts from *Synechocystis* sp PCC6803 provide no evidence for the production of PEB (Cornejo and Beale (1997) *Photosynth. Res.* 51: 223–230).

The MED4 and SS120 subspecies of the oxyphotobacteria *Prochlorococcus* also possess peb operons very similar to those of *Synechococcus* sp WH8020 and WH8102, except that the former possess upstream genes related to heme oxygenase. This strongly suggests that both oxyphotobacterial subspecies can synthesize PEB. In this regard, genes encoding the α and β subunits of a novel phycoerythrin have been identified in the SS120 subspecies of *Prochlorococcus* (Hess et al. 1996 R29R29, Hess et al. 1999 R30R30). It also has been shown that this unusual phycoerythrin plays a role in light harvesting in this ecotype (Lokstein et al. (1999) *Biochim. Biophys. Acta* 1410, 97–98), which is adapted for photoautotrophic growth at great ocean depths where light is limited. This observation is consistent with the lack of phycoerythrin genes in the high light-adapted MED4 ecotype. Although the enzymatic activities of *Prochlorococcus* PebA and PebB have not been determined experimentally, our phylogenetic reconstructions suggest that these proteins may be functional orthologs of the *Synechococcus* and *Nostoc* enzymes. Further analysis of the bilin biosynthetic pathways in *Prochlorococcus* and marine cyanobacteria such as *Synechococcus* sp WH8020 will be interesting, because the shorter wavelength-absorbing phycourobilin chromophores are major constituents of their phycoerythrins (Ong and Glazer (1991) *J. Biol. Chem.* 266: 9515–9527; Hess et al. (1996) *Proc. Natl. Acad. Sci., USA*, 93: 11126–11130). Although we have identified PCB and PEB biosynthetic enzymes in both organisms, it remains to be determined whether either these or other enzymes play a role in phycourobilin biosynthesis.

Phycobilin Isomerases: Are they Necessary?

PcyA, HY2, and PebB mediate bilin reductions that yield the 3Z isomer of their respective products. Because numerous studies have established that the more thermodynamically stable 3E isomers are substrates for assembly of the phycobiliprotein and phytochrome holoproteins, it has been proposed that there are unique 3Z/3E isomerases that mediate this interconversion (Beale (1993) *Chem. Rev.* 93: 785–802; Terry et al. (1993) *Arch. Biochem. Biophys.* 306: 1–15). It should be noted that the 3Z isomer of PB has been shown to be a substrate for apophytochrome (Terry et al. (1995) *J. Biol. Chem.* 270: 11111–11118); however, these investigators suggested that isomerization to the 3E isomer is necessary to yield the correct stereochemistry of the holophytochrome chromophore. Such an isomerase activity has been identified in extracts of the red alga *C. caldarium*; however, this reaction also can be mediated by reduced glutathione (Beale and Cornejo (1991) *J. Biol. Chem.* 266: 22333–22340). For this reason, the need for a 3Z/3E isomerase has been questioned. All of the hy mutant loci have now been cloned from *Arabidopsis*, and none of these genes appear to encode a bilin isomerase. Thus, the isomerization of 3Z-PΦB may occur chemically or may be catalyzed by a genetically redundant family of bilin isomerases.

X-ray crystallographic analyses of phycobiliproteins have revealed that the stereochemistries of the thioether linkages to distinct cysteine residues are not all the same (Schirmer et al. (1987) *J. Mol. Biol.* 196: 677–695; Schmidt et al. (1987) *Z. Naturforsch.* 42C, 845–848). Therefore, we propose that the different stereochemistries arise from the use of the 3Z and 3E isomers of the phycobilin precursor as substrates for assembly to distinct cysteinyl moieties. Beale and Cornejo (1991) *J. Biol. Chem.* 266: 22333–22340, have identified a bilin isomerase that catalyzes the conversion of 3Z-PEB to 3Z-PCB in *C. caldarium*, which appears to be the sole pathway for PCB biosynthesis in this organism. More recently, a lyase/isomerase from the cyanobacterium *Mastigocladus laminosus* was described that is involved in both the isomerization of PCB to phycoviolobilin and its covalent attachment to apophycoerythrocyanin (Zhao et al. (2000) *FEBS Lett.* 469: 9–13). On the basis of these results and the diversity of bilin isomers found in phycobiliproteins from marine cyanobacteria, cryptomonads, and oxyphotobacteria (Ong and Glazer (1991) *J. Biol. Chem.* 266: 9515–9527; Hess et al. (1996) *Proc. Natl. Acad. Sci., USA*, 93: 11126–11130; Wedemayer et al. (1996) *Photosynth. Res.* 48: 163–170), it is likely that numerous bilin isomerases are present in these oxygen-evolving photosynthetic organisms.

Molecular Evolution of the HY2 Family of Bilin Reductases

A single phylogenetic tree that is well supported with bootstrap replicates was obtained for the HY2 family (FIG. 11). This tree delineates four clades of bilin reductases, which is in good agreement with the enzymes' double-bond specificity for reduction. HY2 appears most closely related to the PebB clade of enzymes that catalyze a reduction of 15,16-DHBV to PEB. We predict that phytochromobilin synthases, because of their exquisite BV substrate specificity, will form a distinct clade when HY2 orthologs from other plant species are identified. The relatedness of HY2 and PebA enzymes is reasonable because both families mediate reduction of the vinyl pyrrole A ring to form the ethylidene moiety. We speculate that these two classes arose from a common ancestor that used BV as a substrate. This notion is based on the observation that the PebA family of bilin reductases also recognizes BV as a substrate.

Unlike HY2 and PebB, members of the PebA family target the 15,16 double bond of BV for reduction. To evolve the PebA and PebB/HY2 subfamilies, we envisage a duplication of a ferredoxin-dependent BV reductase gene and subsequent divergence in a marine cyanobacterium growing in a light-limited environment. Such an environment would provide the selection pressure favoring evolution of the biosynthetic pathway for PEB, whose incorporation into phycoerythrin extends the light-harvesting wavelength range of their phycobilisomes. Depending on the rooting of the HY2 family tree, the comparative branch lengths of the PebA and PebB/HY2 families on the phylogenetic tree suggest that the A ring reductases are more ancient, with the 15,16 reductases evolving more recently. On the basis of these inferences, we speculate that a cyanobacterial progenitor of plant chloroplasts possessed a bilin reductase with an A ring reductase regiospecificity. The progenitor of present day cyanobacteria likely would have possessed the ability to synthesize PCB, an essential component of their allophycocyanin-containing phycobilisome core. Thus, the common pebA/pebB ancestor might have resembled present-day pcyA genes, which encode atypical BV reductases that catalyze the four-electron reduction of BV to PCB. To date, pcyA genes appear to be present in all cyanobacteria, whereas a peb operon is lacking in the phycoerythrin-deficient cyanobacterium *Synechocystis* sp PCC6803.

The role of the pebA, pebB, and pcyA genes in *Prochlorococcus* sp MED4 remains a mystery. Members of this genus are distinguished by the presence of integral membrane antennae complexes that contain divinyl chlorophyll $a_2$ and $b_2$ and by the lack of phycobilisomes (Partensky et al. (1999) *Microbiol. Mol. Biol. Rev.* 63: 106–127). Functional phycoerythrins have been detected only for the SS120 subspecies. As such, these organisms have been thought by some to be descendants of the class of prokaryotic photosynthetic organisms whose endosymbiosis led to higher plant chloroplasts. Phylogenetic analyses using 16S rRNA indicate that this probably is not the case, because *Prochlorococcus* species appear more similar to marine *Synechococcus* species than to chloroplasts (Urbach et al. (1998) *J. Mol. Evol.* 46: 188–201). These analyses also suggest that *Prochlorococcus* evolved more recently from a phycobilisome-containing ancestor that resembled a marine *Synechococcus* species. The need for pebA, pebB, and pcyA genes for phycobilin biosynthesis in this ancestor is self-evident, and such genes may not yet have been lost from *Prochlorococcus* species. It is conceivable that these BV reductases are required to make bilin chromophore precursors of light receptors, such as the phytochromes (Hughes and Lamparter (1999) *Plant Physiol.* 121: 1059–1068). Although phytochrome-like genes are abundant in some cyanobacterial genomes, none are present in the genome of *Prochlorococcus* sp MED4 (data not shown). Alternatively, BV reductases may be needed to drive heme oxygenase, whose role in iron metabolism is well documented (Poss and Tonegawa (1997a) *Proc. Natl. Acad. Sci., USA*, 94: 10919–10924; Poss and Tonegawa (1997b) *Proc. Natl. Acad. Sci., USA*, 94: 10925–10930; Richaud and Zabulon (1997) *Proc. Natl. Acad. Sci., USA*, 94: 11736–11741; Schmitt (1997) *J. Bacteriol.* 179: 838–845).

In addition to the bilin reductases involved in phytobilin biosynthesis, a separate class exists of bilin reductases that are involved in chlorophyll degradation (Hörtensteiner et al. (1998) *J. Biol. Chem.* 273, 15335–15339; Wüthrich et al. (2000) *Plant J.* 21: 189–198). The pathway of chlorophyll degradation that occurs during plant senescence is similar to the heme degradation pathway (Matile and Hörtensteiner (1999) *Annu. Rev. Plant Physiol. Plant Mol. Biol.* 50: 67–95). After dephytylation and magnesium removal, the chlorophyll macrocycle ring is opened by a monooxygenase that has yet to be cloned (Hörtensteiner et al. (1998) *J. Biol. Chem.* 273, 15335–15339). This is followed by a ferredoxin-dependent reduction of the bilin product catalyzed by the RCCR (Hörtensteiner et al. (2000) Plant Biol2. : 63–67; Wüthrich et al. (2000) *Plant J.* 21: 189–198). RCCRs are the most diverged members of the ferredoxin-dependent bilin reductase family. Indeed, these enzymes have markedly different substrate specificities. It is notable that RCCRs catalyze a reduction very similar to that mediated by the PebA family (i.e., a 15,16 double-bond reduction). The structural determinants that are responsible for RCCR's unique substrate specificity and double-bond regiospecificity will be interesting to discover. Presumably, chlorophyll catabolism would be important for chlorophyll-containing prokaryotes; however, to date, RCCR genes are not readily identifiable in the genomes of any photosynthetic prokaryotes. It is possible that RCCR genes were lost, or alternately, that they evolved more recently from an HY2-like gene in the chloroplast endosymbiont progenitor, because they are found in cryptogams and plants (Hörtensteiner et al. (2000) Plant Biol. 2: 63–67).

Mechanistic Implications

Ferredoxin-dependent bilin reductase catalyzes two- and four-electron reductions of linear tetrapyrroles. Because ferredoxin is a one-electron carrier, these enzymes are mechanistically quite different from the NAD(P)H-dependent BVR/BvrD family of BV reductases. Preliminary analyses to date have failed to identify a metal or flavin cofactor in any of the recombinant enzymes reported here, suggesting that electrons are transferred directly to the bilin moiety, possibly via reduction of an amino acid residue within the enzyme. Although this finding suggests the presence of bilin radical intermediates, additional experiments are needed to assess this hypothesis. The oxygen sensitivity of RCCR supports the hypothesis that bilin radicals, which react with molecular oxygen, are produced during RCC catalysis (Wüthrich et al. (2000) *Plant J.* 21: 189–198).

Examination of highly conserved residues in the entire HY2 family and those within each of the five classes of bilin reductases provides information regarding residues important to the protein structure, ferredoxin interaction site, and substrate/product specificity. In this regard, only a small number of residues are conserved in the entire HY2 family of enzymes. These include hydrophobic residues at positions 137, 157, 158, 256, and 314, Pro-151, Phe-221, Ser-222, and Asp-171 (FIG. 10). The notable lack of conserved basic residues suggests that the propionyl moieties of the bilin substrates do not form salt linkages with the enzymes. The conserved hydrophobic residues proline and phenylalanine are likely to be involved in overall protein structure (i.e., folding). Alternately, they may form hydrophobic interactions with conserved regions of the various bilin substrates. The loss-of-function hy2-1 and hy2-104 alleles of phytochromobilin synthase from *Arabidopsis* support the critical role of Pro-151 in HY2's structure. The conserved serine and aspartate residues likely play catalytic roles, such as hydrogen bonding with the substrate and/or substrate protonation to make the bound bilin a better electron acceptor.

Despite the wide divergence of the HY2 family, we believe that these conserved residues indicate that the active sites of all members of this class are similar. We speculate that the distinct double-bond reduction specificities of the BV reductases (i.e., PcyA, PebA, HY2), the 15,16-DHBV reductases (i.e., PebB), and the RCCR families reflect the positioning of the respective substrates within the catalytic pocket. Because the A/B and C/D rings of BV are very similar but not identical, it is conceivable that the substrate binding sites of the PebA and HY2 enzymes are tailored to position BV in opposite orientations, favoring electron transfer to the bilin C/D ring or A ring, respectively. If this is true, then the PebB class might tether its 15,16-DHBV substrate in an orientation similar to that of the HY2 family, whereas RCC might be bound to RCCR in a manner similar to that in which BV is bound to PebA. Future studies will address the unique substrate/product specificity using domain swapping, site-directed mutagenesis, synthetic biliverdin substrates, and x-ray crystallography.

Biotechnological Implications

The availability of genes for bilin reductases that mediate the biosynthesis of PΦB, PCB, and PEB provides us with useful tools for numerous biotechnological applications. The ability to engineer the biosynthesis of PEB in any BV-producing organism is now feasible via the introduction of one or two genes. In this way, phytofluors potentially can be produced in any ferredoxin-containing organism. Coexpression of bilin reductase genes with apophytochromes should enable us to produce holophytochromes in bacteria and yeast. This will facilitate not only three-dimensional structural analysis of phytochrome but also the reconstruction of phytochrome signaling in a nonplant system in which we can exploit the power of molecular genetic analyses. This approach has proven invaluable for the structure-function analysis of the steroid hormone receptor family. By introducing the pcyA gene into wild-type and chromophore-deficient mutant plants, we also should be able to change the wavelength specificity of phytochrome, which may favorably alter plant growth and development in the field environment. Introduction of the pebA and pebB genes into plants potentially will shunt the conversion of BV to PEB, yielding photomorphogenetically challenged plants with fluorescent phytochromes. This would be especially useful for the analysis of the temporal and spatial patterns of phytochrome expression in plants.

Methods.

Reagents

All chemicals, including glutathione agarose, were purchased from Sigma (St. Louis, Mo.) and were American Chemical Society grade or better. Restriction enzymes and Taq polymerase were from Gibco BRL (Cleveland, Ohio). HPLC-grade acetone and 80% formic acid were purchased from Fisher Scientific (Pittsburgh, Pa.). The expression vector pGEX-6P-1 and PreScission protease were obtained from Amersham Pharmacia Biotech (Piscataway, N.J.). Centricon-10 concentrator devices were purchased from Amicon (Beverly, Mass.).

Bioinformatics

Protein and nucleic acid database searches were performed using programs at publicly available World Wide Web sites. Preliminary sequence data were obtained from the Department of Energy Joint Genome Institute (http://spider.jgi-psf.org/JGI_microbial/html/). Multiple sequence alignments were performed using the programs CLUSTAL W (Higgins et al. 1996 R21R21), GENEDOC (http://www.psc.edulbiomed/genedoc), and MEME (Bailey and Elkan (1995) pp. 21–29 In Proceedings of the Third Inter-national Conference on Intelligent Systems for Molecular Biology, Menlo Park, Calif.: American Association of Artificial Intelligence Press) to guide hand alignments. Phylogenetic analysis of the HY2-related family of proteins based on the alignment shown in FIG. 10 was conducted using a heuristic parsimony search with a modified PAM250 weighting matrix (Dayhoff et al. (1978) Pp 345–352 In: *Atlas of Protein Sequences and Structure*, M. O. Dayhoff, ed, Washington, D.C.: National Biomedical Research Foundation) using the program PAUP* version 4.0 (Swofford (1993) *J. Gen. Physiol.* 102: 9A).

Because there are negative values in the PAM250 matrix, the most negative penalty was set equal to zero, and all other values were increased correspondingly. Scores for transitions to and from gaps were not defined in the original matrix; they were set equal to the most costly transition (25) defined in the matrix. Characters 1 to 65 and 323 to 368 in the alignment were excluded from our analysis because they correspond to N- and C-terminal extensions not common to all members of the HY2 family (i.e., plastid transit peptide found on HY2 and red chlorophyll catabolite reductase (RCCR), C-terminal extension found only on HY2). For *Hordeum vulgare* RCCR, missing characters 65 to 116 were replaced with question marks, which were weighted as zero. A rescaled consistency index was used for character weighting.

Construction of Expression Vectors

HY2-related genes from *Synechocystis* sp PCC6803, *Synechococcus* sp WH8020, and *Anabaena* sp PCC7120 were amplified from chromosomal DNA via polymerase chain reaction using the following primers, which contained the indicated and underlined restriction sites: Synechocystis pcyA, BamHIfwd: 5'-AAG GAT CCA TGG CCG TCA CTG ATT TAA G-3' (SEQ ID NO:19), SalIrev: 5'-ACG CGT CGA CTA TTG GAT AAC ATC AAA TAA GAC-3' (SEQ ID NO:20); *Synechococcus* pebA, EcoRIfwd: 5'-GGA ATT CAT CTT TGA TTC ATT TCT CAA TG-3' (SEQ ID NO:21), NotIrev: 5'-ATA GTT AGC GGC CGC TCA TTT GTG AGA GGA GGA GGC-3' (SEQ ID NO:22); *Synechococcus* pebB, EcoRIfwd: 5'-GGA ATT CAT CAC AAA TCA AAG ATT CAA AAG C-3' (SEQ ID NO:23), NotIrev: 5'-ATA GTT AGC GGC CGC TTA TAG ATC AAA AAG CAC AGT GTG G-3' (SEQ ID NO:24); and Anabaena pcyA, EcoRIfwd: 5'-GGA ATT CAT CTC ACT TAC TTC CAT TCC CTC-3' (SEQ ID NO:25), NotIrev: 5'-ATA GTT AGC GGC CGC TTA TTC TGG -GA GAT CAA ATA AC-3' (SEQ ID NO:26).

The polymerase chain reaction products were then cut with the indicated enzymes and inserted into similarly restricted pGEX-6P-1. The integrity of the plasmid constructs was verified by complete DNA sequence determination of the insert (Davis Sequencing, Davis, Calif.). All of the constructs place the HY2-related gene downstream of and in frame with the glutathione S-transferase (GST) gene of *Schistosoma japonicum* under the control of a Ptac promoter. A recognition sequence for PreScission protease is located upstream of the cloned gene. Proteolytic cleavage yields the native protein with a small N-terminal extension. In all cases, the original initiation methionine was changed to an isoleucine.

Expression and Purification

Expression and purification were performed according to instructions supplied by the manufacturer (Amersham Pharmacia Biotech) and as described in Example 1. Between 1 and 10 mg of purified protein was obtained per liter of bacterial culture.

Protein Determination

Protein concentration was determined by the Bradford method with BSA as a standard (Bradford 1976 R48R48) or by measuring the absorbance at 280 nm and using the calculated 280 nm for each individual protein (Gill and von Hippel (1989) *Anal. Biochem.* 182: 319–326).

Standard Bilin Reductase Activity Assay

Assays for bilin reductase activity were performed as described for PΦB synthase (see Example 1).

Direct HPLC Analysis

Bilin reductase assay mixtures were loaded onto a Waters (Milford, Mass.) C18 Sep-Pak Light preconditioned as follows: 3-mL wash with acetonitrile to wet the Sep-Pak, 3-mL wash with MilliQ water, and 3-mL wash with 50 mM 4-methylmorpholine/glacial acetic acid, pH 7.7. After the sample was loaded onto the Sep-Pak, it was washed with 3 mL of 4-methylmorpholine/glacial acetic acid, pH 7.7, followed by 3 mL of 0.1% (v/v) trifluoroacetic acid. The bilin metabolites were then eluted from the Sep-Pak with 2 mL of 100% acetonitrile. The eluate was dried using a Speed-Vac lyophilizer (Savant Instruments Inc., Farmingdale, N.Y.), and the dried samples were analyzed by HPLC. Samples were first dissolved in 10 μL of DMSO and then diluted with 200 μL of the HPLC mobile phase (50:50 v/v acetone:20 mM formic acid). After the samples were dissolved, they were centrifuged briefly to collect the sample, passed through a 0.45-μm polytetrafluoroethylene syringe filter, and chromatographed using a Varian (Palo Alto, Calif.) 5000 liquid chromatograph. The HPLC column used for all of the analyses was a Phenomenex (Torrance, Calif.) Ultracarb 5-μm ODS20 4.6×250-mm analytical column with a 4.6× 30-mm guard column of the same material. The mobile phase used with this column was acetone:20 mM formic acid (50:50, v/v). The flow rate was 0.8 mL/min. The eluate was monitored at 560 nm for the first 11.5 min and at 380 nm for the remaining time using a Varian UV100 flow-through absorbance detector. Peak areas were quantitated using a Hewlett-Packard (Palo Alto, Calif.) model 3365 Chemstation II.

Coupled Spectrophotometric and Spectrofluorometric Analysis

An aliquot of 20 µg of crude recombinant Cph1 apoprotein (Yeh and Lagarias (1998) *Proc. Natl. Acad. Sci., USA*, 95: 13976–13981) was added to 1 mL of bilin reductase assay mixture under green safelight. Mixtures were incubated for 30 min at room temperature to permit phytobilin binding. Phytochrome difference spectra were obtained as described previously (Terry and Lagarias (1991) *J. Biol. Chem.* 266: 22215–22221). A spectrofluorometric assay was used to detect the formation of intensely fluorescent phycoerythrobilin (PEB) adducts of Cph1 (Murphy and Lagarias (1997) *Curr. Biol.* 7: 870–876). Emission spectra were obtained with an excitation wavelength of 545 nm using an SLM Aminco Bowman AB2 spectrofluorometer (Spectronic Instruments Inc., Rochester, N.Y.).

Example 3

Production of Functional Phytochrome in Living Cells

In the higher plants two enzymes are committed to the biosynthesis of phytochromobilin PΦB—the chromophore precursors of phytochrome. These enzymes are heme oxygenase (encoded by HY1 in *Arabidopsis thaliana* (Muramoto et al. (1999) *Plant Cell*, 11: 335–347)), which catalyzes the ferredoxin-dependent conversion of heme to biliverdin IXα (BV), and phytochromobilin:ferredoxin oxidoreductase (PΦB synthase) in *Arabidopsis* (encoded by HY2 in *Arabidopsis*), which catalyzes the ferredoxin-dependent conversion of BV to PΦB. A homolog of the HY1 protein, HO1 which is encoded by Cyanobase Locus SLL1184 of the cyanobacterium *Synechocystis* sp. PCC 6803 has been shown to be a functional ferredoxin-dependent heme oxygenase. Here we show that co-expression of the biosynthetic enzymes HO1 and HY2 together with the cyanobacterial phytochrome Cph1 yields the production of photoreversible holophytochrome in the bacterium *Escherichia coli*, with spectroscopic properties consistent with the formation of a phytochromobilin-adduct.

This work involved the production of synthetic operon comprised of HO1 from *Synechocystis* sp. PCC6803 and the mature HY2 coding region (mHY2) from *Arabidopis thaliana* that lacks the plastid targeting sequence. The cloning of HO1 and mHY2 open reading frames into the plasmid pPROLarA122 (Clontech Laboratories) places this operon under regulatory control of a dual Ara/Lac promoter. Upon introduction of this plasmid into *E. coli* cells harboring the Cph1-expression plasmid, pBAD/Cph1(514), in which Cph1(N514) is under regaulatory control of a Ara promoter, the production of photoactive holophytochrome in vivo was determined.

Methods.

Plasmid Construction.

The synthetic operon consisting of HO1 and pcyA coding regions was cloned in the expression vector pPROlarA122 to produce the plasmid pPROlarA122/HO1-RBS-SLR0116 (SEQ ID NO:27) as follows. The HO1 gene from *Synechocystis* sp. PCC6803 was first PCR amplified with the sense primer Pho1-S1K, 5'-ATC GGT ACC ATG AGT GTC AAC TTA GCT TC-3' (SEQ ID NO:28) (containing a KpnI restriction site) and antisense primer Pho1-ArB, 5'-ATT GGA TCC TTT CTC CTC TTT AAC TAG CCT TCG GAG GTG GCG A-3' (SEQ ID NO:29) (containing a synthetic ribosome binding site upstream of a BamHI restriction site) using chromosomal DNA from *Synechocystis* sp. PCC6803 as a template. The reaction was carried out using a standard reaction mix, Taq polymerase, and a 30 cycle run with an annealing temperature of 50° C. The gene was then cloned into TA cloning plasmid, pCR2.1 (Invitrogen), producing plasmid pCR2.1/HO1-RBS (not shown).

The synthetic operon consisting of HO1 from *Synechocystis* sp PCC6803 (Cornejo et al. (1998) *Plant J.* 15: 99–107) and mHY2 coding regions was produced by cloning mHY2 into the plasmid pCR2.1/HO1-RBS to produce plasmid pCR2.1/HO1-RBS-HY2. Specifically, the mHY2 cDNA from *Arabidopsis* was PCR-amplified using plasmid DNA from the clone pGEX-mHY2 (Example 2), which contains the full length mHY2 cDNA minus the transit peptide in a GST-fusion vector, with sense primer mHY2-EcoRV: 5'-CGG ATA TCA TGT CCC CTA T ACT A-3' (SEQ ID NO:30) and the antisense primer, mHY2-Not1: 5'-GCG CGG CCG CTT AGC CGA TAA ATT GTC C-3' (SEQ ID NO:31) under standard conditions. The reaction was carried out using a standard reaction mix, Pfu polymerase, and a 35 cycle run with an annealing temperature of 55° C. The PCR product was restricted with EcoRV and NotI and then subcloned in to the plasmid pCR2.1/HO1-RBS to produce the plasmid pCR2.1/HO1-RBS-HY2. Finally pCR2.1/HO1-RBS-HY2 was restricted with KpnI/NotI and the resulting fragment was ligated with KpnI/NotI restricted pPROLarA122 (Clontech Laboratories) resulting in production of pPROLarA122/HO1-RBS-HY2.

*E. coli* Strains, Media, and Transformation.

The plasmid pPROLarA122/HO1-RBS-HY2 was transformed into *E. coli* strain LMG194 (Invitrogen) competent cells containing the apophytochrome expression plasmid, pBAD/Cph1(514). Dual ampicillin and kanamycin selection using minimal RM media was performed to isolate transformants.

Protein expression.

The *E. coli* strain LMG194 containing both plasmids pBAD/Cph1(514) and pPROlarA122/HO1-RBS-HY2 was grown overnight at 37° C. in 3 ml RM media containing 25 µg/ml kanamycin and 50 µg/ml ampicillin. A 1 ml aliquot of this culture was transferred to 100 ml of RM media and grown at 37° C. to an $OD_{600}$ of approximately 0.5. 50 ml of this culture was then transferred to 450 ml LB media containing 25 µg/ml kanamycin and 50 µg/ml ampicillin. IPTG was added to a final concentration of 1 mM to induce expression of the synthetic operon. After incubation for 1 h at 30° C., arabinose was added to a final concentration of 0.002% to induce expression of apoCph1. The culture was grown at 30° C. for 5 h, after which time cells were collected by centrifugation and resuspended in 10 ml lysis buffer (50 mM Tris-HCl, pH 8.0, 100 mM NaCl, 0.05% v/v NP40, 2 µg/ml leupeptin, 2 mM benzamidine, 2 mM PMSF, 1 mM DTT, 3 µg/ml pepstatin A). A cell lysate was obtained by lysing the cells at 10,000 psi with a French Press. After insoluble material was removed by centrifugation, the crude homogenate was placed on ice at 4° C. and examined for holophytochrome spectrophotometrically.

Protein Purification:

The crude soluble fraction was run over a Talon (Clontech) metal affinity chromatography column (5 ml bed volume), washed with 20 ml extraction/wash buffer, and eluted with 2 bed volumes 1× elution buffer (EW buffer containing 200 mM imidazole). The resulting solution was dialyzed overnight against 2 liters of 10 mM HEPES pH 7.5, and then concentrated using an Amicon ultrafiltration cell.

Results & Discussion.

Figure 15:
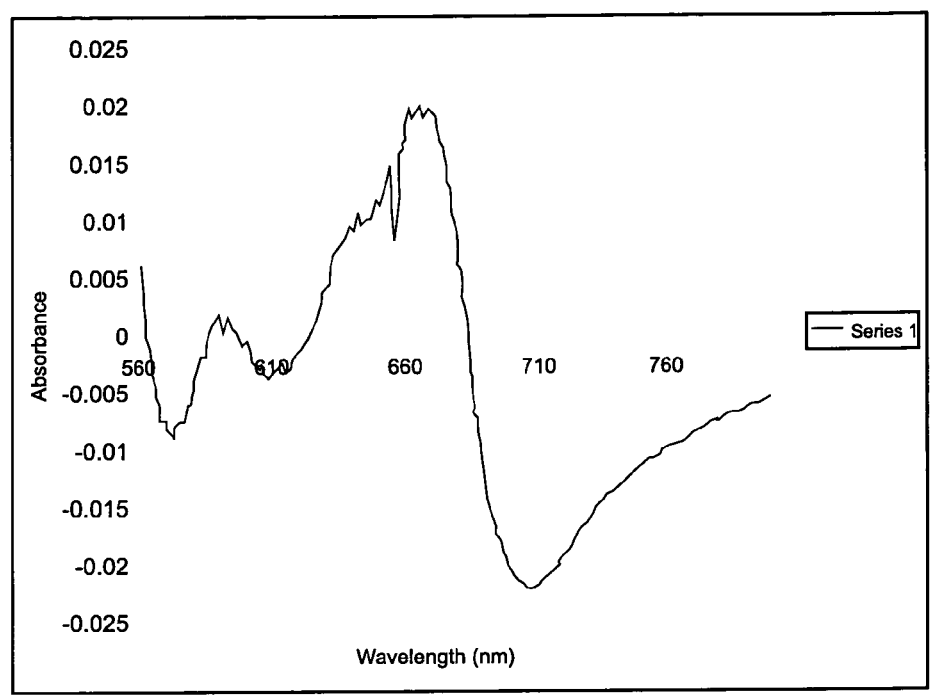
FIG. 15 shows holophytochrome difference spectrum taken of the protein purified from *E. coli* cells strain LMG194 induced to express apoCph1, HO1 and HY2.
Figure 16:
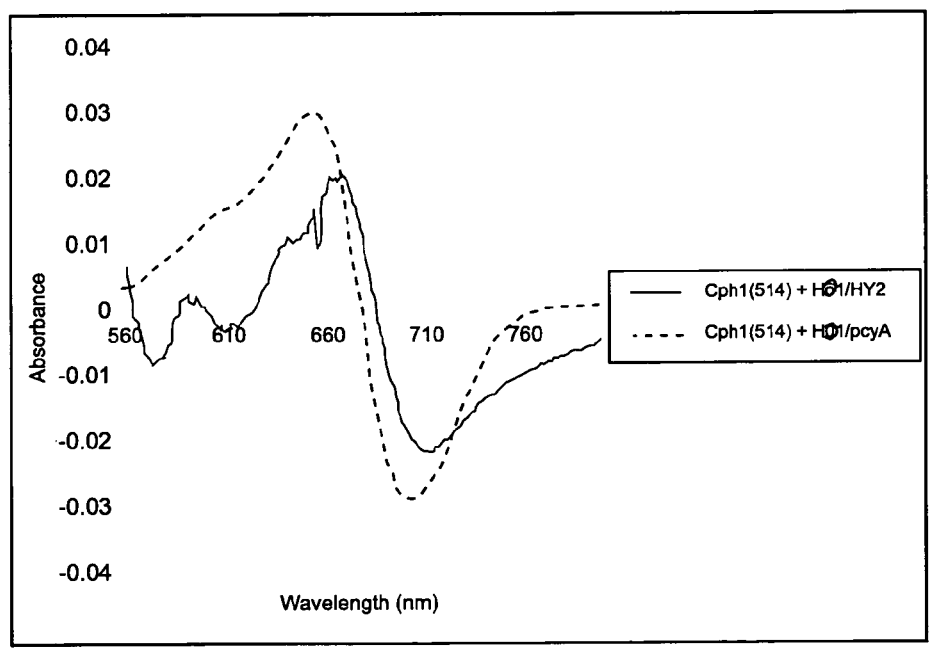
FIG. 16 shows a comparison of holophytochrome difference spectra taken of the protein isolated from *E. coli* cells strain LMG194 induced to express apoCph1 with either HO1 and HY2, or HO1 and PcyA.

After 5 h induction at 30° C., cultures containing both pBAD/Cph1(514) and pPROlarA122/HO1-RBS-HY2 plasmids turned blue-green. As shown in the difference spectrum (FIG. 15), co-expression of pBAD/Cph1(514) and pPROlarA122/HO1-RBS-HY2 yielded crude cell extracts containing photoactive holophytochrome. The spectrum of purified holoCph1(N514) from these cells reveals absorption maxima for the Pr form at 660 nm and for the Pfr form at 710 nm, consistent with the formation of a phytochromobilin (PΦB) adduct in vivo, as opposed to the blue-shifted phycocyanobilin (PCB) adduct formed in Cph1(N514)-expressing *E. coli* cells coexpressing the PCB operon, i.e. HO1 and PcyA (FIG. 16) (Yeh, et al. (1997) *Science*, 277: 1505–1508).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. An isolated nucleic acid comprising a nucleic acid that specifically hybridizes with a nucleic acid encoding the polypeptide of SEQ ID NO:33 under stringent conditions comprising 0.2×SSC wash at 65° C. and that encodes a polypeptide having bum reductase activity.

2. A host cell transformed with the vector of claim 1.

3. A vector comprising the nucleic acid of claim 2.

* * * * *

UNITED STATES PATENT AND TRADEMARK OFFICE
CERTIFICATE OF CORRECTION

PATENT NO. : 7,033,806 B2
APPLICATION NO. : 09/870406
DATED : April 25, 2006
INVENTOR(S) : John Clark Lagarias et al.

It is certified that error appears in the above-identified patent and that said Letters Patent is hereby corrected as shown below:

On the Title page, Item (75), please correct inventor name:
change
"Takayuki Kochi" to read --Takayuki Ko<u>h</u>chi--

Signed and Sealed this

Twenty-second Day of August, 2006

JON W. DUDAS
*Director of the United States Patent and Trademark Office*

SEQUENCE LISTING

<160> NUMBER OF SEQ ID NOS: 57

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
acagcgagat tcaaaggtcc attaaccgga                30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
gggcttacag tgatatctgc aagacttcta                30

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
taatgcttgc gacaaacagg                20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gttcatctca gggccaaaaa                20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gctttcagaa atcagacctc aa                22

```
<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ctggtgtggt tgatcgaatc t                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ctgccaagct tcatttggtt                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcaggagctg cagacaatct                                                20

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
caatgcaggt ttaacttcag ca                                             22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccatgggaaa gtctgcaaat                                                20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11 tcaagcccatt ttccaacatc                                               20

<210> SEQ ID NO 12
<211> LENGTH: 20
<212> TYPE: DNA
<213> ORGANISM: Artificial Sequence
<220> FEATURE:
<223> OTHER INFORMATION: Primer
```

```
<400> SEQUENCE: 12
ttccccatct gaactcaacc                                                20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aatgatgcat ggtgttggtg                                                20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gctcgaggaa aagtcatcca                                                20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cgtttgtctc actgaaactg                                                20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caatcatctt gaaatgcaga                                                20

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
gaagatctgt ctctgctgtg tcgtataagg                                     30

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
tcccccgggt tagccgataa attgtcctgt taaatc                              36
```

```
<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
aaggatccat ggccgtcact gatttaag                                    28

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
acgcgtcgac tattattgga taacatcaaa taagac                           36

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
ggaattcatc tttgattcat ttctcaatg                                   29

<210> SEQ ID NO 22
<211> LENGTH: 36
<212> TYPE: DNA
<213> ORGANISM: Artificial Sequence
<220> FEATURE:
<223> OTHER INFORMATION: Primer

<400> SEQUENCE: 22
atagttagcg gccgctcatt tgtgagagga ggaggc                           36

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
ggaattcatc acaaatcaaa gattcaaaag c                                31

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
atagttagcg gccgcttata gatcaaaaag cacagtgtgg                       40

<210> SEQ ID NO 25
<211> LENGTH: 30
<212> TYPE: DNA
<213> ORGANISM: Artificial Sequence
<220> FEATURE:
<223> OTHER INFORMATION: Primer
```

-continued

<400> SEQUENCE: 25
ggaattcatc tcacttactt ccattccctc                                         30

<210> SEQ ID NO 26
<211> LENGTH: 37
<212> TYPE: DNA
<213> ORGANISM: Artificial Sequence
<220> FEATURE:
<223> OTHER INFORMATION: Primer

<400> SEQUENCE: 26
atagttagcg gccgcttatt ctgggagatc aaataac                                 37

<210> SEQ ID NO 27
<211> LENGTH: 3997
<212> TYPE: DNA
<213> ORGANISM: Artificial Sequence
<220> FEATURE:
<223> OTHER INFORMATION: Plsmid pPROLarA122/H01-RBS-SLR0116

<400> SEQUENCE: 27

| | |
|---|---|
| cagaattcat taaagaggag aaaggtacca tgagtgtcaa cttagcttcc cagttgcggg | 60 |
| aagggacgaa aaaatcccac tccatggcgg agaacgtcgg cttttgtcaaa tgcttcctca | 120 |
| agggcgttgt cgagaaaaat tcctaccgta agctggttgg caatctctac tttgtctaca | 180 |
| gtgccatgga agaggaaatg gcaaaattta aggaccatcc catcctcagc cacatttact | 240 |
| tccccgaact caaccgcaaa caaagcctag agcaagacct gcaattctat tacggctcca | 300 |
| actggcggca agaagtgaaa atttctgccg ctggccaagc ctatgtggac cgagtccggc | 360 |
| aagtggccgc tacggcccct gaattgttgg tgcccattc ctacacccgt tacctggggg | 420 |
| atcttttccgg cggtcaaatt ctcaagaaaa ttgcccaaaa tgccatgaat ctccacgatg | 480 |
| gtggcacagc tttctatgaa tttgccgaca ttgatgacga aaaggctttt aaaaatacct | 540 |
| accgtcaagc tatgaatgat ctgcccattg accaagccac cgccgaacgg attgtggatg | 600 |
| aagccaatga cgcctttgcc atgaacatga aaatgttcaa cgaacttgaa ggcaacctga | 660 |
| tcaaggcgat cggcattatg gtgttcaaca gcctcacccg tcgccgcagt caaggcagca | 720 |
| ccgaagttgg cctcgccacc tccgaaggct agttaaagag gagaaaggat ccatggccgt | 780 |
| cactgattta agtttgacca attcttccct gatgcctacg ttgaacccga tgattcaaca | 840 |
| gttggccctg cgatcgccg ctagttggca agtttacccc tcaagcccct atcaattgcc | 900 |
| ggaggatttg ggctacgtag aaggccgcct ggaaggggaa agttagtga ttgaaaatcg | 960 |
| gtgctaccaa cgccccagt tcgcaaaat gcatttggag ttggccaagg tgggcaaagg | 1020 |
| gttggatatt ctccactgtg taatgtttcc tgagccttta tacggtctac ctttgtttgg | 1080 |
| ctgtgacatt gtggccggcc ccggtggagt aagtgcggct attgcggatc tatcccccac | 1140 |
| ccaaagcgat cgccaattgc ccgcagcgta ccaaaaatca ttggcagagc taggccagcc | 1200 |
| agaatttgag caacaacggg aattgccccc ctggggagaa atattttctg aatattgttt | 1260 |
| attcatccgt cccagcaatg tcactgaaga agaaagattt gtacaaaggg tagtggactt | 1320 |
| tttgcaaatt cattgtcacc aatccatcgt tgccgaaccc ttgtctgaag ctcaaacttt | 1380 |
| ggagcaccgt caggggcaaa ttcattactg ccaacaacaa cagaaaaatg ataaaacccg | 1440 |
| tcgggtactg gaaaaagctt ttggggaagc ttgggcggaa cggtatatga gccaagtctt | 1500 |
| atttgatgtt atccaataat ctagaggcat caaataaaac gaaaggctca gtcgaaagac | 1560 |
| tgggcctttc gttttatctg ttgtttgtcg gtgaacgctc tcctgagtag gacaaatccg | 1620 |

-continued

```
ccgccctaga cctaggggat atattccgct tcctcgctca ctgactcgct acgctcggtc    1680
gttcgactgc ggcgagcgga aatggcttac gaacggggcg gagatttcct ggaagatgcc    1740
aggaagatac ttaacaggga agtgagaggg ccgcggcaaa gccgttttc cataggctcc    1800 gcccccctga caagcatcac gaaatctgac gctcaaatca gtggtggcga aacccgacag    1860
gactataaag ataccaggcg tttcccctg gcggctccct cgtgcgctct cctgttcctg    1920
cctttcggtt taccggtgtc attccgctgt tatggccgcg tttgtctcat tccacgcctg    1980
acactcagtt ccgggtaggc agttcgctcc aagctggact gtatgcacga accccccgtt    2040
cagtccgacc gctgcgcctt atccggtaac tatcgtcttg agtccaaccc ggaaagacat    2100
gcaaaagcac cactggcagc agccactggt aattgattta gaggagttag tcttgaagtc    2160
atgcgccggt taaggctaaa ctgaaaggac aagttttggt gactgcgctc ctccaagcca    2220
gttacctcgg ttcaaagagt tggtagctca gagaaccttc gaaaaaccgc cctgcaaggc    2280
ggttttttcg ttttcagagc aagagattac gcgcagacca aaacgatctc aagaagatca    2340
tcttattaat cagataaaat attactagat ttcagtgcaa tttatctctt caaatgtagc    2400
acctgaagtc agccccatac gatataagtt gttactagtg cttggattct caccaataaa    2460
aaacgcccgg cggcaaccga gcgttctgaa caaatccaga tggagttctg aggtcattac    2520
tggatctatc aacaggagtc caagcgagct ctcgaacccc agagtcccgc tcagaagaac    2580
tcgtcaagaa ggcgatagaa ggcgatgcgc tgcgaatcgg gagcggcgat accgtaaagc    2640
acgaggaagc ggtcagccca ttcgccgcca agctcttcag caatatcacg ggtagccaac    2700
gctatgtcct gatagcggtc cgccacaccc agccggccac agtcgatgaa tccagaaaag    2760
cggccatttt ccaccatgat attcggcaag caggcatcgc catgggtcac gacgagatcc    2820
tcgccgtcgg gcatgcgcgc cttgagcctg gcgaacagtt cggctggcgc gagcccctga    2880
tgctcttcgt ccagatcatc ctgatcgaca agaccggctt ccatccgagt acgtgctcgc    2940
tcgatgcgat gtttcgcttg gtggtcgaat gggcaggtag ccggatcaag cgtatgcagc    3000
cgccgcattg catcagccat gatggatact ttctcggcag gagcaaggtg agatgacagg    3060
agatcctgcc ccggcacttc gcccaatagc agccagtccc ttcccgcttc agtgacaacg    3120
tcgagcacag ctgcgcaagg aacgcccgtc gtggccagcc acgatagccg cgctgcctcg    3180
tcctgcagtt cattcagggc accggacagg tcggtcttga caaaaagaac cgggcgcccc    3240
tgcgctgaca gccggaacac ggcggcatca gagcagccga ttgtctgttg tgcccagtca    3300
tagccgaata gcctctccac ccaagcggcc ggagaacctg cgtgcaatcc atcttgttca    3360
atcatgcgaa acgatcctca tcctgtctct tgatcagatc ttgatcccct gcgccatcag    3420
atccttggcg gcaagaaagc catccagttt actttgcagg gcttcccaac cttaccagag    3480
ggcgccccag ctggcaattc cgacgtctgt gtggaattgt gagcggataa caatttcaca    3540
cagggccctc ggacaccgag gagaatgtca agaggcgaac acacaacgtc ttggagcgcc    3600
agaggaggaa cgagctaaaa cggagctttt ttgccctgcg tgaccagatc ccggagttgg    3660
aaaacaatga aaaggccccc aaggtagtta tccttaaaaa agccacagca tacatcctgt    3720
ccgtccaagc agaggagcaa aagctcattt ctgaagagga cttgttgcgg aaacgacgag    3780
aacagttgaa acacaaactt gaacagctac ggaactcttg tgcgtaagga aaagtaagga    3840
aaacgattcc ttctaacaga aatgtcctga gcaatcacct atgaactgtc gactcgagca    3900
tagcattttt atccataaga ttagcggatc taacctttac aattgtgagc gctcacaatt    3960
atgatagatt caattgtgag cggataacaa tttcaca                            3997
```

```
<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
atcggtacca tgagtgtcaa cttagcttc                                        29

<210> SEQ ID NO 29
<211> LENGTH: 43
<212> TYPE: DNA
<213> ORGANISM: Artificial Sequence
<220> FEATURE:
<223> OTHER INFORMATION: Primer

<400> SEQUENCE: 29
attggatcct ttctcctctt taactagcct tcggaggtgg cga                        43

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cggatatcat gtcccctata cta                                              23

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
gcgcggccgc ttagccgata aattgtcc                                         28

<210> SEQ ID NO 32
<211> LENGTH: 2160
<212> TYPE: DNA
<213> ORGANISM: Arabidopsis thaliana
<220> FEATURE:
<221> NAME/KEY: CDS
<222> LOCATION: (248)..(469)
<220> FEATURE:
<221> NAME/KEY: CDS
<222> LOCATION: (653)..(769)
<220> FEATURE:
<221> NAME/KEY: CDS
<222> LOCATION: (852)..(947)
<220> FEATURE:
<221> NAME/KEY: CDS
<222> LOCATION: (1034)..(1126)
<220> FEATURE:
<221> NAME/KEY: CDS
<222> LOCATION: (1213)..(1344)
<220> FEATURE:
<221> NAME/KEY: CDS
<222> LOCATION: (1419)..(1523)
<220> FEATURE:
<221> NAME/KEY: CDS
<222> LOCATION: (1612)..(1662)
<220> FEATURE:
<221> NAME/KEY: CDS
<222> LOCATION: (1743)..(1913)
```

-continued

```
<400> SEQUENCE: 32
gaattcccca cgtcaacgtg actgtgcatt ccacgtggcg gatgtgggcc ctatagttgg      60
accatgactc ggacggatgt tgaaattcat tgtcgttgcc aattgcgttt gtctcactga     120
aactgtgaaa attttatctc ttttatagat aaagaatctt gctttttca gttttcagta     180 tgaagaagaa ttgaagagag tgtccgagga aggagacctt tggtttcagt ttgtgagtct     240 tgttgta atg gct tta tca atg gag ttt ggg ttt tca att ggg tca tgc       289
        Met Ala Leu Ser Met Glu Phe Gly Phe Ser Ile Gly Ser Cys
          1               5                  10 ttc aag gca cca aac cca cct gtt cta atc tct gca agc cct aat aag       337
Phe Lys Ala Pro Asn Pro Pro Val Leu Ile Ser Ala Ser Pro Asn Lys
 15                  20                  25                  30 atc aat ttc acg ttg aga agg aga aag aaa aga ttc tta ctt aga gtc       385
Ile Asn Phe Thr Leu Arg Arg Arg Lys Lys Arg Phe Leu Leu Arg Val
                 35                  40                  45 tct gct gtg tcg tat aag gaa ttc gca gag tct gct tta gaa gaa acc       433
Ser Ala Val Ser Tyr Lys Glu Phe Ala Glu Ser Ala Leu Glu Glu Thr
 50                  55                  60 agg aaa agg atc gtt ctt gaa cct tca cat ctc cag gtatatgcaa            479
Arg Lys Arg Ile Val Leu Glu Pro Ser His Leu Gln
 65                  70 ttacatttcg ttagtgtagt gggaggatta tatttctcat tgtttcttgc tgtgaatttt     539
gggtaaattg atttgagttg tcattaggaa ccaaacaaat aactttactg ttatagactg     599
cttatataag taaagttca gattttgttt ttctaatcac gaaactgttt cag gaa         655
                                                         Glu
                                                          75 aag tat agt agc atg aca gga cta gat ggt aag acc gaa ctt caa atg       703
Lys Tyr Ser Ser Met Thr Gly Leu Asp Gly Lys Thr Glu Leu Gln Met
                 80                  85                  90 ctt gct ttt aaa tct tca aag att aga ctc ttg agg agt atg gca ata       751
Leu Ala Phe Lys Ser Ser Lys Ile Arg Leu Leu Arg Ser Met Ala Ile
                 95                 100                 105 gag aat gag aca atg cag gtttaacttc agcagtacaa actgattgct               799
Glu Asn Glu Thr Met Gln
            110 ttagtcccat ttccttactt tcaattgatt gattgtttgt atcttcgctt ag gtc ttt      857
                                                         Val Phe
                                                             115 gac ttt gcg ggt ttc atg gag cct gag tat gat act ccc ata ttc tgt       905
Asp Phe Ala Gly Phe Met Glu Pro Glu Tyr Asp Thr Pro Ile Phe Cys
            120                 125                 130 gct aac ttt ttc aca tct acc aac gtt aac ata gtt gta ttg               947
Ala Asn Phe Phe Thr Ser Thr Asn Val Asn Ile Val Val Leu
            135                 140                 145 taagttatct tctagttatg ctggagttat caggtctgta ttgtccaaac tgatgttcaa    1007
tattttactg tatgttcttc tttagg gac ctt aat cct ttg cat cag ttg act     1060
                            Asp Leu Asn Pro Leu His Gln Leu Thr
                                                         150 gac cag acg gat tac caa gac aag tat tat aac aag ata atg tcc ata      1108
Asp Gln Thr Asp Tyr Gln Asp Lys Tyr Tyr Asn Lys Ile Met Ser Ile
155                 160                 165                 170 tat cac aaa tat gct gag gtgaccacaa gaatacacca aattactcaa             1156
Tyr His Lys Tyr Ala Glu
                175 ttgcaagtaa acctaatgct gaggtgtaaa tgactgatct tgagatttat ttgcag act    1215
                                                              Thr
```

```
ttc cca tgg gga ggg aaa ttg act ggt gaa tcc ata aag ttt ttc tcg         1263
Phe Pro Trp Gly Gly Lys Leu Thr Gly Glu Ser Ile Lys Phe Phe Ser
            180                 185                 190 cct ttg gtg atg tgg act agg ttt tcg tct agc aaa gaa aaa cat aag         1311
Pro Leu Val Met Trp Thr Arg Phe Ser Ser Ser Lys Glu Lys His Lys
195                 200                 205 gct ttg ttc tct gcg ttt cta gag tac tat cag gtatatactc agcggccaaa       1364
Ala Leu Phe Ser Ala Phe Leu Glu Tyr Tyr Gln
210                 215                 220 agctaaggtt ttattggaaa ctttgactga aatctatca tcttcttcct acag gca          1421
                                                           Ala tgg ctt gag atg aca atc caa gtg agg gag gag atg gaa cca tct cat         1469
Trp Leu Glu Met Thr Ile Gln Val Arg Glu Glu Met Glu Pro Ser His
                225                 230                 235 gtg aga gcc aat tgt gaa gca caa cac aag tac ctg aca tgg cga gca         1517
Val Arg Ala Asn Cys Glu Ala Gln His Lys Tyr Leu Thr Trp Arg Ala
        240                 245                 250 caa aag gtgatttcat tcctttgt gtaatttgca tgtttgaaca gacactgtat            1573
Gln Lys
    255 ctgtattgtt acaatggata ttgatttggt gtttgcag gat cct gga cat ggt ctt      1629
                                          Asp Pro Gly His Gly Leu
                                                          260 ctt aaa aga tta gta ggt gaa gca aag gca aag gtataaaga tttgatccca        1682
Leu Lys Arg Leu Val Gly Glu Ala Lys Ala Lys
            265                 270 ttagtgtccc cattattaat tagcttgtga agatgttgaa atgatttga acaaaatcag        1742 gag ctg cta agg gat ttc ctg ttc aat ggg gtg gat gag tta ggc aca         1790
Glu Leu Leu Arg Asp Phe Leu Phe Asn Gly Val Asp Glu Leu Gly Thr
                275                 280                 285 aaa aca ttc att gat tac ttt cca gag tac caa aca gaa gat gga act         1838
Lys Thr Phe Ile Asp Tyr Phe Pro Glu Tyr Gln Thr Glu Asp Gly Thr
        290                 295                 300 gta agc gat aaa cga agt atc att ggg aag tca tat gaa act cgt cca         1886
Val Ser Asp Lys Arg Ser Ile Ile Gly Lys Ser Tyr Glu Thr Arg Pro
305                 310                 315                 320 tgg gat tta aca gga caa ttt atc ggc taacaatgat atatgtgaac               1933
Trp Asp Leu Thr Gly Gln Phe Ile Gly
                325 aagtcagatt tcagagtcat caacacaaga ggacgtgaac ttagggaagt aggaataaga       1993 aagagcagca tgaggagtct ctcaggtcta tctgcatttc aagatgattg tttgagttac       2053 catgcattgt agttttacaa gtgtagctct cagcccttca tcaaaatgag aatcctcgag       2113 tatgatgatga ttttaatgaa aatgtattcg tctctaccta atcaaca                   2160

<210> SEQ ID NO 33
<211> LENGTH: 329
<212> TYPE: PRT
<213> ORGANISM: Arabidopsis thaliana

<400> SEQUENCE: 33

Met Ala Leu Ser Met Glu Phe Gly Phe Ser Ile Gly Ser Cys Phe Lys
1               5                   10                  15

Ala Pro Asn Pro Pro Val Leu Ile Ser Ala Ser Pro Asn Lys Ile Asn
            20                  25                  30

Phe Thr Leu Arg Arg Arg Lys Lys Arg Phe Leu Leu Arg Val Ser Ala
        35                  40                  45
```

```
Val Ser Tyr Lys Glu Phe Ala Glu Ser Ala Leu Glu Thr Arg Lys
 50                  55                  60

Arg Ile Val Leu Glu Pro Ser His Leu Gln Glu Lys Tyr Ser Ser Met
 65                  70                  75                  80

Thr Gly Leu Asp Gly Lys Thr Glu Leu Gln Met Leu Ala Phe Lys Ser
                 85                  90                  95

Ser Lys Ile Arg Leu Leu Arg Ser Met Ala Ile Glu Asn Glu Thr Met
                100                 105                 110

Gln Val Phe Asp Phe Ala Gly Phe Met Glu Pro Glu Tyr Asp Thr Pro
                115                 120                 125

Ile Phe Cys Ala Asn Phe Phe Thr Ser Thr Asn Val Asn Ile Val Val
    130                 135                 140

Leu Asp Leu Asn Pro Leu His Gln Leu Thr Asp Gln Thr Asp Tyr Gln
145                 150                 155                 160

Asp Lys Tyr Tyr Asn Lys Ile Met Ser Ile Tyr His Lys Tyr Ala Glu
                165                 170                 175

Thr Phe Pro Trp Gly Gly Lys Leu Thr Gly Glu Ser Ile Lys Phe Phe
                180                 185                 190

Ser Pro Leu Val Met Trp Thr Arg Phe Ser Ser Lys Glu Lys His
            195                 200                 205

Lys Ala Leu Phe Ser Ala Phe Leu Glu Tyr Tyr Gln Ala Trp Leu Glu
    210                 215                 220

Met Thr Ile Gln Val Arg Glu Glu Met Glu Pro Ser His Val Arg Ala
225                 230                 235                 240

Asn Cys Glu Ala Gln His Lys Tyr Leu Thr Trp Arg Ala Gln Lys Asp
                245                 250                 255

Pro Gly His Gly Leu Leu Lys Arg Leu Val Gly Glu Ala Lys Ala Lys
                260                 265                 270

Glu Leu Leu Arg Asp Phe Leu Phe Asn Gly Val Asp Glu Leu Gly Thr
            275                 280                 285

Lys Thr Phe Ile Asp Tyr Phe Pro Glu Tyr Gln Thr Glu Asp Gly Thr
    290                 295                 300

Val Ser Asp Lys Arg Ser Ile Ile Gly Lys Ser Tyr Glu Thr Arg Pro
305                 310                 315                 320

Trp Asp Leu Thr Gly Gln Phe Ile Gly
                325
```

<210> SEQ ID NO 34
<211> LENGTH: 329
<212> TYPE: PRT
<213> ORGANISM: Arapidopsis thaliana

<400> SEQUENCE: 34

```
Met Ala Leu Ser Met Glu Phe Gly Phe Ser Ile Gly Ser Cys Phe Lys
 1                   5                  10                  15

Ala Pro Asn Pro Val Leu Ile Ser Ala Pro Asn Lys Ile Asn
                 20                  25                  30

Phe Thr Leu Arg Arg Lys Lys Arg Phe Leu Leu Arg Val Ser Ala
             35                  40                  45

Val Ser Tyr Lys Glu Phe Ala Glu Ser Ala Leu Glu Thr Arg Lys
 50                  55                  60

Arg Ile Val Leu Glu Pro Ser His Leu Gln Glu Lys Tyr Ser Ser Met
 65                  70                  75                  80

Thr Gly Leu Asp Gly Lys Thr Glu Leu Gln Met Leu Ala Phe Lys Ser
                 85                  90                  95
```

```
Ser Lys Ile Arg Leu Leu Arg Ser Met Ala Ile Glu Asn Glu Thr Met
            100                 105                 110
Gln Val Phe Asp Phe Ala Gly Phe Met Glu Pro Glu Tyr Asp Thr Pro
        115                 120                 125
Ile Phe Cys Ala Asn Phe Phe Thr Ser Thr Asn Val Asn Ile Val Val
    130                 135                 140
Leu Asp Leu Asn Pro Leu His Gln Leu Thr Asp Gln Thr Asp Tyr Gln
145                 150                 155                 160
Asp Lys Tyr Tyr Asn Lys Ile Met Ser Ile Tyr His Lys Tyr Ala Glu
                165                 170                 175
Thr Phe Pro Trp Gly Gly Lys Leu Thr Gly Glu Ser Ile Lys Phe Phe
            180                 185                 190
Ser Pro Leu Val Met Trp Thr Arg Phe Ser Ser Lys Glu Lys His
        195                 200                 205
Lys Ala Leu Phe Ser Ala Phe Leu Glu Tyr Tyr Gln Ala Trp Leu Glu
    210                 215                 220
Met Thr Ile Gln Val Arg Glu Glu Met Glu Pro Ser His Val Arg Ala
225                 230                 235                 240
Asn Cys Glu Ala Gln His Lys Tyr Leu Thr Trp Arg Ala Gln Lys Asp
                245                 250                 255
Pro Gly His Gly Leu Leu Lys Arg Leu Val Gly Glu Ala Lys Ala Lys
            260                 265                 270
Glu Leu Leu Arg Asp Phe Leu Phe Asn Gly Val Asp Glu Leu Gly Thr
        275                 280                 285
Lys Thr Phe Ile Asp Tyr Phe Pro Glu Tyr Gln Thr Glu Asp Gly Thr
    290                 295                 300
Val Ser Asp Lys Arg Ser Ile Ile Gly Lys Ser Tyr Glu Thr Arg Pro
305                 310                 315                 320
Trp Asp Leu Thr Gly Gln Phe Ile Gly
                325
```

<210> SEQ ID NO 35
<211> LENGTH: 236
<212> TYPE: PRT
<213> ORGANISM: Synechococcus sp.

<400> SEQUENCE: 35

```
Met Phe Asp Ser Phe Leu Asn Glu Leu His Ser Asp Ile Thr Lys Arg
1               5                   10                  15
Gly Gly Ser Pro Leu Pro Leu Pro Glu Gly Leu Glu Glu Cys Arg Ser
            20                  25                  30
Ser Lys Ser Ser Ser Val Ile Gln Ser Trp Leu Trp Asp Val Pro Gly
        35                  40                  45
Phe Arg Arg Trp Arg Val Thr Arg Leu Asp Ala Gly Asp Ser Leu Gln
    50                  55                  60
Val Phe Asn Ser Val Ala Tyr Pro Asp Tyr Asn Tyr Asp His Pro Leu
65                  70                  75                  80
Met Gly Val Asp Leu Leu Trp Phe Gly Ala Arg Gln Lys Leu Val Ala
                85                  90                  95
Val Leu Asp Phe Gln Pro Leu Val Gln Asp Lys Asp Tyr Leu Asp Arg
            100                 105                 110
Tyr Phe Ser Gly Leu Lys Glu Leu Asn Gln Arg Phe Pro Asp Leu Asn
        115                 120                 125
Gly Glu Glu Thr Met Arg Ser Phe Asp Pro Asn Gln Tyr Phe Ser Ser
    130                 135                 140
```

```
Trp Leu Leu Phe Cys Arg Gly Gly Ala Glu Gln Ala Asp Leu Ser Leu
145                 150                 155                 160

Pro Lys Ala Phe Ser Ala Phe Leu Lys Ala Tyr Trp Asp Leu His Asp
                165                 170                 175

Asn Ala Lys Ser Ile Pro Ser Thr Ile Pro Pro Glu Glu Val Lys Asn
            180                 185                 190

Leu Gln Asp Lys Tyr Asp Ile Tyr Ser Ala Glu Arg Asp Pro Ala His
        195                 200                 205

Gly Leu Phe Thr Ser His Phe Gly Lys Asp Trp Ser Asn Arg Phe Leu
    210                 215                 220

His Glu Phe Leu Phe Pro Ala Ser Ser Ser His Lys
225                 230                 235
```

<210> SEQ ID NO 36
<211> LENGTH: 257
<212> TYPE: PRT
<213> ORGANISM: Synechococcus sp.

<400> SEQUENCE: 36

```
Met Thr Asn Gln Arg Phe Lys Ser Thr Asp Pro Val Asn Ile Glu Gly
1               5                   10                  15

Trp Ser Trp Gln Pro Phe Leu Glu Asp Ala Ile Lys Arg Leu Glu Gly
            20                  25                  30

Leu Asn Val Glu Pro Tyr Pro Val Pro Asp Arg Phe Leu Gln Arg Glu
        35                  40                  45

Asp Gln Thr Gly Ser Lys Ser Lys Ser Ile Pro Val Thr Thr Ala Thr
    50                  55                  60

Trp Ala Cys Lys Thr Glu Lys Phe Arg Gln Val Arg Ala Ala Cys Val
65                  70                  75                  80

Ser Ala Gly Ser Ala Ala Ser Val Leu Asn Phe Val Ile Asn Pro Lys
                85                  90                  95

Ser Thr Tyr Gly Leu Pro Phe Phe Gly Gly Asp Leu Val Thr Phe Pro
            100                 105                 110

Ala Gly His Leu Leu Ala Leu Asp Leu Gln Pro Ala Ile Lys Thr Asp
        115                 120                 125

Glu Val His Thr Thr His Val Trp Asp Arg Leu Ile Pro Ile Phe Glu
    130                 135                 140

Arg Trp Arg Asp Gln Leu Pro Tyr Gly Gly Pro Ile Pro Glu Glu Ala
145                 150                 155                 160

Gln Pro Phe Phe Ser Pro Gly Phe Leu Trp Thr Arg Leu Pro Leu Gly
                165                 170                 175

Glu Glu Gly Asp Glu Leu Ile Gln Ser Ile Val Arg Pro Ala Phe Asn
            180                 185                 190

Asp Tyr Leu Asp Leu Tyr Leu Glu Leu Ala Ala Ser Ala Glu Arg Val
        195                 200                 205

Thr Asp Glu Arg Ser Glu Val Leu Leu Gln Gly Gln Arg Lys Tyr Thr
    210                 215                 220

Asp Tyr Arg Ala Glu Lys Asp Pro Ala Arg Gly Met Leu Thr Arg Phe
225                 230                 235                 240

His Gly Ser Glu Trp Thr Glu Ala Tyr Ile His Thr Val Leu Phe Asp
                245                 250                 255

Leu
```

<210> SEQ ID NO 37
<211> LENGTH: 241
<212> TYPE: PRT
<213> ORGANISM: Prochlorococcus marinus

<400> SEQUENCE: 37

Met Asn Lys Leu Met Leu Gln Asp Leu His Asn Asn Leu Lys Arg Arg
1               5                   10                  15

Ile Ile Ser His Gly Gly Lys Pro Ile Glu Val Glu Asn Gly Met Ser
            20                  25                  30

Glu Arg Phe Ser His Lys Gln Asp Thr Val Ile Lys Ser Trp Leu Trp
        35                  40                  45

Asp Val Pro Gly Phe Arg Arg Trp Arg Val Thr Arg Met Asp Ala Gly
    50                  55                  60

Asp Lys Leu Gln Val Leu Asn Ser Val Ala Tyr Pro Ala Tyr Thr Asn
65                  70                  75                  80

Asp Lys Pro Ile Leu Gly Ile Asp Ile Leu Trp Phe Gly Leu Lys Arg
                85                  90                  95

Lys Leu Val Ala Val Leu Asp Phe Gln Pro Leu Val Gln Glu Glu Arg
            100                 105                 110

Tyr Phe Cys Arg Tyr Tyr Lys Asp Leu Gln Ile Leu Lys Asn Arg Phe
        115                 120                 125

Val Asp Phe Asn Ser Gln Lys Thr Met Lys Ile Tyr Asp Ser Asn Lys
    130                 135                 140

Tyr Phe Ser Pro Trp Val Leu Leu Tyr Asn Gly Ser Phe Asp Asp Leu
145                 150                 155                 160

Gln Cys Ser Leu Ala Lys Ile Leu Asp Glu Phe Leu His Ala Tyr Trp
                165                 170                 175

Gln Val Asp Asn Asn Ser Arg Glu Tyr Ile Lys Ile Ile Pro Ser
            180                 185                 190

Lys Val Glu Gln Leu His Ile Asn Tyr Asp Ile Tyr Ser Ala Glu Arg
            195                 200                 205

Asp Pro Ala His Gly Leu Phe Lys Ser Tyr Phe Gly Gln Thr Trp Ala
    210                 215                 220

Asp Gln Phe Val Arg Glu Phe Leu Phe Pro His Ser His Leu Thr Ala
225                 230                 235                 240

Asp

<210> SEQ ID NO 38
<211> LENGTH: 257
<212> TYPE: PRT
<213> ORGANISM: PROCHLOROCOCCUS MARINUS

<400> SEQUENCE: 38

Met Ile Ile Lys Arg Asp Asn Ser Leu Ser Lys Ile Asp Leu Arg Asp
1               5                   10                  15

Trp Ile Trp Thr Pro Phe Phe Asn Asp Leu Val Asp Lys Leu Ser Val
            20                  25                  30

Phe Glu Ile Glu Pro Tyr Pro Val Ser His Asp Phe Leu Ser Lys Glu
        35                  40                  45

Ser Ile Thr Gly Ser Arg Arg Asn Pro Val His Val Thr Thr Leu Thr
    50                  55                  60

Trp Ala Ala Lys Phe Glu Lys Ile Lys Gln Val Arg Leu Ala Cys Ile
65                  70                  75                  80

Lys Gly Gly Glu Ser Leu Ser Val Phe Asn Leu Leu Ile His Pro Leu
                85                  90                  95

-continued

```
Asn Asp Tyr Asp Leu Pro Phe Gly Ala Asp Phe Val Thr Leu Pro
            100                 105                 110

Asn Gly His Leu Leu Ala Leu Asp Leu Gln Pro Ala Leu Lys Leu Asp
        115                 120                 125

Asn Ile His Thr Glu Asn Val Trp Pro Arg Leu Ile Pro Leu His Asp
    130                 135                 140

His Trp Gln Ser Leu Leu Pro Ser Gly Gly Glu Ile Pro Lys Glu Ala
145                 150                 155                 160

Glu Pro Tyr Phe Ser Pro Gly Phe Leu Trp Ser Arg Leu Pro Leu Ser
                165                 170                 175

Lys Glu Ser Asp Asn Ile Ile Ser Glu Ile Leu Arg Pro Ala Phe Gly
            180                 185                 190

Glu Tyr Leu Ser Leu Tyr Ile Glu Leu Leu His Ile Ala Lys Pro Leu
        195                 200                 205

Lys Lys Glu Arg Ala Leu Lys Ile Leu Glu Gly Gln Lys Ala Tyr Ile
    210                 215                 220

Asn Tyr Arg Ser Thr Lys Asp Pro Ala Arg Ala Met Leu Cys Arg Phe
225                 230                 235                 240

Tyr Gly Lys Glu Trp Thr Glu Asp Tyr Ile His Lys Val Leu Phe Asn
                245                 250                 255

Ile

<210> SEQ ID NO 39
<211> LENGTH: 248
<212> TYPE: PRT
<213> ORGANISM: Synechocystis sp.

<400> SEQUENCE: 39

Met Ala Val Thr Asp Leu Ser Leu Thr Asn Ser Ser Leu Met Pro Thr
1               5                   10                  15

Leu Asn Pro Met Ile Gln Gln Leu Ala Leu Ala Ile Ala Ala Ser Trp
            20                  25                  30

Gln Ser Leu Pro Leu Lys Pro Tyr Gln Leu Pro Glu Asp Leu Gly Tyr
        35                  40                  45

Val Glu Gly Arg Leu Glu Gly Glu Lys Leu Val Ile Glu Asn Arg Cys
    50                  55                  60

Tyr Gln Thr Pro Gln Phe Arg Lys Met His Leu Glu Leu Ala Lys Val
65                  70                  75                  80

Gly Lys Gly Leu Asp Ile Leu His Cys Val Met Phe Pro Glu Pro Leu
                85                  90                  95

Tyr Gly Leu Pro Leu Phe Gly Cys Asp Ile Val Ala Gly Pro Gly Gly
            100                 105                 110

Val Ser Ala Ala Ile Ala Asp Leu Ser Pro Thr Gln Ser Asp Arg Gln
        115                 120                 125

Leu Pro Ala Ala Tyr Gln Lys Ser Leu Ala Glu Leu Gly Gln Pro Glu
    130                 135                 140

Phe Glu Gln Gln Arg Glu Leu Pro Pro Trp Gly Glu Ile Phe Ser Glu
145                 150                 155                 160

Tyr Cys Leu Phe Ile Arg Pro Ser Asn Val Thr Glu Glu Arg Phe
                165                 170                 175

Val Gln Arg Val Val Asp Phe Leu Gln Ile His Cys His Gln Ser Ile
            180                 185                 190

Val Ala Glu Pro Leu Ser Glu Ala Gln Thr Leu Glu His Arg Gln Gly
        195                 200                 205
```

```
Gln Ile His Tyr Cys Gln Gln Gln Lys Asn Asp Lys Thr Arg Arg
    210                 215                 220

Val Leu Glu Lys Ala Phe Gly Glu Ala Trp Ala Glu Arg Tyr Met Ser
225                 230                 235                 240

Gln Val Leu Phe Asp Val Ile Gln
                245

<210> SEQ ID NO 40
<211> LENGTH: 490
<212> TYPE: PRT
<213> ORGANISM: Anabaena sp.

<400> SEQUENCE: 40

Met Ser Leu Thr Ser Ile Pro Ser Leu Arg Glu Gln Gln His Pro Leu
1               5                   10                  15

Ile Arg Gln Leu Ala Asp Cys Ile Glu Glu Val Trp His Gln His Leu
                20                  25                  30

Asp Leu Ser Pro Tyr His Leu Pro Ala Glu Leu Gly Tyr Val Glu Gly
            35                  40                  45

Arg Leu Glu Gly Glu Lys Leu Thr Ile Glu Asn Arg Cys Tyr Gln Thr
    50                  55                  60

Pro Gln Phe Arg Lys Met His Leu Glu Leu Ala Lys Val Gly Asn Met
65                  70                  75                  80

Leu Asp Ile Leu His Cys Val Met Phe Pro Arg Pro Glu Tyr Asp Leu
                85                  90                  95

Pro Met Phe Gly Cys Asp Leu Val Gly Gly Arg Gly Gln Ile Ser Ala
            100                 105                 110

Ala Ile Ala Asp Leu Ser Pro Val His Leu Asp Arg Thr Leu Pro Glu
    115                 120                 125

Ser Tyr Asn Ser Ala Leu Thr Ser Leu Asn Thr Leu Asn Phe Ser Gln
130                 135                 140

Pro Arg Glu Leu Pro Glu Trp Gly Asn Ile Phe Ser Asp Phe Cys Ile
145                 150                 155                 160

Phe Val Arg Pro Ser Ser Pro Glu Glu Ala Met Phe Leu Gly Arg
                165                 170                 175

Val Arg Glu Phe Leu Gln Val His Cys Gln Gly Ala Ile Ala Ala Ser
            180                 185                 190

Pro Val Ser Ala Glu Gln Lys Gln Gln Ile Leu Ala Gly Gln His Asn
    195                 200                 205

Tyr Cys Ser Lys Gln Gln Asn Asp Lys Thr Arg Arg Val Leu Glu
    210                 215                 220

Lys Ala Phe Gly Val Asp Trp Ala Glu Asn Tyr Met Thr Thr Val Leu
225                 230                 235                 240

Phe Asp Leu Pro Glu Met Ser Leu Thr Ser Ile Pro Ser Leu Arg Glu
                245                 250                 255

Gln Gln His Pro Leu Ile Arg Gln Leu Ala Asp Cys Ile Glu Glu Val
            260                 265                 270

Trp His Gln His Leu Asp Leu Ser Pro Tyr His Leu Pro Ala Glu Leu
    275                 280                 285

Gly Tyr Val Glu Gly Arg Leu Glu Gly Glu Lys Leu Thr Ile Glu Asn
290                 295                 300

Arg Cys Tyr Gln Thr Pro Gln Phe Arg Lys Met His Leu Glu Leu Ala
305                 310                 315                 320

Lys Val Gly Asn Met Leu Asp Ile Leu His Cys Val Met Phe Pro Arg
                325                 330                 335
```

-continued

Pro Glu Tyr Asp Leu Pro Met Phe Gly Cys Asp Leu Val Gly Gly Arg
                340                 345                 350

Gly Gln Ile Ser Ala Ala Ile Ala Asp Leu Ser Pro Val His Leu Asp
            355                 360                 365

Arg Thr Leu Pro Glu Ser Tyr Asn Ser Ala Leu Thr Ser Leu Asn Thr
        370                 375                 380

Leu Asn Phe Ser Gln Pro Arg Glu Leu Pro Glu Trp Gly Asn Ile Phe
385                 390                 395                 400

Ser Asp Phe Cys Ile Phe Val Arg Pro Ser Pro Glu Glu Glu Ala
                405                 410                 415

Met Phe Leu Gly Arg Val Arg Glu Phe Leu Gln Val His Cys Gln Gly
                420                 425                 430

Ala Ile Ala Ala Ser Pro Val Ser Ala Glu Gln Lys Gln Gln Ile Leu
            435                 440                 445

Ala Gly Gln His Asn Tyr Cys Ser Lys Gln Gln Gln Asn Asp Lys Thr
        450                 455                 460

Arg Arg Val Leu Glu Lys Ala Phe Gly Val Asp Trp Ala Glu Asn Tyr
465                 470                 475                 480

Met Thr Thr Val Leu Phe Asp Leu Pro Glu
                485                 490

<210> SEQ ID NO 41
<211> LENGTH: 245
<212> TYPE: PRT
<213> ORGANISM: Nostoc punctiforme

<400> SEQUENCE: 41

Met Ser Phe Thr Ser Met Pro Ser Leu Arg Glu Gln Gln His Pro Leu
1               5                   10                  15

Ile Arg Gln Leu Ala Asp Cys Ile Glu Ala Ala Trp His Gln His Leu
            20                  25                  30

Asp Leu Ser Pro Tyr His Leu Pro Asp Glu Leu Gly Tyr Val Glu Gly
        35                  40                  45

Arg Leu Glu Gly Glu Lys Leu Thr Ile Glu Asn Arg Cys Tyr Gln Thr
50                  55                  60

Pro Gln Phe Arg Lys Met His Leu Glu Leu Ala Asn Ile Gly Asn Met
65                  70                  75                  80

Leu Asp Ile Leu His Cys Val Met Phe Pro Arg Pro Gln Tyr Asn Leu
                85                  90                  95

Pro Met Phe Gly Cys Asp Leu Val Gly Gly Arg Gly Gln Ile Ser Ala
            100                 105                 110

Ala Ile Ala Asp Leu Ser Pro Ile Gln Leu Glu Arg Thr Leu Pro Glu
        115                 120                 125

Ser Tyr Thr Thr Ala Leu Ala Gln Leu Pro Val Leu Asn Phe Ser Gln
130                 135                 140

Pro Arg Glu Leu Pro Glu Trp Gly Asn Ile Phe Ser Asp Phe Cys Ile
145                 150                 155                 160

Phe Val Arg Pro Gly Ser Pro Glu Glu Ala Met Phe Leu Ser Arg
                165                 170                 175

Val Arg Glu Phe Leu Asp Ile His Cys Met Gln Ala Ile Ala Ser His
            180                 185                 190

Pro Val Ser Val Glu Gln Val Thr Gln Asn Leu Ala Gly Gln His Asn
        195                 200                 205

Tyr Cys Thr Lys Gln Gln Gln Asn Asp Lys Thr Arg Arg Val Leu Glu
210                 215                 220

```
Lys Ala Phe Gly Pro Val Trp Ala Glu Asn Tyr Met Thr Thr Val Leu
225                 230                 235                 240

Phe Asp Leu Pro Thr
            245

<210> SEQ ID NO 42
<211> LENGTH: 248
<212> TYPE: PRT
<213> ORGANISM: Synechocystis sp.

<400> SEQUENCE: 42

Met Ala Val Thr Asp Leu Ser Leu Thr Asn Ser Ser Leu Met Pro Thr
1               5                   10                  15

Leu Asn Pro Met Ile Gln Gln Leu Ala Leu Ala Ile Ala Ala Ser Trp
            20                  25                  30

Gln Ser Leu Pro Leu Lys Pro Tyr Gln Leu Pro Glu Asp Leu Gly Tyr
        35                  40                  45

Val Glu Gly Arg Leu Glu Gly Glu Lys Leu Val Ile Glu Asn Arg Cys
50                  55                  60

Tyr Gln Thr Pro Gln Phe Arg Lys Met His Leu Glu Leu Ala Lys Val
65                  70                  75                  80

Gly Lys Gly Leu Asp Ile Leu His Cys Val Met Phe Pro Glu Pro Leu
                85                  90                  95

Tyr Gly Leu Pro Leu Phe Gly Cys Asp Ile Val Ala Gly Pro Gly Gly
            100                 105                 110

Val Ser Ala Ala Ile Ala Asp Leu Ser Pro Thr Gln Ser Asp Arg Gln
        115                 120                 125

Leu Pro Ala Ala Tyr Gln Lys Ser Leu Ala Glu Leu Gly Gln Pro Glu
130                 135                 140

Phe Glu Gln Gln Arg Glu Leu Pro Pro Trp Gly Glu Ile Phe Ser Glu
145                 150                 155                 160

Tyr Cys Leu Phe Ile Arg Pro Ser Asn Val Thr Glu Glu Glu Arg Phe
                165                 170                 175

Val Gln Arg Val Val Asp Phe Leu Gln Ile His Cys His Gln Ser Ile
            180                 185                 190

Val Ala Glu Pro Leu Ser Glu Ala Gln Thr Leu Glu His Arg Gln Gly
        195                 200                 205

Gln Ile His Tyr Cys Gln Gln Gln Lys Asn Asp Lys Thr Arg Arg
210                 215                 220

Val Leu Glu Lys Ala Phe Gly Glu Ala Trp Ala Glu Arg Tyr Met Ser
225                 230                 235                 240

Gln Val Leu Phe Asp Val Ile Gln
            245

<210> SEQ ID NO 43
<211> LENGTH: 247
<212> TYPE: PRT
<213> ORGANISM: Synechocystis sp.

<400> SEQUENCE: 43

Met Gln Ser Pro Pro Ser Glu Ser Ser Thr Val Ala Pro Leu Ile
1               5                   10                  15

Pro Ser Leu Ala Glu Thr Ile Arg Gly Ala Trp Ile Gly Leu Pro Glu
            20                  25                  30

Leu Lys Pro Leu Asp Ala Asp Ser Asp Phe Ser Ser Ile Glu Gly Gln
        35                  40                  45
```

-continued

Leu Glu Gly Asp Asp Leu Leu Ile Arg Asn Glu Leu Leu Cys Cys Arg
    50                  55                  60

Val Gly Arg Lys Ile His Leu Glu Leu Ala Arg Leu Gly Arg Gly Leu
65                  70                  75                  80

Gln Ile Leu His Cys Val Trp Phe Pro Asp Pro Arg Phe Asp Leu Pro
                85                  90                  95

Ile Phe Gly Ala Asp Ile Val Ala Gly Pro Ala Gly Val Ser Ala Ala
                100                 105                 110

Ile Val Asp Leu Ser Pro Val Ser Gly Thr Leu Pro Ser Gly Ile Glu
            115                 120                 125

Thr Ala Leu Ala Gly Thr Pro Ser Pro Ala Phe Arg Gln Val Arg Asp
    130                 135                 140

Leu Pro Gly Trp Gly Thr Ile Phe Ser Pro His Val Cys Phe Ile Arg
145                 150                 155                 160

Pro Asp Gly Ala Glu Glu Val Leu Phe Arg Ser Arg Val Glu Glu
                165                 170                 175

Val Leu Thr Ile Leu Arg Thr Ala Val Leu Gln Thr Ala Cys Glu Pro
            180                 185                 190

Ala Thr Ala Ala Ser Thr Ile Arg Arg Tyr Glu Gly Gln Leu Ser Tyr
            195                 200                 205

Cys Leu Gln Gln Lys Arg Asn Asp Lys Thr Arg Arg Val Leu Glu Lys
210                 215                 220

Ala Phe Asp Ala Ser Trp Ala Asp Arg Tyr Ile Glu Glu Leu Leu Phe
225                 230                 235                 240

Asp Asp Pro Leu Pro Pro Gly
                245

<210> SEQ ID NO 44
<211> LENGTH: 243
<212> TYPE: PRT
<213> ORGANISM: Prochlorococcus marinus

<400> SEQUENCE: 44

Leu Asn Leu Leu Ser Lys Ser Leu Thr Lys Thr Lys Leu Ile Asp Pro
1               5                   10                  15

Leu Ile Leu Thr Leu Leu Gln Asn Ile Lys Val Gln Arg Ser Lys Leu
            20                  25                  30

Asn Asp Leu Asn Cys Ile Glu Val Asp Pro Lys Leu Ser Asn Ile Ile
        35                  40                  45

Ser Asn Glu Glu Gly Lys Glu Leu Tyr Ile Glu Asn Glu Phe Tyr Lys
    50                  55                  60

Ala Lys Gly Phe Arg Lys Leu His Ile Glu Val Ala Glu Phe Ser Lys
65                  70                  75                  80

Ser Leu Lys Ile Leu His Cys Val Phe Phe Pro Asp Pro Lys Tyr Asp
                85                  90                  95

Ile Pro Ile Phe Gly Met Asp Leu Val Lys Val Asn Glu Leu Val Ser
                100                 105                 110

Ala Ala Ile Val Asp Leu Ser Pro Ser Ser Lys Asn Gln Asn Leu Lys
            115                 120                 125

Tyr Asp His Leu Leu Ser His Ile Asp Lys Ser Val Phe Lys Ser Lys
    130                 135                 140

Arg Glu Ile Pro Ile Trp Gly Asn Ile Phe Ser Lys Asn Val Phe Phe
145                 150                 155                 160

Ala Ser Leu Lys Asn Glu Ser Glu Lys Asn Ala Phe Cys Lys Ile Val
                165                 170                 175

```
Asp Asn Tyr Leu Ser Val Leu Ile Gln Leu Ser Gln Ser Thr Ser Pro
            180                 185                 190

Asp Ser Asp Tyr Glu Ile Ile Glu Glu Arg Ile Asn Tyr Gln Lys Asn
            195                 200                 205

Tyr Cys Val Gln Gln Met Lys Asn Glu Lys Thr Ser Leu Val Leu Leu
            210                 215                 220

Lys Tyr Phe Asp Lys Val Trp Val Asp Glu Tyr Ile Lys Lys Val Leu
225                 230                 235                 240

Phe Asp Phe
```

<210> SEQ ID NO 45
<211> LENGTH: 236
<212> TYPE: PRT
<213> ORGANISM: Synechocystis sp.

<400> SEQUENCE: 45

```
Met Phe Asp Ser Phe Leu Asn Glu Leu His Ser Asp Ile Thr Lys Arg
1               5                   10                  15

Gly Gly Ser Pro Leu Pro Leu Pro Glu Gly Leu Glu Glu Cys Arg Ser
            20                  25                  30

Ser Lys Ser Ser Ser Val Ile Gln Ser Trp Leu Trp Asp Val Pro Gly
            35                  40                  45

Phe Arg Arg Trp Arg Val Thr Arg Leu Asp Ala Gly Asp Ser Leu Gln
    50                  55                  60

Val Phe Asn Ser Val Ala Tyr Pro Asp Tyr Asn Tyr Asp His Pro Leu
65                  70                  75                  80

Met Gly Val Asp Leu Leu Trp Phe Gly Ala Arg Gln Lys Leu Val Ala
            85                  90                  95

Val Leu Asp Phe Gln Pro Leu Val Gln Asp Lys Asp Tyr Leu Asp Arg
            100                 105                 110

Tyr Phe Ser Gly Leu Lys Glu Leu Asn Gln Arg Phe Pro Asp Leu Asn
            115                 120                 125

Gly Glu Glu Thr Met Arg Ser Phe Asp Pro Asn Gln Tyr Phe Ser Ser
        130                 135                 140

Trp Leu Leu Phe Cys Arg Gly Gly Ala Glu Gln Ala Asp Leu Ser Leu
145                 150                 155                 160

Pro Lys Ala Phe Ser Ala Phe Leu Lys Ala Tyr Trp Asp Leu His Asp
                165                 170                 175

Asn Ala Lys Ser Ile Pro Ser Thr Ile Pro Pro Glu Glu Val Lys Asn
            180                 185                 190

Leu Gln Asp Lys Tyr Asp Ile Tyr Ser Ala Glu Arg Asp Pro Ala His
            195                 200                 205

Gly Leu Phe Thr Ser His Phe Gly Lys Asp Trp Ser Asn Arg Phe Leu
        210                 215                 220

His Glu Phe Leu Phe Pro Ala Ser Ser Ser His Lys
225                 230                 235
```

<210> SEQ ID NO 46
<211> LENGTH: 235
<212> TYPE: PRT
<213> ORGANISM: Synechocystis sp.

<400> SEQUENCE: 46

```
Met Phe Asp Pro Phe Leu Glu Glu Leu Gln Thr Gly Ile Gln Ala Arg
1               5                   10                  15
```

```
Gly Gly Ile Ser Val Glu Val Pro Ala Gly Leu Glu His Asn Gln Ser
            20                  25                  30

Gln Lys Gly Ser Ser Thr Ile Gln Ser Trp Leu Trp Gln Val Pro Gly
        35                  40                  45

Phe Arg Arg Trp Arg Val Thr Arg Leu Asp Ala Gly Asp Ser Leu Gln
50                  55                  60

Val Leu Asn Ser Val Ala Tyr Pro Asp Phe Asp Leu Asp His Pro Leu
65                  70                  75                  80

Met Gly Val Asp Leu Leu Trp Phe Gly Ala Arg Gln Lys Leu Val Ala
                85                  90                  95

Val Leu Asp Phe Gln Pro Leu Val Gln Asp Lys Asp Tyr Leu Asp Arg
                100                 105                 110

His Phe Asp Gly Leu Lys Asp Leu Asn Ala Arg Phe Pro Asp Leu Asn
            115                 120                 125

Gly Glu Glu Thr Met Arg Ser Phe Asp Pro Asn Gln Tyr Phe Ser Ser
130                 135                 140

Trp Leu Leu Phe Cys Arg Gly Gly Ser Glu Glu Ala Asp Arg Ser Leu
145                 150                 155                 160

Pro Lys Ala Phe Ser Ala Phe Leu Lys Ala Tyr Trp Gly Leu His Asp
                165                 170                 175

Glu Ala Ser Lys Glu Pro Ser Ser Ile Ser Pro Gly Asp Val Glu Arg
                180                 185                 190

Leu Gln Asn Ala Tyr Asp Val Tyr Ser Ala Glu Arg Asp Pro Ala His
            195                 200                 205

Gly Leu Phe Thr Ser His Phe Gly Lys Glu Trp Ser Asp Arg Phe Leu
210                 215                 220

His Glu Phe Leu Phe Pro Ala Ser Gln Pro Ala
225                 230                 235

<210> SEQ ID NO 47
<211> LENGTH: 241
<212> TYPE: PRT
<213> ORGANISM: Prochlorococcus sp.

<400> SEQUENCE: 47

Met Asn Lys Leu Met Leu Gln Asp Leu His Asn Asn Leu Lys Arg Arg
1               5                   10                  15

Ile Ile Ser His Gly Gly Lys Pro Ile Glu Val Glu Asn Gly Met Ser
            20                  25                  30

Glu Arg Phe Ser His Lys Gln Asp Thr Val Ile Lys Ser Trp Leu Trp
        35                  40                  45

Asp Val Pro Gly Phe Arg Arg Trp Arg Val Thr Arg Met Asp Ala Gly
50                  55                  60

Asp Lys Leu Gln Val Leu Asn Ser Val Ala Tyr Pro Ala Tyr Thr Asn
65                  70                  75                  80

Asp Lys Pro Ile Leu Gly Ile Asp Ile Leu Trp Phe Gly Leu Lys Arg
                85                  90                  95

Lys Leu Val Ala Val Leu Asp Phe Gln Pro Leu Val Gln Glu Glu Arg
                100                 105                 110

Tyr Phe Cys Arg Tyr Tyr Lys Asp Leu Gln Ile Leu Lys Asn Arg Phe
            115                 120                 125

Val Asp Phe Asn Ser Gln Lys Thr Met Lys Ile Tyr Asp Ser Asn Lys
130                 135                 140

Tyr Phe Ser Pro Trp Val Leu Leu Tyr Asn Gly Ser Phe Asp Asp Leu
145                 150                 155                 160
```

```
Gln Cys Ser Leu Ala Lys Ile Leu Asp Glu Phe Leu His Ala Tyr Trp
                165                 170                 175

Gln Val Asp Asn Asn Ser Arg Glu Tyr Ile Lys Ile Ile Pro Ser
            180                 185                 190

Lys Val Glu Gln Leu His Ile Asn Tyr Asp Ile Tyr Ser Ala Glu Arg
        195                 200                 205

Asp Pro Ala His Gly Leu Phe Lys Ser Tyr Phe Gly Gln Thr Trp Ala
210                 215                 220

Asp Gln Phe Val Arg Glu Phe Leu Phe Pro His Ser His Leu Thr Ala
225                 230                 235                 240

Asp

<210> SEQ ID NO 48
<211> LENGTH: 236
<212> TYPE: PRT
<213> ORGANISM: Prochlorococcus sp.

<400> SEQUENCE: 48

Met Phe Glu Ser Leu Lys Asn Phe Val Lys Thr Asn Ile Glu Asp Leu
1               5                   10                  15

Asp Gly Lys Glu Leu Glu Ile Ser Lys Glu Phe Lys Glu His His Asn
            20                  25                  30

Lys Asp Ser Lys Tyr Ile Ile Lys Asn Trp Ile Phe Glu Ser Gln Gln
        35                  40                  45

Tyr Arg Lys Trp Arg Ile Thr Lys Leu Asp Gly Gly Asp Lys Leu Gln
50                  55                  60

Val Phe Asn Thr Val Ala Tyr Pro Asn Phe Lys Ser Glu Phe Pro Ile
65                  70                  75                  80

Leu Gly Ala Asp Ile Leu Trp Phe Gly Thr Ser Gln Lys Leu Leu Ala
                85                  90                  95

Ile Phe Asp Tyr Gln Pro Leu Ile Gln Glu Lys Lys Tyr Leu Gln Lys
            100                 105                 110

Tyr Cys Ser Ser Leu Asp Phe Ile Lys Asn Gln Tyr Ser Val Phe Asp
        115                 120                 125

Asn His Lys Met Lys Asn Ile Tyr Asp Ser Lys Lys Tyr Phe Ser Pro
130                 135                 140

Trp Val Met Ile Cys Arg Gly Asn Lys Leu Asn Leu Asp Arg Asp Leu
145                 150                 155                 160

Asn Asn Ile Phe Cys Ser Phe Val Ser Asn Tyr Leu Thr Ile Asn Lys
                165                 170                 175

Leu His Gln Asn Asn Gln Phe Leu Asp Leu Glu Gln Ile Lys Asn Asn
            180                 185                 190

Gln Ile Asp Tyr Asp Lys Tyr Ser Ala Glu Lys Asp Pro Ala Asp Lys
        195                 200                 205

Leu Phe Lys Thr Phe Phe Gly Glu Thr Trp Thr Glu Asn Phe Ile Asn
210                 215                 220

Asn Phe Leu Phe Thr Leu Asn His Asn Pro Leu Lys
225                 230                 235

<210> SEQ ID NO 49
<211> LENGTH: 280
<212> TYPE: PRT
<213> ORGANISM: Nostoc punctiforme
```

```
<400> SEQUENCE: 49

Met Leu Asn Ser Gln Ser Pro Leu Arg Asn Val Ala Leu Phe Leu Ile
 1               5                  10                  15

Asn Glu Thr Cys Met Ile Ala Ile Thr Tyr Phe His Ala Arg Val Asn
            20                  25                  30

Lys Ser Cys Ser Met Tyr Lys Pro Phe Leu Glu Phe Leu Glu Lys Glu
        35                  40                  45

Leu Phe Gln Arg Phe Asp Leu Gln Ser Arg Val Ile Pro Pro Gly Leu
    50                  55                  60

Glu Phe Lys Val Ser Asp Arg Gly Arg Asn Pro Ala Thr Ile Arg Ser
65                  70                  75                  80

Trp Cys Tyr Gln Ser Gln Glu Leu Arg Lys Ile Arg Tyr Thr Tyr Ile
                85                  90                  95

Asp Ala Gly Glu Ser Ala Gln Ile Phe Asn Ser Val Val Tyr Pro Ser
            100                 105                 110

His Asn Tyr Asp Leu Pro Leu Leu Gly Ile Asp Phe Leu Ser Phe Gly
        115                 120                 125

Lys Val Lys Asn Leu Ile Val Leu Asp Phe Gln Pro Leu Phe Gln Asp
    130                 135                 140

Glu Asp Tyr Gln Asn Lys Tyr Ile Ala Pro Leu Lys Tyr Leu His Asn
145                 150                 155                 160

Lys Tyr Pro Asp Leu Ala Gln Asn Leu Glu Met Lys Phe Tyr Asp Ala
                165                 170                 175

Asn Gln Tyr Phe Ser Lys Tyr Leu Leu Phe Ala Lys Thr Asp Ala Glu
            180                 185                 190

Thr Val Ser Thr Arg Val Phe Glu Ala Phe Gln Asp Tyr Leu Asn Leu
        195                 200                 205

Tyr Trp Gln Met Leu Ala Asp Ala Gln Ala Leu His Asp Pro Glu Asp
    210                 215                 220

Ile Gln Arg Ile Val Lys Ala Gln Lys Asp Tyr Asp Gln Tyr Ser Ala
225                 230                 235                 240

Asp Arg Asp Pro Ala Ser Gly Leu Phe Ser Ser Tyr Phe Gly His Glu
                245                 250                 255

Trp Ala Glu Arg Phe Leu His Glu Phe Leu Phe Glu Asp Ala Val Pro
            260                 265                 270

Leu Ala Val Ser Ala Ser Lys Arg
        275                 280

<210> SEQ ID NO 50
<211> LENGTH: 257
<212> TYPE: PRT
<213> ORGANISM: Synechocystis sp.

<400> SEQUENCE: 50

Met Thr Asn Gln Arg Phe Lys Thr Asp Pro Val Asn Ile Glu Gly
 1               5                  10                  15

Trp Ser Trp Gln Pro Phe Leu Glu Asp Ala Ile Lys Arg Leu Glu Gly
            20                  25                  30

Leu Asn Val Glu Pro Tyr Pro Val Pro Asp Arg Phe Leu Gln Arg Glu
        35                  40                  45

Asp Gln Thr Gly Ser Lys Ser Lys Ser Ile Pro Val Thr Thr Ala Thr
    50                  55                  60

Trp Ala Cys Lys Thr Glu Lys Phe Arg Gln Val Arg Ala Ala Cys Val
65                  70                  75                  80
```

```
Ser Ala Gly Ser Ala Ala Ser Val Leu Asn Phe Val Ile Asn Pro Lys
                85                  90                  95

Ser Thr Tyr Gly Leu Pro Phe Phe Gly Asp Leu Val Thr Phe Pro
            100                 105                 110

Ala Gly His Leu Leu Ala Leu Asp Leu Gln Pro Ala Ile Lys Thr Asp
            115                 120                 125

Glu Val His Thr Thr His Val Trp Asp Arg Leu Ile Pro Ile Phe Glu
130                 135                 140

Arg Trp Arg Asp Gln Leu Pro Tyr Gly Gly Pro Ile Pro Glu Glu Ala
145                 150                 155                 160

Gln Pro Phe Phe Ser Pro Gly Phe Leu Trp Thr Arg Leu Pro Leu Gly
                165                 170                 175

Glu Glu Gly Asp Glu Leu Ile Gln Ser Ile Val Arg Pro Ala Phe Asn
            180                 185                 190

Asp Tyr Leu Asp Leu Tyr Leu Glu Leu Ala Ala Ser Ala Glu Arg Val
        195                 200                 205

Thr Asp Glu Arg Ser Glu Val Leu Leu Gln Gly Gln Arg Lys Tyr Thr
210                 215                 220

Asp Tyr Arg Ala Glu Lys Asp Pro Ala Arg Gly Met Leu Thr Arg Phe
225                 230                 235                 240

His Gly Ser Glu Trp Thr Glu Ala Tyr Ile His Thr Val Leu Phe Asp
                245                 250                 255

Leu

<210> SEQ ID NO 51
<211> LENGTH: 262
<212> TYPE: PRT
<213> ORGANISM: Synechocystis sp.

<400> SEQUENCE: 51

Met Ser Ile Asp Leu Arg Ala Ser Ser Leu Asp Pro Val Gln Ile Pro
1               5                   10                  15

Gly Trp Arg Trp Gln Pro Phe Leu Asp Glu Ala Ser Ala Ala Leu Lys
            20                  25                  30

Pro Phe Asn Pro Ser Pro Tyr Pro Ile Ala Glu Thr Phe Leu Gln Lys
        35                  40                  45

Glu Gly Ser Thr Gly Ser Lys Ala Lys Pro Val Pro Val Thr Thr Ala
    50                  55                  60

Thr Trp Ala Cys Ser Thr Asp Lys Leu Arg Gln Val Arg Cys Ala Cys
65                  70                  75                  80

Val Glu Ala Gly Met Ala Ala Ser Val Leu Asn Phe Val Ile Asn Pro
                85                  90                  95

Ser Cys Arg Phe Asp Leu Pro Phe Phe Gly Ala Asp Leu Val Thr Leu
            100                 105                 110

Pro Asn Gly His Leu Leu Ala Leu Asp Leu Gln Pro Val Asp Lys Ala
        115                 120                 125

Asp Pro Asp His Thr Gln Pro Val Trp Glu Arg Leu Met Pro Leu Phe
    130                 135                 140

Glu Arg Trp Gln Ala Glu Leu Pro Asp Gly Gly Pro Ile Pro Glu Glu
145                 150                 155                 160

Ala Gln Pro Tyr Phe Ser Pro Ala Phe Leu Trp Thr Arg Ile Pro Leu
                165                 170                 175

Gly Glu Glu Gly Asp Glu Leu Ile Glu Arg Val Ile Arg Pro Ala Phe
            180                 185                 190
```

```
Ile Asp Tyr Leu Gln Leu Tyr Leu Asn Leu Val Ala Glu Ala Glu Pro
            195                 200                 205

Val Ser Asp Asp Arg Ala Glu Leu Leu Ser Gly Gln Lys Arg Tyr
210                 215                 220

Thr Ala Tyr Arg Ala Glu Lys Asp Pro Ala Arg Gly Met Leu Thr Arg
225                 230                 235                 240

Phe Tyr Gly Ser Glu Trp Thr Glu Ser Tyr Ile His Gly Val Leu Phe
            245                 250                 255

Asp Leu Glu Asp Ala Ala
            260

<210> SEQ ID NO 52
<211> LENGTH: 257
<212> TYPE: PRT
<213> ORGANISM: Prochlorococcus marinus

<400> SEQUENCE: 52

Met Ile Ile Lys Arg Asp Asn Ser Leu Ser Lys Ile Asp Leu Arg Asp
1               5                   10                  15

Trp Ile Trp Thr Pro Phe Phe Asn Asp Leu Val Asp Lys Leu Ser Val
            20                  25                  30

Phe Glu Ile Glu Pro Tyr Pro Val Ser His Asp Phe Leu Ser Lys Glu
        35                  40                  45

Ser Ile Thr Gly Ser Arg Arg Asn Pro Val His Val Thr Thr Leu Thr
    50                  55                  60

Trp Ala Lys Phe Glu Lys Ile Lys Gln Val Arg Leu Ala Cys Ile
65                  70                  75                  80

Lys Gly Gly Glu Ser Leu Ser Val Phe Asn Leu Leu Ile His Pro Leu
                85                  90                  95

Asn Asp Tyr Asp Leu Pro Phe Phe Gly Ala Asp Phe Val Thr Leu Pro
            100                 105                 110

Asn Gly His Leu Leu Ala Leu Asp Leu Gln Pro Ala Leu Lys Leu Asp
        115                 120                 125

Asn Ile His Thr Glu Asn Val Trp Pro Arg Leu Ile Pro Leu His Asp
    130                 135                 140

His Trp Gln Ser Leu Leu Pro Ser Gly Gly Glu Ile Pro Lys Glu Ala
145                 150                 155                 160

Glu Pro Tyr Phe Ser Pro Gly Phe Leu Trp Ser Arg Leu Pro Leu Ser
                165                 170                 175

Lys Glu Ser Asp Asn Ile Ile Ser Glu Ile Leu Arg Pro Ala Phe Gly
            180                 185                 190

Glu Tyr Leu Ser Leu Tyr Ile Glu Leu Leu His Ile Ala Lys Pro Leu
        195                 200                 205

Lys Lys Glu Arg Ala Leu Lys Ile Leu Glu Gly Gln Lys Ala Tyr Ile
    210                 215                 220

Asn Tyr Arg Ser Thr Lys Asp Pro Ala Arg Ala Met Leu Cys Arg Phe
225                 230                 235                 240

Tyr Gly Lys Glu Trp Thr Glu Asp Tyr Ile His Lys Val Leu Phe Asn
                245                 250                 255

Ile

<210> SEQ ID NO 53
<211> LENGTH: 257
<212> TYPE: PRT
<213> ORGANISM: Prochlorococcus sp.
```

```
<400> SEQUENCE: 53

Met Leu Ile Gln Asn Thr Ile Phe Tyr Ser Gln Glu Trp Arg Trp Ala
1               5                   10                  15

Lys Phe Ile Lys Phe Leu Ile Ser Gln Leu Asp Asn Tyr His Cys Val
            20                  25                  30

Glu His Lys Ile Ala Ser Asp Phe Ser Tyr Lys Glu Ser Ser Tyr Gly
        35                  40                  45

Ser Lys Lys Ser Lys Lys Asn Ile Asn Leu Phe Thr Trp Gly Ala Thr
    50                  55                  60

His Gln Lys Arg Ile Asn Phe Ala Arg Ala Val Cys Ile Asn Ser Pro
65                  70                  75                  80

Asn Tyr Ser Val Leu Asn Phe Leu Ile Ile Pro Lys Thr Ser Tyr Asn
                85                  90                  95

Ile Pro Phe Leu Gly Val Asp Phe Val Ser Leu Pro Thr Ser His Leu
            100                 105                 110

Leu Val Leu Asp Phe Gln Pro Ser Leu Lys Val Glu Asn Gln Phe Asn
        115                 120                 125

Ser Glu Leu Leu Glu Gln Ile Ile Lys Leu Lys Lys Ser Cys His Ser
130                 135                 140

Ser Leu Pro Val Ala Glu Lys Met Ser Glu Gln Val Ala Lys Phe Phe
145                 150                 155                 160

Ser Pro Gly Leu Ile Trp Ser Arg Leu Ala Lys His Gln Asp Ser Asp
                165                 170                 175

Asn Leu Ile Glu Asn Gln Leu Tyr Asp Ser Phe Lys Glu Tyr Leu Asn
            180                 185                 190

Leu Tyr Leu Lys Thr Leu Phe Glu Ser Glu Val Gly His Gly Leu
        195                 200                 205

Gln Gln Glu Leu Ile Asn Gly Gln Asn Asp Tyr Leu Asn Tyr Arg Arg
    210                 215                 220

Asp Asn Asp Pro Ala Arg Pro Met Leu Ser Ser Leu Phe Gly Lys Asp
225                 230                 235                 240

Phe Thr Glu Ser Leu Ile Asn Lys Val Leu Phe Ser Thr Asn Lys Val
                245                 250                 255

Leu

<210> SEQ ID NO 54
<211> LENGTH: 255
<212> TYPE: PRT
<213> ORGANISM: Nostoc punctiforme

<400> SEQUENCE: 54

Met Asn Ser Glu Arg Ser Asp Val Thr Leu Tyr Gln Pro Phe Leu Asp
1               5                   10                  15

Tyr Ala Ile Ala Tyr Met Arg Ser Arg Leu Asp Leu Glu Pro Tyr Pro
            20                  25                  30

Ile Pro Thr Gly Phe Glu Ser Asn Ser Ala Val Val Gly Lys Gly Lys
        35                  40                  45

Asn Gln Glu Glu Val Val Thr Thr Ser Tyr Ala Phe Gln Thr Ala Lys
    50                  55                  60

Leu Arg Gln Ile Arg Ala Ala His Val Gln Gly Gly Asn Ser Leu Gln
65                  70                  75                  80

Val Leu Asn Phe Val Ile Phe Pro His Leu Asn Tyr Asp Leu Pro Phe
                85                  90                  95
```

-continued

```
Phe Gly Ala Asp Leu Val Thr Leu Pro Gly His Leu Ile Ala Leu
            100                 105                 110

Asp Met Gln Pro Leu Phe Arg Asp Asp Ser Ala Tyr Gln Ala Lys Tyr
            115                 120                 125

Thr Glu Pro Ile Leu Pro Ile Phe His Ala His Gln Gln His Leu Ser
130                 135                 140

Trp Gly Asp Phe Pro Glu Glu Ala Gln Pro Phe Phe Ser Pro Ala
145                 150                 155                 160

Phe Leu Trp Thr Arg Pro Gln Glu Thr Ala Val Val Glu Thr Gln Val
                165                 170                 175

Phe Ala Ala Phe Lys Asp Tyr Leu Lys Ala Tyr Leu Asp Phe Val Glu
                180                 185                 190

Gln Ala Glu Ala Val Thr Asp Ser Gln Asn Leu Val Ala Ile Lys Gln
            195                 200                 205

Ala Gln Leu Arg Tyr Leu Arg Tyr Arg Ala Glu Lys Asp Pro Ala Arg
        210                 215                 220

Gly Met Phe Lys Arg Phe Tyr Gly Ala Glu Trp Thr Glu Glu Tyr Ile
225                 230                 235                 240

His Gly Phe Leu Phe Asp Leu Glu Arg Lys Leu Thr Val Val Lys
                245                 250                 255

<210> SEQ ID NO 55
<211> LENGTH: 329
<212> TYPE: PRT
<213> ORGANISM: Arapidopsis thaliana

<400> SEQUENCE: 55

Met Ala Leu Ser Met Glu Phe Gly Phe Ser Ile Gly Ser Cys Phe Lys
1               5                   10                  15

Ala Pro Asn Pro Val Leu Ile Ser Ala Ser Pro Asn Lys Ile Asn
            20                  25                  30

Phe Thr Leu Arg Arg Arg Lys Lys Arg Phe Leu Leu Arg Val Ser Ala
        35                  40                  45

Val Ser Tyr Lys Glu Phe Ala Glu Ser Ala Leu Glu Glu Thr Arg Lys
    50                  55                  60

Arg Ile Val Leu Glu Pro Ser His Leu Gln Glu Lys Tyr Ser Ser Met
65                  70                  75                  80

Thr Gly Leu Asp Gly Lys Thr Glu Leu Gln Met Leu Ala Phe Lys Ser
                85                  90                  95

Ser Lys Ile Arg Leu Leu Arg Ser Met Ala Ile Glu Asn Glu Thr Met
            100                 105                 110

Gln Val Phe Asp Phe Ala Gly Phe Met Glu Pro Glu Tyr Asp Thr Pro
            115                 120                 125

Ile Phe Cys Ala Asn Phe Phe Thr Ser Thr Asn Val Asn Ile Val Val
130                 135                 140

Leu Asp Leu Asn Pro Leu His Gln Leu Thr Asp Gln Thr Asp Tyr Gln
145                 150                 155                 160

Asp Lys Tyr Tyr Asn Lys Ile Met Ser Ile Tyr His Lys Tyr Ala Glu
                165                 170                 175

Thr Phe Pro Trp Gly Lys Leu Thr Gly Glu Ser Ile Lys Phe Phe
                180                 185                 190

Ser Pro Leu Val Met Trp Thr Arg Phe Ser Ser Lys Glu Lys His
            195                 200                 205

Lys Ala Leu Phe Ser Ala Phe Leu Glu Tyr Tyr Gln Ala Trp Leu Glu
        210                 215                 220
```

```
Met Thr Ile Gln Val Arg Glu Met Glu Pro Ser His Val Arg Ala
225                 230                 235                 240

Asn Cys Glu Ala Gln His Lys Tyr Leu Thr Trp Arg Ala Gln Lys Asp
                245                 250                 255

Pro Gly His Gly Leu Leu Lys Arg Leu Val Gly Glu Ala Lys Ala Lys
                260                 265                 270

Glu Leu Leu Arg Asp Phe Leu Phe Asn Gly Val Asp Glu Leu Gly Thr
            275                 280                 285

Lys Thr Phe Ile Asp Tyr Phe Pro Glu Tyr Gln Thr Glu Asp Gly Thr
        290                 295                 300

Val Ser Asp Lys Arg Ser Ile Ile Gly Lys Ser Tyr Glu Thr Arg Pro
305                 310                 315                 320

Trp Asp Leu Thr Gly Gln Phe Ile Gly
                325

<210> SEQ ID NO 56
<211> LENGTH: 205
<212> TYPE: PRT
<213> ORGANISM: Hordeum vulgare

<400> SEQUENCE: 56

Met Asp Phe Met Leu Gln Ser Ser Leu His Cys Lys Val Pro Asn Gly
1               5                   10                  15

Ala Ile Asp Ile Thr Ser Leu Phe Ile Asn Leu Asn Ala Ser Thr Asp
            20                  25                  30

Ala Pro His Phe Ile Met Glu Phe Ile Gln Gly Ser Pro Thr Ser Met
        35                  40                  45

Val Val Leu Leu Asp Leu Leu Pro Arg Lys Asp Leu Ala Leu His Pro
    50                  55                  60

Glu Tyr Ile Glu Lys Tyr Tyr Glu Asp Thr Glu Val Asp Lys Gln Arg
65                  70                  75                  80

Lys Ile Ile Glu Gln Leu Pro Gln Ala Arg Pro Tyr Leu Ser Pro Ser
                85                  90                  95

Leu Phe Val Arg Ser Ala Phe Ser Pro Thr Ala Val Phe Phe Thr Ile
            100                 105                 110

Asp Cys Gly Lys Gly Gly Glu Gly Thr Leu Glu Glu Ile Val His Gly
        115                 120                 125

His Leu Ala Ser Val Val Lys Gly Ile Leu Gln Ile Trp Leu Asp Thr
    130                 135                 140

Cys Ala Ser Asp Ala Ser Glu Met Glu Glu Gly Glu Arg Glu Ile Met
145                 150                 155                 160

Val Lys Arg Asp Arg Thr Val Arg Ser Lys Ser Ile Glu Val Asp Leu
                165                 170                 175

Thr Ala Asn Leu Pro Arg Met Phe Gly Pro Asp Val Ser Gly Arg Ile
            180                 185                 190

Ile Ala Glu Ile Arg Lys Ala Phe Gly Val Gln Glu Gly
        195                 200                 205

<210> SEQ ID NO 57
<211> LENGTH: 319
<212> TYPE: PRT
<213> ORGANISM: Arapidopsis thaliana

<400> SEQUENCE: 57

Met Ala Met Ile Phe Cys Asn Thr Leu Tyr Ser Ser Ser Ser Pro Ser
1               5                   10                  15
```

-continued

```
Tyr Leu Ser Pro Leu Thr Ser Lys Pro Ser Arg Phe Ser Lys Asn Leu
            20                  25              30

Arg Pro Arg Ala Gln Phe Gln Ser Met Glu Asp His Asp His Leu
            35                  40              45

Arg Arg Lys Phe Met Glu Phe Pro Tyr Val Ser Pro Thr Arg Lys Gln
    50                  55              60

Leu Met Val Asp Leu Met Ser Thr Val Glu Asn Arg Leu Gln Ser Gln
65                  70                  75                  80

Leu Leu Pro Cys Asn Leu Pro Pro Asp Val Arg Asn Phe Asn Asn Pro
                85              90                  95

Asn Gly Ser Ala Glu Ala Ser Leu His Ile Arg Ser Gly Asp Lys Ser
            100             105                 110

Ser Pro Ile Asp Phe Val Ile Gly Ser Trp Ile His Cys Lys Ile Pro
            115                 120                 125

Thr Gly Val Ser Leu Asn Ile Thr Ser Ile Ser Gly Phe Leu Asn Ser
    130                 135                 140

Ser Thr Lys Ala Pro Asn Phe Val Val Glu Leu Ile Gln Ser Ser Ser
145                 150                 155                 160

Lys Ser Leu Val Leu Ile Leu Asp Leu Pro His Arg Lys Asp Leu Val
                165                 170                 175

Leu Asn Pro Asp Tyr Leu Lys Glu Tyr Tyr Gln Asp Thr Ala Leu Asp
            180                 185                 190

Ser His Arg Gln Ser Leu Leu Lys Leu Pro Glu Val Asn Pro Tyr Val
            195                 200                 205

Ser Pro Ser Leu Phe Val Arg Ser Ala Phe Ser Pro Thr Ala Ser Met
    210                 215                 220

Leu Lys Ile Asp Ala Glu Glu Asp Lys Leu Glu Ile Leu Arg
225                 230                 235                 240

Asp His Val Ser Pro Ala Ala Lys Glu Val Leu Glu Val Trp Leu Glu
                245                 250                 255

Arg Cys Val Lys Glu Glu Glu Lys Ile Val Val Gly Glu Glu Glu
            260                 265                 270

Arg Met Glu Leu Glu Arg Arg Asp Lys Ser Phe Arg Lys Ser Ile
        275                 280                 285

Glu Asp Asp Leu Asp Leu Gln Phe Pro Arg Met Phe Gly Glu Val
    290                 295                 300

Ser Ser Arg Val Val His Ala Ile Lys Glu Ala Phe Gly Val Leu
305                 310                 315
```